United States Patent
Terng et al.

(10) Patent No.: US 9,249,465 B2
(45) Date of Patent: Feb. 2, 2016

(54) MOLECULAR MARKERS FOR LUNG AND COLORECTAL CARCINOMAS

(75) Inventors: Harn-Jing Terng, Banciao (TW); Woan-Jen Lee, Yonghe (TW); Chin-Yu Chen, Keelung (TW)

(73) Assignee: Advpharma, Inc., New Taipei (TW)

( * ) Notice: Subject to any disclaimer, the term of this patent is extended or adjusted under 35 U.S.C. 154(b) by 1018 days.

(21) Appl. No.: 12/550,207

(22) Filed: Aug. 28, 2009

(65) Prior Publication Data

US 2010/0075323 A1    Mar. 25, 2010

Related U.S. Application Data

(60) Provisional application No. 61/099,008, filed on Sep. 22, 2008.

(51) Int. Cl.
*C12Q 1/68* (2006.01)
*C12P 19/34* (2006.01)

(52) U.S. Cl.
CPC ........ *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2006/0019256 A1*    1/2006    Clarke et al. ................ 435/6

OTHER PUBLICATIONS

Buck et al., Research Report, Design Strategies and Performance of Custom DNA Sequencing Primers, BioTechniques 27:528-536 (Sep. 1999).*
Beane, J. et al. A prediction model for lung cancer diagnosis that integrates genomic and clinical features. Cancer Prev Res., vol. 1(1), Jun. 2008.*
Chen, et al., "A five-gene signature and clinical outcome in non-small cell lung cancer", New England J Medicine 356:11-20 (2007).

* cited by examiner

*Primary Examiner* — Kenneth R. Horlick
*Assistant Examiner* — David Thomas
(74) *Attorney, Agent, or Firm* — Wolf, Greenfield & Sacks, P.C.

(57) ABSTRACT

Molecular markers for lung and colorectal carcinomas and methods of using them in blood sample assays are disclosed. The method comprises measuring the expression of the markers in a blood sample from a subject for detecting the presence and/or severity of lung and/or colorectal cancer, and for monitoring and/or assessing the prognosis of the subject's response to a cancer therapy. Also disclosed are kits for detecting, diagnosing, and/or monitoring lung or colorectal carcinomas.

29 Claims, 1 Drawing Sheet

SEQUENCE LISTING

```
<160> NUMBER OF SEQ ID NOS: 161

<210> SEQ ID NO 1
<211> LENGTH: 3486
<212> TYPE: DNA
<213> ORGANISM: Homo sapiens

<400> SEQUENCE: 1
tttccttcct cttttggcaa catggcgggc ggagaagctg gagtgactct agggcagccg        60
catctttcgc gtcaggatct caccaccttg gatgttacca agttgacgcc actttcacac       120
gaagttatca gcagacaagc cacaattaac ataggtacaa ttggtcatgt agctcatggg       180
aaatccacag tcgtcaaagc tatttctgga gttcatactg tcaggttcaa aaatgaacta       240
gaaagaaata ttacaatcaa gcttggatat gctaatgcta agatttataa gcttgatgac       300
ccaagttgcc ctcggccaga atgttataga tcttgtggga gcagtacacc tgacgagttt       360
cctacggaca ttccagggac caaagggaac ttcaaattag tcagacatgt ttcctttgtt       420
gactgtcctg gccacgatat tttgatggct actatgctga acggtgcagc agtgatggat       480
gcagctcttc tgttgatagc tggtaatgaa tcttgccctc agcctcagac atcggaacac       540
ctggctgcta tagagatcat gaaactgaag catattttga ttctacaaaa taaaattgat       600
ttggtaaaag aaagtcaggc taaagaacaa tacgagcaga tccttgcatt tgtccaaggt       660
acagtagcag agggagctcc cattattcca atttcagctc agctgaaata caatattgaa       720
gttgtttgtg agtacatagt aaagaaaatt ccagtacccc caagagactt tacttcagag       780
ccccggctta ttgttattag atcttttgat gtcaacaaac ctggctgtga agttgatgac       840
cttaagggag gtgtagctgg tggtagtatc ctaaaaggag tattaaaggt gggccaggag       900
atagaagtaa gacctggtat tgtttccaaa gatagtgaag gaaaactcat gtgtaaacca       960
atcttttcca aaattgtatc acttttttgcg gagcataatg atctgcaata tgctgctcca      1020
ggcggtctta ttggagttgg aacaaaaatt gaccccactt tgtgccgggc tgacagaatg      1080 gtgggcaag tacttggtgc agtcggagct ttacctgaga tattcacaga attggaaatt      1140
tcctatttcc tgcttagacg gcttctaggt gtacgcactg aaggagacaa gaaagcagca      1200
aaggttcaaa agctgtctaa gaatgaagtg ctcatggtga acataggatc cctgtcaaca      1260
ggagggagag ttagtgctgt caaggccgat ttgggtaaaa ttgttttgac caatccagtg      1320
tgcacagagg taggagaaaa aattgccctt agccgaagag ttgaaaaaca ctggcgttta      1380
attggttggg gtcagataag aagaggagtg acaatcaagc caacagtaga tgatgactga      1440
agaataccag ttaaataata cattcggatg gatttggaag ttggaattcc tcttaacaac      1500 caagggggttt attttcaaag caatattggg gaattgattt cacagttcgt taccttagta      1560
ggtaacggta aggttattct ctttttttt tttttttttt ttggttatga aaacttaggg      1620
actaaaatta atataaaaat tggcataatg ttggattgaa tctacatttt ggcagaagtt      1680
aaacattccc acataatgtc aaaattatac atcatgcagt tctgttttttt tgtttgtttt      1740 attttgtttt gttttgagt ctggctctgt cacccaggct ggagtgcagt ggcgtgatct      1800
```

```
gcaacctctg ccccccgggt tcaagcgatt ctcctgcctc agcctcccga gtagctgaga    1860
ttacaggtgc gcgccaccac acttggctaa ttttttgtatt attagtagag acggggtttc   1920
agcatgttgg ctaggccggt ctctcctgac ctcaggtgga tcagcccacc tcggcctcac    1980
aaagtgctgg gattacaggc gtgagccacc ttgcccagcc cacatcatac agtttgaaat    2040
gaaactttgc cacaaccagc ctttgctgta gcacacacat atatcactga acctgtttga    2100
aataaagttt tttttctttt tcatgattcg tctttgagta cctccaggct gaaagactgt    2160
tgtaccagta aaacttaaa ggcacaaatt ctccttgaag accttctccc ttttatgtgg     2220
ccccatattt tatgttgctt tatctttgaa attttgcatg aaaaggaaat gaatggattc    2280
gaatgaaatt gtccttaga gcatgattac ttgttcccat ggacaaatat ttttctcccc     2340
ttgctcttcc tggcctgaaa cacgggaaac cagagtcaaa agttatctcc ctctccctgt    2400
gatgccttga gattttttc tgcgttgttt aatgcctgaa atccaagtct tcctccatgg     2460
gaaaatactg ttataccaaa taattctaga tgagtaacaa agatcttttt aggccttcat    2520
tttatgtttt ttcttaactg ttatattatg attgtgacat agattatact actactaatt    2580
tttggatgtt tcaaaaggtc aagaagtaaa agatgttaga aagcaatgag tgagtccttt    2640
tgattttaa cttattcccc atgtcccctat acttcgtgtg cttttccttt tttttttga    2700
gacggaggct cactccgtca cctaggctag agtacagtgg cacgatcttg gctcgctgca    2760
acctctgcct ccctgattca agtgattctc gtgcttcagc ctcccatgta gctgatatta    2820
caggcacttg ccaccatacc cggctaattt ttgtattttt agtagagatg gggtttcacc    2880
atgttgccca ggctggtctt gaactcctaa cctcaggtga tccgcccgcc tctgccttcc    2940
aaagtgctgg gattacaggc gtgagccact ctgcccggct tatttttctt tatgtttttg    3000
cttcgtaaga ggttctgttg agcagtgatt tgcaactctt gctgacgttg ctggggaagc    3060
tttaaaaaaa aaaagatgc cccacagaga ttctgatttt aattgttctg atttaattgg    3120
cttggagtag aattcaggca ttgatatctt taaaaactcc ccagtgttga gaaacaaatt    3180
tagagagttg agaagtaggt atattaaatt acagaatctt actgagtttt ggtagactga    3240
taatacaatt tgctttgctt ttcttaaatt tgcattgaga tgggatttga agcatattgt    3300
gctcttgtga atgttgaagt tgcattgtag aagtttagaa gctctggcta tgggttgcct    3360
aaattgatgt tttgaggaag catattaatg ttataaactt cgctgacttt gaaggttgtg    3420
ttgtagcatg aggaacacaa ataaaacaat tctaaatcaa actaaaaaaa aaaaaaaaa    3480
aaaaaa                                                              3486

<210> SEQ ID NO 2
<211> LENGTH: 3804
<212> TYPE: DNA
<213> ORGANISM: Homo sapiens

<400> SEQUENCE: 2
ctgtctgagc atttcactgc ggagcctgag cgcgcctgcc tgggaaaaca ctgcagcggt     60
gctcggactc ctcctgtcca gcaggaggcg cggcccggca gctcccgcat gcgcagtgcg    120
ctcggtgtca gacggcccgg atcccggtta ccggcccctc gctcgctgct cgccagccca    180
gactcggccc tggcagtggc ggctggcgat tcggaccgat ccgacctggg cggaggtggc    240
ccgcgccccg cggcatgagc cggtgaccaa gctcggggcc gagcgggagg cagccgtggc    300
cgagccacag ggatctgatt cctcccaggg ggatgtcctg cgcctcaggg tccggtggtg    360
gcctgcggca tcccttgcgg tgccagaagc cgtgggacga gtgtctttaa tgttatagag    420
```

```
ctactcagag ttgctgtttc tccttgagat gcttttggag tgtgaggaag aggctgtctg    480
tgtcattatg tgtgcgtcgg tcaagtataa tatccggggt cctgccctca tcccaagaat    540
gaagaccaag caccgaatct actatatcac cctcttctcc attgtcctcc tgggcctcat    600
tgccactggc atgtttcagt tttggcccca ttctatcgag tcctcaaatg actggaatgt    660
agagaagcgc agcatccgtg atgtgccggt tgttaggctg ccagccgaca gtcccatccc    720
agagcggggg gatctcagtt gcagaatgca cacgtgtttt gatgtctatc gctgtggctt    780
caacccaaag aacaaaatca aggtgtatat ctatgctctg aaaaagtacg tggatgactt    840
tggcgtctct gtcagcaaca ccatctcccg ggagtataat gaactgctca tggccatctc    900
agacagtgac tactacactg atgcatcaa ccgggcctgt ctgtttgttc cctccatcga    960
tgtgcttaac cagaacacac tgcgcatcaa ggagacagca caagcgatgg cccagctctc   1020
taggtgggat cgaggtacga atcacctgtt gttcaacatg ttgcctggag gtcccccaga   1080
ttataacaca gccctggatg tccccagaga cagggccctg ttggctggtg gcggcttttc   1140
tacgtggact taccggcaag gctacgatgt cagcattcct gtctatagtc cactgtcagc   1200
tgaggtggat cttccagaga aaggaccagg tccacggcaa tacttcctcc tgtcatctca   1260
ggtgggtctc catcctgagt acagagagga cctagaagcc ctccaggtca acatggaga   1320 gtcagtgtta gtactcgata aatgcaccaa cctctcagag ggtgtccttt ctgtccgtaa   1380
gcgctgccac aagcaccagg tcttcgatta cccacaggtg ctacaggagg ctactttctg   1440
tgtggttctt cgtggagctc ggctgggcca ggcagtattg agcgatgtgt acaagctgg   1500 ctgtgtcccg gttgtcattg cagactccta tattttgcct ttctctgaag ttcttgactg   1560
gaagagagca tctgtggttg taccagaaga aaagatgtca gatgtgtaca gtattttgca   1620
gagcatcccc caaagacaga ttgaagaaat gcagagacag gcccggtggt ctgggaagc   1680 gtacttccag tcaattaaag ccattgccct ggccaccctg cagattatca atgaccggat   1740
ctatccatat gctgccatct cctatgaaga atggaatgac cctcctgctg tgaagtgggg   1800
cagcgtgagc aatccactct tcctcccgct gatcccacca cagtctcaag ggttcaccgc   1860
catagtcctc acctacgacc gagtagagag cctcttccgg gtcatcactg aagtgtccaa   1920
ggtgcccagt ctatccaaac tacttgtcgt ctggaataat cagaataaaa accctccaga   1980
agattctctc tggcccaaaa tccgggttcc attaaaagtt gtgaggactg ctgaaaacaa   2040
gttaagtaac cgtttcttcc cttatgatga aatcgagaca gaagctgttc tggccattga   2100
tgatgatatc attatgctga cctctgacga gctgcaattt ggttatgagg tctggcggga   2160
atttcctgac cggttggtgg gttacccggg tcgtctgcat ctctgggacc atgagatgaa   2220
taagtggaag tatgagtctg agtggacgaa tgaagtgtcc atggtgctca ctggggcagc   2280 ttttttatcac aagtatttta attacctgta tacctacaaa atgcctgggg atatcaagaa   2340
ctgggtagat gctcatatga actgtgaaga tattgccatg aacttcctgg tggccaacgt   2400
cacgggaaaa gcagttatca aggtaacccc acgaaagaaa ttcaagtgtc ctgagtgcac   2460
agccatagat gggctttcac tagaccaaac acacatggtg gagaggtcag agtgcatcaa   2520
caagtttgct tcagtcttcg ggaccatgcc tctcaaggtg gtggaacacc gagctgaccc   2580
tgtcctgtac aaagatgact ttcctgagaa gctgaagagc ttccccaaca ttggcagctt   2640
atgaaacgtg tcattggtgg aggtctgaat gtgaggctgg acagaggga gagaacaagg   2700 cctcccagca ctctgatgtc agagtagtag gttaagggtg gaaggttgac ctacttggat   2760
```

```
cttggcatgc acccacctaa cccactttct caagaacaag aacctagaat gaatatccaa   2820
gcacctcgag ctatgcaacc tctgttcttg tatttcttat gatctctgat gggttcttct   2880
cgaaaatgcc aagtggaaga ctttgtggca tgctccagat ttaaatccag ctgaggctcc   2940
ctttgttttc agttccatgt aacaatctgg aaggaaactt cacggacagg aagactgctg   3000
gagaagagaa gcgtgttagc ccatttgagg tctggggaat catgtaaagg gtacccagac   3060
ctcactttta gttatttaca tcaatgagtt ctttcaggga accaaaccca gaattcggtg   3120
caaaagccaa acatcttggt gggatttgat aaatgccttg ggacctggag tgctgggctt   3180
gtgcacagga agagcaccag ccgctgagtc aggatcctgt cagttccatg agctattcct   3240
ctttggtttg gcttttgat atgattaaaa ttatttttta ttccttttc tactgtgtct    3300 taaacaccaa ttcctgatag tccaaggaac caccttctc ccttgatata tttaactccg     3360
tctttggcct gacaacagtc ttctgcccat gtctgggaac acacgccagg aggaatgtct   3420
gataccctct gcatcaagcg taagaaggtc ccaaatcata accattttaa gaacagatga   3480
ctcagaaacc tccagaggaa tctgtttgct tcctgattag atccagtcaa tgttttaaag   3540
gtattgtcag agaaaaacag agggtctgta ctagccatgc aaggagtcgc tctagctggt   3600
acccgtaaaa gttgtgggaa ttgtgacccc catcccaagg ggatgccaaa atttctctca   3660
ttcttttggt ataaacttaa cattagccag ggaggttctg gctaacgtta aatgctgcta   3720
tacaactgct ttgcaacagt tgctggtata tttaaatcat taaatttcag catttactaa   3780
tactgcaaaa aaaaaaaaaa aaaa                                          3804

<210> SEQ ID NO 3
<211> LENGTH: 3533
<212> TYPE: DNA
<213> ORGANISM: Homo sapiens

<400> SEQUENCE: 3
gggtctcgcg gtttgggagc gctactcgcc aggtggactc ggagtccgcg agcgtcgtcg     60
gcaagcggcc gcctttccac ggtaaccgcg cgccggcggg gagggcgtgg cgcggagccg    120
acgggaacgt ccgcgctgcg gagcagggca gggaagccgg gaggcgggcc cggcccgagc    180
ttgtccttgt cgcgcaggta ctccgagcac tatgtcgtcc ccggcgtcga ccccgagccg    240
ccgcggcagc cggcgtggaa gggccacccc cgcccagacg cctcggagtg aggatgccag    300
gtcatctccc tctcagagac gtagaggcga ggattccacc tccacggggg agttgcagcc    360
gatgccaacc tcgcctggag tggacctgca gagccctgct cgcaggacg tgctgttttc     420 cagccctccc caaatgcatt cttcagctat ccctcttgac tttgatgtta gttcaccact    480
gacatacggc actcccagct ctcgggtaga gggaacccca agaagtggtg ttaggggcac    540
acctgtgaga cagaggcctg acctgggctc tgcacagaag ggcctgcaag tggatctgca    600
gtctgacggg gcagcagcag aagatatagt ggcaagtgag cagtctctag gccaaaaact    660
tgtgatctgg ggaacagatg taaatgtggc agcatgcaaa gaaaactttc agagatttct    720
tcagcgtttt attgaccctc tggctaaaga agaagaaaat gttggcatag atattactga    780
acctctatac atgcaacgac ttggggagat taatgttatt ggtgagccat ttttaaatgt    840
gaactgtgaa cacatcaaat catttgacaa aaatttgtac agacaactca tctcttaccc    900
acaggaagtt attccaactt ttgacatggc tgtcaatgaa atcttctttg accgttaccc    960
tgactcaatc ttagaacatc agattcaagt aagaccatta acgcattga agactaagaa    1020 tatgagaaac ctgaatccag aagacattga ccagctcatc accatcagcg gcatggtgat   1080
```

```
caggacatcc cagctgattc ccgagatgca ggaggccttc ttccagtgcc aagtgtgtgc    1140
ccacacgacc cgggtggaga tggaccgcgg ccgcattgca gagcccagtg tgtgcgggcg    1200
ctgccacacc acccacagca tggcactcat ccacaaccgc tccctcttct ctgacaagca    1260
gatgatcaag cttcaggagt ctccggaaga catgcctgca gggcagacac cacacacagt    1320
tatcctgttt gctcacaatg atctcgttga caaggtccag cctggggaca gagtgaatgt    1380
tacaggcatc tatcgagctg tgcctattcg agtcaatcca agagtgagta atgtgaagtc    1440
tgtctacaaa acccacattg atgtcattca ttatcggaaa acggatgcaa aacgtctgca    1500
tggccttgat gaagaagcag aacagaaact tttttcagag aaacgtgtgg aattgcttaa    1560
ggaactttcc aggaaaccag acatttatga gaggcttgct tcagccttgg ctccaagcat    1620
ttatgaacat gaagatataa agaagggaat tttgcttcag ctctttggcg ggacaaggaa    1680
ggattttagt cacactggaa ggggcaaatt tcgggctgag atcaacatct gctgtgtgg     1740
cgaccctggt accagcaagt cccagctgct gcagtacgtg tacaacctcg tccccagggg    1800
ccagtacacg tctgggaagg gctccagtgc agttggcctc actgcgtacg taatgaaaga    1860
ccctgagaca aggcagctgg tcctgcagac aggtgctctt gtcctgagtg acaacggcat    1920
ctgctgtatc gatgagttcg acaagatgaa tgaaagtaca agatcggtat tgcatgaagt    1980
catggaacag cagactctgt ccattgcaaa ggctgggatc atctgtcagc tcaatgcgcg    2040
cacctctgtc ctggcagcag caaatcccat tgagtctcag tggaatccta aaaaaacaac    2100
cattgaaaac atccagctgc tcatactttt attatcaagg tttgatttga tcttcctctt    2160
gctggaccct caggacgaag cctatgacag gcgtctggct caccacctgg tcgcactgta    2220
ctaccagagc gaggagcagg cagaggagga gctcctggac atggcggtgc taaaggacta    2280
cattgcctac gcgcacagca ccatcatgcc gcggctaagt gaggaagcca gccaggctct    2340
catcgaggct tatgtagaca tgaggaagat tggcagtagc cggggaatgg tttctgcata    2400
ccctcgacag ctagagtcat taatccgctt agcagaagcc catgctaaag taagattgtc    2460
taacaaagtt gaagccattg atgtggaaga ggccaaacgc ctccatcggg aagctctgaa    2520
gcagtctgca actgatcccc ggactggcat cgtggacata tctattctta ctacgggat     2580
gagtgccacc tctcgtaaac ggaaagaaga attagctgaa gcattgaaaa agcttatttt    2640
atctaagggc aaaacaccag ctctaaaata ccagcaactt tttgaagata ttcggggaca    2700
atctgacata gcaattacta agatatgtt tgaagaagca ctgcgtgccc tggcagatga     2760
tgatttcctg acagtgactg ggaagaccgt gcgcttgctc tgaagccttg tgagcaagga    2820
aggctccctg catgtcctgc ttgctgcacg ccacatgggt gtggtctgca tctcagttgg    2880
ccgccatcag tgtaaataga gcttaaagtc atggtttggc tgcataaaaa tttctaact     2940
tgggttcaat atttgtagtg aagtatctgt tttcattttt ttcacgttat aaataaaaat    3000
actatgctgg ccgggcgcgg tggctcacac ctgtaatccc agcactttgg gaggccaatg    3060
tgggtggatc atgaggtcag gagttcaaga ccagcctagc caagatggtg aaaccccgtc    3120
tctagtaaag ataacaaaaa attagctggg cttgatggca tgcgcctgta atcccagcta    3180
ctcgggaggt tgaggcagga gaatcgctta acccaggcg gcagaggttg cagtgagcca     3240
agatcgcgcc actgcactcc agcctcagca atagagtgag actgtctcaa aaaaaaaaa     3300
aaaaaaaaaa cctgccaatt ttcaaacata ccgtagagat tattttcagg tgccatttta    3360
tagtatagca gcagggcttt tactctgtgt atgcacagat gcagtctggg gcatggtttg    3420
```

```
tgtgctggac tttctcatgg ccatcatcag tatgcttatg gatttgatga caggcatagc    3480
ctgggcatat cacctcattg gtaaagggct agagcctttc tttttatgg cac            3533

<210> SEQ ID NO 4
<211> LENGTH: 2357
<212> TYPE: DNA
<213> ORGANISM: Homo sapiens

<400> SEQUENCE: 4
cgagcttggc tgcttctggg gcctgtgtgg ccctgtgtgt cggaaagatg gagcaagaag     60
ccgagcccga ggggcggccg cgaccctct gaccgagatc ctgctgcttt cgcagccagg     120
agcaccgtcc ctccccggat tagtgcgtac gagcgcccag tgccctggcc cggagagtgg    180
aatgatcccc gaggcccagg gcgtcgtgct tccgcgcgcc ccgtgaagga aactggggag    240
tcttgaggga cccccgactc caagcgcgaa aaccccggat ggtgaggagc aggcaaatgt    300
gcaataccaa catgtctgta cctactgatg gtgctgtaac cacctcacag attccagctt    360
cggaacaaga gaccctggtt agaccaaagc cattgctttt gaagttatta aagtctgttg    420
gtgcacaaaa agacacttat actatgaaag aggttctttt ttatcttggc cagtatatta    480
tgactaaacg attatatgat gagaagcaac aacatattgt atattgttca aatgatcttc    540
taggagattt gtttggcgtg ccaagcttct ctgtgaaaga gcacaggaaa atatatacca    600
tgatctacag gaacttggta gtagtcaatc agcaggaatc atcggactca ggtacatctg    660
tgagtgagaa caggtgtcac cttgaaggtg ggagtgatca aaaggacctt gtacaagagc    720
ttcaggaaga gaaaccttca tcttcacatt tggtttctag accatctacc tcatctagaa    780
ggagagcaat tagtgagaca gaagaaaatt cagatgaatt atctggtgaa cgacaaagaa    840
aacgccacaa atctgatagt atttcccttt cctttgatga aagcctggct ctgtgtgtaa    900
taagggagat atgttgtgaa agaagcagta gcagtgaatc tacagggacg ccatcgaatc    960
cggatcttga tgctggtgta agtgaacatt caggtgattg gttggatcag gattcagttt   1020
cagatcagtt tagtgtagaa tttgaagttg aatctctcga ctcagaagat tatagcctta   1080
gtgaagaagg acaagaactc tcagatgaag atgatgaggt atatcaagtt actgtgtatc   1140
aggcagggga gagtgataca gattcatttg aagaagatcc tgaaatttcc ttagctgact   1200
attggaaatg cacttcatgc aatgaaatga atccccccct tccatcacat tgcaacagat   1260
gttgggccct tcgtgagaat tggcttcctg aagataaagg gaaagataaa ggggaaatct   1320
ctgagaaagc caaactggaa aactcaacac aagctgaaga gggctttgat gttcctgatt   1380
gtaaaaaaac tatagtgaat gattccagag agtcatgtgt tgaggaaaat gatgataaaa   1440
ttacacaagc ttcacaatca caagaaagtg aagactattc tcagccatca acttctagta   1500
gcattattta tagcagccaa gaagatgtga aagagtttga agggaagaa acccaagaca    1560 aagaagagag tgtggaatct agtttgcccc ttaatgccat tgaaccttgt gtgatttgtc    1620
aaggtcgacc taaaaatggt tgcattgtcc atggcaaaac aggacatctt atggcctgct   1680
ttacatgtgc aaagaagcta agaaaaagga ataagccctg cccagtatgt agacaaccaa   1740
ttcaaatgat tgtgctaact tatttcccct agttgacctg tctataagag aattatatat   1800
ttctaactat ataaccctag gaatttagac aacctgaaat ttattcacat atatcaaagt   1860
gagaaaatgc ctcaattcac atagattcct tctctttagt ataattgacc tactttggta   1920
gtggaatagt gaatacttac tataatttga cttgaatatg tagctcatcc tttcaccaa    1980 ctcctaattt taaataattt ctactctgtc ttaaatgaga agtacttggt ttttttttt    2040
```

```
cttaaatatg tatatgacat ttaaatgtaa cttattattt tttttgagac cgagtcttgc   2100
tctgttaccc aggctggagt gcagtggcgt gatcttggct cactgcaagc tctgcctccc   2160
gggttcgcac cattctcctg cctcagcctc ccaattagct tggcctacag tcatctgcca   2220
ccacacctgg ctaattttt gtacttttag tagagacagg gtttcaccgt gttagccagg   2280
atggtctcga tctcctgacc tcgtgatccg cccacctcgg cctcccaaag tgctgggatt   2340
acaggcatga gccaccg                                                  2357

<210> SEQ ID NO 5
<211> LENGTH: 3303
<212> TYPE: DNA
<213> ORGANISM: Homo sapiens

<400> SEQUENCE: 5
agttctcgcg ggacaccgac ggggagcgga agccaggagg tattgctgct tcggcgaccg     60
ggcggcggca gcggcggcgg cggctgtggc agagtctgtg cctgtggcgg tgacggcggc    120
gggagcaagc gctgccctcg cagagcagcc ttggggtcgc cggccgctcg cagcgttgtg    180
gaggggcggg ccgacgctg agcggagcag ctgcgccacg ggtggcattg tgtgtcccag     240
agtgccggag cgagtcccag aagagaggcg aggctaagcc cagagcgctg ggttgcttca    300
gcagggaaga ctcccttccc cctgcttcag gctgctgagc actgagcagc gctcagaatg    360
gaagccatcg ccaaatatga cttcaaagct actgcagacg acgagctgag cttcaaaagg    420
ggggacatcc tcaaggtttt gaacgaagaa tgtgatcaga actggtacaa ggcagagctt    480
aatggaaaag acggcttcat tcccaagaac tacatagaaa tgaaaccaca tccgtggttt    540
tttggcaaaa tccccagagc caaggcagaa gaaatgctta gcaaacagcg gcacgatggg    600
gcctttctta tccgagagag tgagagcgct cctggggact tctccctctc tgtcaagttt    660
ggaaacgatg tgcagcactt caaggtgctc cgagatggag ccgggaagta cttcctctgg    720
gtggtgaagt tcaattcttt gaatgagctg gtggattatc acagatctac atctgtctcc    780
agaaaccagc agatattcct gcgggacata gaacaggtgc cacagcagcc gacatacgtc    840
caggccctct ttgactttga tcccaggag gatggagagc tgggcttccg ccggggagat    900
tttatccatg tcatggataa ctcagacccc aactggtgga aaggagcttg ccacgggcag    960
accggcatgt tccccgcaa ttatgtcacc cccgtgaacc ggaacgtcta agagtcaaga   1020
agcaattatt taaagaaagt gaaaatgta aaacacatac aaaagaatta acccacaag    1080 ctgcctctga cagcagcctg tgaggagtg cagaacacct ggccgggtca ccctgtgacc   1140
ctctcacttt ggttggaact ttaggggtg ggaggggcg ttggatttaa aaatgccaaa    1200
acttacctat aaattaagaa gagttttat tacaaatttt cactgctgct cctctttccc    1260
ctcctttgtc ttttttttca tcctttttc tcttctgtcc atcagtgcat gacgtttaag    1320
gccacgtata gtcctagctg acgccaataa taaaaaacaa gaaaccaagt gggctggtat    1380
tctctctatg caaaatgtct gttttagttg gaatgactga agaagaaca gctgttcctg     1440 tgttcttcgt atatacacac aaaaaggagc gggcagggcc gctcgatgcc tttgctgttt    1500
agcttcctcc agaggagggg acttgtagga atctgccttc cagcccagac ccccagtgta    1560
ttttgtccaa gttcacagta gagtagggta aaggaaagc atgtctctgc ttccatggct    1620
tcctgagaaa gccacctggg gctgggcgcg gtggctcacg cctgtaatcc cagcactttg    1680
ggaggccaag gtgggcggat cacaaggtca ggagttcgag accaacctag ccaacatggt    1740
```

-continued

| | |
|---|---|
| gaaaccccgt ctctactaaa aataagaaat tagccgggtg tggcacgcac ctgtagtccc | 1800 |
| agctacttgg gagcctgagg caggagaatc gcttgaacct gggaagtgga ggttgagtga | 1860 |
| gccgggaccg tgccattgta ctccagcctg ggtgacagag cgagattccg tctcaaaaaa | 1920 |
| aaaaaaaaaa agcccacctg aaagcctgtc tctttccact tgttggccc ttccagtggg | 1980 |
| attatcgagc atgttgtttt ttcatagtgc cttttccctt atttcaaggg ttgcttctga | 2040 |
| gtggtgtttt ttttttttt ttaatttgtt ttgttttaaa ataagttaaa ggcagtccag | 2100 |
| agcttttcag ccaatttgtc tcctactctg tgtaaatatt tttccctccg ggcaggggag | 2160 |
| ccagggtaga gcaaaggaga caaagcagga gtggaaggtg aggcgttctc ctgcttgtac | 2220 |
| taagccagga ggctttaagc tccagcttta agggttgtga gccccttggg ggttcaggga | 2280 |
| actgcttgcc cagggtgcag tgtgagtgtg atgggccacc ggggcaagag ggaaggtgac | 2340 |
| cgcccagctc tcccacatcc cactggatct ggcttacagg ggggtcggaa gcctgtcctc | 2400 |
| accgtctcgg gggttgtggc ccccgccccc tccctatatg caccccctgga accagcaagt | 2460 |
| cccagacaag gagagcggag gaggaagtca tgggaacgca gcctccagtt gtagcaggtt | 2520 |
| tcactattcc tatgctgggg tacacagtga gagtactcac ttttcacttg tcttgctctt | 2580 |
| agattgggcc atggctttca tcctgtgtcc cctgacctgt ccaggtgagt gtgagggcag | 2640 |
| cactgggaag ctggagtgct gcttgtgcct cccttcccag tgggctgtgt tgactgctgc | 2700 |
| tccccacccc taccgatggt cccaggaagc agggagagtt ggggaaggca agattggaaa | 2760 |
| gacaggaaga ccaaggcctc ggcagaactc tctgtcttct ctccacttct ggtcccctgt | 2820 |
| ggtgatgtgc ctgtaatctt tttctccacc caaacccctt cccacgacaa aaacaagact | 2880 |
| gcctccctct cttccgggag ctggtgacag ccttgggcct ttcagtccca agcggccga | 2940 |
| tgggagtctc cctccgactc cagatatgaa cagggcccag gcctggagcg tttgctgtgc | 3000 |
| caggaggcgg cagctcttct gggcagagcc tgtccccgcc ttccctcact cttcctcatc | 3060 |
| ctgcttctct tttcctcgca gatgataaaa ggaatctggc attctacacc tggaccattt | 3120 |
| gattgtttta ttttggaatt ggtgtatatc atgaagcctt gctgaactaa gttttgtgtg | 3180 |
| tatatattta aaaaaaaaat cagtgtttaa ataaagacct atgtacttaa tcctttaact | 3240 |
| ctgcggatag catttggtag gtagtgatta actgtgaata ataaatacac aatgaattct | 3300 |
| tca | 3303 |

<210> SEQ ID NO 6
<211> LENGTH: 12331
<212> TYPE: DNA
<213> ORGANISM: Homo sapiens

<400> SEQUENCE: 6

| | |
|---|---|
| acttccggtg gggtgtcatg gcggcgtctc ggactgtgat ggctgtgggg agacggcgct | 60 |
| agtggggaga gcgaccaaga ggccccctcc cctccccggg tcccctccc ctatccccct | 120 |
| cccccccagcc tccttgccaa cgcccccttt ccctctcccc ctcccgctcg cgcgctgaccc | 180 |
| cccatccccca cccccgtggg aacactggga gcctgcactc cacagaccct ctccttgcct | 240 |
| cttccctcac ctcagcctcc gctccccgcc tcttcccgg ccagggcgc cggcccaccc | 300 |
| ttccctccgc cgccccccgg ccgcggggag gacatggccg cgcacaggcc ggtggaatgg | 360 |
| gtccaggccg tggtcagccg cttcgacgag cagcttccaa taaaaacagg acagcagaac | 420 |
| acacatacca aagtcagtac tgagcacaac aaggaatgtc taatcaatat ttccaaatac | 480 |
| aagttttctt tggttataag cggcctcact actatttaa agaatgttaa caatatgaga | 540 |

-continued

```
atatttggag aagctgctga aaaaaattta tatctctctc agttgattat attggataca    600
ctggaaaaat gtcttgctgg gcaaccaaag gacacaatga gattagatga acgatgctg    660
gtcaaacagt tgctgccaga aatctgccat tttcttcaca cctgtcgtga aggaaaccag    720
catgcagctg aacttcggaa ttctgcctct ggggttttat tttctctcag ctgcaacaac    780
ttcaatgcag tctttagtcg catttctacc aggttacagg aattaactgt tgttcagaa     840
gacaatgttg atgttcatga tatagaattg ttacagtata tcaatgtgga ttgtgcaaaa    900
ttaaaacgac tcctgaagga aacagcattt aaatttaaag ccctaaagaa ggttgcgcag    960
ttagcagtta taaatagcct ggaaaaggca ttttggaact gggtagaaaa ttatccagat   1020
gaatttacaa aactgtacca gatcccacag actgatatgg ctgaatgtgc agaaaagcta   1080
tttgacttgg tggatggttt tgctgaaagc accaaacgta agcagcagt ttggccacta    1140
caaatcattc tccttatctt gtgtccagaa ataatccagg atatatccaa agacgtggtt   1200
gatgaaaaca acatgaataa gaagttattt ctggacagtc tacgaaaagc tcttgctggc   1260
catggaggaa gtaggcagct gacagaaagt gctgcaattg cctgtgtcaa actgtgtaaa   1320
gcaagtactt acatcaattg ggaagataac tctgtcattt tcctacttgt tcagtccatg   1380
gtggttgatc ttaagaacct gctttttaat ccaagtaagc cattctcaag aggcagtcag   1440
cctgcagatg tggatctaat gattgactgc cttgtttctt gctttcgtat aagccctcac   1500
aacaaccaac actttaagat ctgcctggct cagaattcac cttctacatt tcactatgtg   1560
ctggtaaatt cactccatcg aatcatcacc aattccgcat tggattggtg gcctaagatt   1620
gatgctgtgt attgtcactc ggttgaactt cgaaatatgt ttggtgaaac acttcataaa   1680
gcagtgcaag gttgtggagc acacccagca atacgaatgg caccgagtct tacatttaaa   1740
gaaaaagtaa caagccttaa atttaaagaa aaacctacag acctggagac aagaagctat   1800
aagtatcttc tcttgtccat ggtgaaaacta attcatgcag atccaaagct cttgcttttgt  1860
aatccaagaa aacaggggcc cgaaacccaa ggcagtacag cagaattaat tacagggctc   1920
gtccaactgg tccctcagtc acacatgcca gagattgctc aggaagcaat ggaggctctg   1980
ctggttcttc atcagttaga tagcattgat ttgtggaatc ctgatgctcc tgtagaaaca   2040
ttttgggaga ttagctcaca aatgcttttt tacatctgca agaaattaac tagtcatcaa   2100
atgcttagta gcacagaaat tctcaagtgg ttgcgggaaa tattgatctg caggaataaa   2160
tttcttctta aaataagca ggcagataga agttcctgtc actttctcct tttttacggg    2220
gtaggatgtg atattccttc tagtggaaat accagtcaaa tgtccatgga tcatgaagaa   2280
ttactacgta ctcctggagc ctctctccgg aagggaaaag ggaactcctc tatggatagt   2340
gcagcaggat gcagcggaac cccccgatt tgccgacaag cccagaccaa actagaagtg    2400
gccctgtaca tgtttctgtg gaaccctgac actgaagctg ttctggttgc catgtcctgt   2460
ttccgccacc tctgtgagga agcagatatc cggtgtgggg tggatgaagt gtcagtgcat   2520
aacctcttgc ccaactataa cacattcatg gagtttgcct ctgtcagcaa tatgatgtca   2580
acaggaagag cagcacttca gaaaagagtg atggcactgc tgaggcgcat tgagcatccc   2640
actgcaggaa acactgaggc ttgggaagat acacatgcaa aatgggaaca agcaacaaag   2700
ctaatcctta actatccaaa agccaaaatg gaagatggcc aggctgctga aagccttcac   2760
aagaccattg ttaagaggcg aatgtccat gtgagtggag gaggatccat agatttgtct    2820
gacacagact ccctacagga atggatcaac atgactggct tcctttgtgc ccttgggggga   2880
```

```
gtgtgcctcc agcagagaag caattctggc ctggcaacct atagcccacc catgggtcca    2940
gtcagtgaac gtaagggttc tatgatttca gtgatgtctt cagagggaaa cgcagataca    3000
cctgtcagca aatttatgga tcggctgttg tccttaatgg tgtgtaacca tgagaaagtg    3060
ggacttcaaa tacggaccaa tgttaaggat ctggtgggtc tagaattgag tcctgctctg    3120
tatccaatgc tatttaacaa attgaagaat accatcagca agttttttga ctcccaagga    3180
caggttttat tgactgatac caatactcaa tttgtagaac aaaccatagc tataatgaag    3240
aacttgctag ataatcatac tgaaggcagc tctgaacatc tagggcaagc tagcattgaa    3300
acaatgatgt taaatctggt caggtatgtt cgtgtgcttg ggaatatggt ccatgcaatt    3360
caaataaaaa cgaaactgtg tcaattagtt gaagtaatga tggcaaggag agatgacctc    3420
tcattttgcc aagagatgaa atttaggaat aagatggtag aatacctgac agactgggtt    3480
atgggaacat caaccaagc agcagatgat gatgtaaaat gtcttacaag agatttggac    3540
caggcaagca tggaagcagt agtttcactt ctagctggtc tccctctgca gcctgaagaa    3600
ggagatggtg tggaattgat ggaagccaaa tcacagttat tcttaaaata cttcacatta    3660
tttatgaacc ttttgaatga ctgcagtgaa gttgaagatg aaagtgcgca aacaggtggc    3720
aggaaacgtg gcatgtctcg gaggctggca tcactgaggc actgtacggt ccttgcaatg    3780
tcaaacttac tcaatgccaa cgtagacagt ggtctcatgc actccatagg cttaggttac    3840
cacaaggatc tccagacaag agctacattt atggaagttc tgacaaaaat ccttcaacaa    3900
ggcacagaat ttgacacact tgcagaaaca gtattggctg atcggtttga gagattggtg    3960
gaactggtca caatgatggg tgatcaagga gaactcccta tagcgatggc tctggccaat    4020
gtggttcctt gttctcagtg ggatgaacta gctcgagttc tggttactct gtttgattct    4080
cggcatttac tctaccaact gctctggaac atgttttcta aagaagtaga attggcagac    4140
tccatgcaga ctctcttccg aggcaacagc ttggccagta aaataatgac attctgtttc    4200
aaggtatatg gtgctaccta tctacaaaaa ctcctggatc cttttattcg aattgtgatc    4260
acatcctctg attggcaaca tgttagcttt gaagtggatc ctaccaggtt agaaccatca    4320
gagagccttg aggaaaacca gcggaacctc cttcagatga ctgaaaagtt cttccatgcc    4380
atcatcagtt cctcctcaga attccccct caacttcgaa gtgtgtgcca ctgtttatac    4440
caggtggtta gccagcgttt ccctcagaac agcatcggtg cagtaggaag tgccatgttc    4500
ctcagattta tcaatcctgc cattgtctca ccgtatgaag cagggatttt agataaaaag    4560
ccaccaccta gaatcgaaag gggcttgaag ttaatgtcaa agatacttca gagtattgcc    4620
aatcatgttc tcttcacaaa agaagaacat atgcggcctt tcaatgattt tgtgaaaagc    4680
aactttgatg cagcacgcag gttttttcctt gatatagcat ctgattgtcc tacaagtgat    4740
gcagtaaatc atagtctttc cttcataagt gacggcaatg tgcttgcttt acatcgtcta    4800
ctctggaaca atcaggagaa aattgggcag tatctttcca gcaacaggga tcataaagct    4860
gttggaagac gaccttttga taagatggca acacttcttg cataccctggg tcctccagag    4920 cacaaacctg tggcagatac acactggtcc agccttaacc ttaccagttc aaagtttgag    4980
gaatttatga ctaggcatca ggtacatgaa aaagaagaat tcaaggcttt gaaaacgtta    5040
agtattttct accaagctgg gacttccaaa gctgggaatc ctattttta ttatgttgca    5100 cggaggttca aaactggtca aatcaatggt gatttgctga tataccatgt cttactgact    5160
ttaaagccat attatgcaaa gccatatgaa attgtagtgg accttaccca taccgggcct    5220
agcaatcgct ttaaaacaga cttttctctct aagtggtttg ttgttttttcc tggctttgct    5280
```

```
tacgacaacg tctccgcagt ctatatctat aactgtaact cctgggtcag ggagtacacc   5340
aagtatcatg agcggctgct gactggcctc aaaggtagca aaaggcttgt tttcatagac   5400
tgtcctggga aactggctga gcacatagag catgaacaac agaaactacc tgctgccacc   5460
ttggctttag aagaggacct gaaggtattc cacaatgctc tcaagctagc tcacaaagac   5520
accaaagttt ctattaaagt tggttctact gctgtccaag taacttcagc agagcgaaca   5580
aaagtcctag ggcaatcagt ctttctaaat gacatttatt atgcttcgga aattgaagaa   5640
atctgcctag tagatgagaa ccagttcacc ttaaccattg caaaccaggg cacgccgctc   5700
accttcatgc accaggagtg tgaagccatt gtccagtcta tcattcatat ccggacccgc   5760
tgggaactgt cacagcccga ctctatcccc aacacacca agattcggcc aaaagatgtc   5820
cctgggacac tgctcaatat cgcattactt aatttaggca gttctgaccc gagtttacgg   5880
tcagctgcct ataatcttct gtgtgcctta acttgtacct ttaatttaaa aatcgagggc   5940
cagttactag agacatcagg tttatgtatc cctgccaaca acaccctctt tattgtctct   6000
attagtaaga cactggcagc caatgagcca cacctcacgt tagaattttt ggaagagtgt   6060
atttctggat ttagcaaatc tagtattgaa ttgaaacacc tttgtttgga atacatgact   6120
ccatggctgt caaatctagt tcgttttttgc aagcataatg atgatgccaa acgacaaaga   6180
gttactgcta ttcttgacaa gctgataaca atgaccatca atgaaaaaca gatgtaccca   6240
tctattcaag caaaaatatg gggaagcctt gggcagatta cagatctgct tgatgttgta   6300
ctagacagtt tcatcaaaac cagtgcaaca ggtggcttgg gatcaataaa agctgaggtg   6360
atggcagata ctgctgtagc tttggcttct ggaaatgtga aattggtttc aagcaaggtt   6420
attggaagga tgtgcaaaat aattgacaag acatgcttat ctccaactcc tactttagaa   6480
caacatctta tgtgggatga tattgctatt ttagcacgct acatgctgat gctgtccttc   6540
aacaattccc ttgatgtggc agctcatctt ccctacctct tccacgttgt tactttctta   6600
gtagccacag gtccgctctc ccttagagct tccacacatg gactggtcat taatatcatt   6660
cactctctgt gtacttgttc acagcttcat tttagtgaag agaccaagca gttttgaga   6720
ctcagtctga cagagttctc attacccaaa ttttacttgc tgtttggcat tagcaaagtc   6780
aagtcagctg ctgtcattgc cttccgttcc agttaccggg acaggtcatt ctctcctggc   6840
tcctatgaga gagagacttt tgctttgaca tccttggaaa cagtcacaga gctttgttg   6900
gagatcatgg aggcatgcat gagagatatt ccaacgtgca gtggctgga ccagtggaca   6960
gaactagctc aaagatttgc attccaatat aatccatccc tgcaaccaag agctcttgtt   7020
gtctttgggt gtattagcaa acgagtgtct catgggcaga taaagcagat aatccgtatt   7080
cttagcaagg cacttgagag ttgcttaaaa ggacctgaca cttacaacag tcaagttctg   7140
atagaagcta cagtaatagc actaaccaaa ttacagccac ttcttaataa ggactcgcct   7200
ctgcacaaag ccctcttttg ggtagctgtg gctgtgctgc agcttgatga ggtcaacttg   7260
tattcagcag gtaccgcact tcttgaacaa aacctgcata ctttagatag tctccgtata   7320
ttcaatgaca agagtccaga ggaagtattt atggcaatcc ggaatcctct ggagtggcac   7380
tgcaagcaaa tggatcattt tgttggactc aatttcaact ctaactttaa cttttgcattg   7440
gttggacacc tttttaaaagg gtacaggcat ccttcacctg ctattgttgc aagaacagtc   7500
agaatttttac atacactact aactctggtt aacaaacaca gaaattgtga caaatttgaa   7560
gtgaatacac agagcgtggc ctacttagca gctttactta cagtgtctga agaagttcga   7620
```

```
agtcgctgca gcctaaaaca tagaaagtca cttcttctta ctgatatttc aatggaaaat   7680
gttcctatgg atacatatcc cattcatcat ggtgaccctt cctataggac actaaaggag   7740
actcagccat ggtcctctcc caaaggttct gaaggatacc ttgcagccac ctatccaact   7800
gtcggccaga ccagtcccg agccaggaaa tccatgagcc tggacatggg gcaaccttct   7860
caggccaaca ctaagaagtt gcttggaaca aggaaaagtt ttgatcactt gatatcagac   7920
acaaaggctc ctaaaaggca agaaatggaa tcagggatca caacaccccc caaaatgagg   7980
agagtagcag aaactgatta tgaaatggaa actcagagga tttcctcatc acaacagcac   8040
ccacatttac gtaaagtttc agtgtctgaa tcaaatgttc tcttggatga agaagtactt   8100
actgatccga agatccaggc gctgcttctt actgttctag ctacactggt aaaatatacc   8160
acagatgagt tgatcaacg aattctttat gaatacttag cagaggccag tgttgtgttt   8220
cccaaagtct ttcctgttgt gcataaattg ttggactcta agatcaacac cctgttatca   8280
ttgtgccaag atccaaattt gttaaatcca atccatggaa ttgtgcagag tgtggtgtac   8340
catgaagaat ccccaccaca ataccaaaca tcttacctgc aaagttttgg ttttaatggc   8400
ttgtggcggt ttgcaggacc gttttcaaag caaacacaaa ttccagacta tgctgagctt   8460
attgttaagt ttcttgatgc cttgattgac acgtacctgc ctggaattga tgaagaaacc   8520
agtgaagaat ccctcctgac tcccacatct ccttaccctc ctgcactgca gagccagctt   8580
agtatcactg ccaaccttaa ccttttctaat tccatgacct cacttgcaac ttcccagcat   8640
tccccaggaa tcgacaagga gaacgttgaa ctctcccta ccactggcca ctgtaacagt   8700
ggacgaactc gccacggatc cgcaagccaa gtgcagaagc aaagaagcgc tggcagtttc   8760
aaacgtaata gcattaagaa gatcgtgtga agcttgcttg ctttcttttt taaaatcaac   8820
ttaacatggg ctcttcacta gtgacccctt ccctgtcctt gcccttttcc cccatgttgt   8880
aatgctgcac ttcctgtttt ataatgaacc catccggttt gccatgttgc cagatgatca   8940
actcttcgaa gccttgccta aatttaatgc tgccttttct ttaactttttt tcttctact   9000 tttggcgtgt atctggtata tgtaagtgtt cagaacaact gcaaagaaag tgggaggtca   9060
ggaaactttt aactgagaaa tctcaattgt aagagaggat gaattcttga atactgctac   9120
tactggccag tgatgaaagc catttgcaca gagctctgcc ttctgtggtt ttccctttctt   9180 catcctacag agtaaagtgt tagtcctatt tatacatttt tcaagataca agtttatgag   9240
agaaatagta ttataacccc agtatgttta atctttagc tgtggacttt tttttaacc    9300 gtacaaaact gaaagaacca tagaggtcaa gcctcagtga cttgacacca taaagccaca   9360
gacaaggtac ttggggggga gggcagggaa atttcatatt ttatagtgga ttcttaagaa   9420
atactaacac ttgagtatta gcaataatta caggaaaata agtgcgacca catatatctt   9480
aacattactg aattaaaact atggcttcta agtccttatc caaactcagt catccaaact   9540
agtttatttt tttctccagt tgattatctt ttaattttta attttgctaa aggtggtttt   9600
tttgtgtttt gttttttgta aaccaaaact atactaagta tagtaattat atatatatat   9660
atattttttc ccctccccct cttctttcct aactaattct gagcagggta atcagtgaac   9720
aaagtgttga aaattgttcc cagaaggtaa ttttcataga tgtttgcatt agctccatag   9780
caaaatggaa tggtacgtga catttagggt agctgatatt tttattttgt taaataattt   9840
ccaagaatag agtatggtgt atattataaa tttctttgat aagatgtatt ttgaatgtct   9900
tttaatcttc ctcctcctct ccaaaaaaat cagaaacctc tttaagaaaa catgtaggtt   9960
atatatgcta gaattgcatt taatcactgt gaaaagactg gtcagcctgc attagtatga  10020
```

-continued

```
cagtagggggg gctgttagaa ttgctgctat actggtggta tggattatca tggcattgga   10080
attttcatag taatgcagat ccaatttctt tgtggtacct gcagtttaca aaataatttg   10140
acttcagtga gcatattggt atctggatgt tccaatttag aactaaacca tatttattac   10200
aaaaagatat taatccctct actcccaggt tcccttttata tgttaagata taatggcttt   10260 gagggggaa aaaataaacc taggggagag gggagtttcc tgtagtgctg tttcattaga   10320
ggatttcagt aaattaaatt ccacagctaa ttcaataaat aatggtacat ttaagtgttc   10380
tgattttaat aatatatttc acatttatcc acacagtaac aatgtaatat gttaatgtaa   10440
ataaaattgg ttttgatact cagaaataac aagaatttaa tttttaaat ttgtttacag   10500 tcctgggaaa agtaagaatt atttgccaaa ataagaggaa agaaaaccct agtattatta   10560
atgagtttac catagaattg ttggaaatac tgaagacagg tgcaatttac taaacttttg   10620
tttttaaact attgtagagg ctgcattaga agaaaatgtt tataatgaca gagcaactat   10680
gactatataa aaaagctgaa attagaactg tgtttagaaa tagatcagta acccagtgcc   10740
aaggatgcca agctgccacc atggtcttgg ctctcccaca acccagtgtt tctggggtaa   10800
gtttcacagt ttctaggccc tggaatagca ggcagtgtaa gcctttgata actttagttc   10860 gatgttttttc ttgttttttgt ttgttggttt ggtgcatatg atagtgggtg ttatgctatt   10920
ttgctcttcc catcaaaata aagaaacttc cagaggttta ctgttaaaaa tactgatatt   10980
tccataaacg ggtttaccaa gggtgtagta tttcataccg cctgaaatga tcagcattgg   11040
cacaaatcaa aattcagccg cctttgaaat gcaaaatac ctttgactag taagtacatc   11100
ctaggagttt gaaaacttaa ctaaggttta aaatttacct tgtttaaaga acttctgact   11160 tttgaggaaaa atctagcttt ccaagtaact aaaatgtaca tgagataaac ctctcaccac   11220
tatgtgtccc ttgagaaatg caacactttt ttagtcttca tacttgtaat ctataaaga   11280 aattctgaag tttagaccaa gttgcccatt tctgcgtaat tgacataagt tctgttaaaa   11340
atattataag taattcgttt cggtttgtag atgtttcccc tgacttgtta aagaggaaac   11400
caggaactca gtcatgtttt tgtcctggat aatctacctg ttatgccagt actcccatcc   11460
gaggggcatg cccttagttg cccagatgga gatgcagttc agtagatttg gggcaaagtg   11520
gctacagctc tgtcttccat tcactcaaca cctgttcatg actgagccag gtgcccagga   11580
cacatcctaa acagtcagct tctatcctgt gtcctagttg gggagacaga gtgccagcca   11640
gcaaccctcc caggtttgta ggttttaggg gttttcagtt ttgtttgggt tttttgtttt   11700 ttgttttttgt ttctacatcc ttccccgact cccaggcata atgaggcatg tcttactcaa   11760
tgttatgcaa tggatttagg caaaaattca ttcttagtgt cagccacaca atttttttta   11820
atgcagtata ttcacctgta aatagtttgt gtaaaatttg acaaaaaaag tatatttact   11880
atactgtaaa tatatgtgat gatatattgt attatttttgc ttttttgtaa agcagttagt   11940
tgctgcacat ggataacaac aaaaatttga ttattctcgt gttagtattg ttaacttctt   12000
tttgcgactg cgttacatca tttaaagaaa atgctgtgta ttgtaaactt aaattgtata   12060
tgataactta ctgtccttc catccgggcc taaactttgg cagttccttt gtctacaacc   12120
ttgttaatac tgtaaacagt tgtacgccag caggaaaaat actgcccaac agacaaaatc   12180
gatcattgta ggggaaaatc atagaaatcc atttcagatc tttattgttc ctcaccccat   12240
tttcctcctt gtgtatgtac ttcccccacc cccttttttt taagtaaaat gtaaattcaa   12300
tctgctctaa gaaaaaaaaa aaaaaaaaaa a                                   12331
```

<210> SEQ ID NO 7
<211> LENGTH: 2723
<212> TYPE: DNA
<213> ORGANISM: Homo sapiens

<400> SEQUENCE: 7

| | | | | | |
|---|---|---|---|---|---|
| gggcggggcg | caggagcccc | ggggcggagg | agccgggag | gcgggaggcg | ggaggcggga | 60 |
| ggtgttgggg | ccgttgaagc | ggcctccctc | ccgccccag | ccgcccggtc | tggcccagc | 120 |
| cctgtcccga | ccccggcct | ggcccactcc | gaccctaccc | ggccgaaggg | ttccgctgga | 180 |
| cacgcaggcg | gcctccggag | cagcccaagc | ccatgagggc | cgcgcgcccg | gccgccggtg | 240 |
| ctgacgagac | ggagctcctg | gccccgagg | aggagcagag | gatcaatgcg | gttcaagaat | 300 |
| cgattccagc | ggttcatgaa | ccatcgagct | ccagccaatg | gccgctacaa | gccaacttgc | 360 |
| tatgaacatg | ctgctaactg | ttacacacac | gcattcctca | ttgttccggc | catcgtgggc | 420 |
| agtgccctcc | tccatcggct | gtctgatgac | tgctgggaaa | agataacagc | atggatttat | 480 |
| ggaatgggac | tctgtgccct | cttcatcgtt | tctacagtat | ttcacattgt | atcatggaaa | 540 |
| aagagccact | taaggacagt | ggagcattgt | tttcacatgt | gtgatagaat | ggttatctat | 600 |
| ttcttcattg | ctgcttctta | tgctccatgg | ttaaatcttc | gtgaacttgg | accctggca | 660 |
| tctcatatgc | gttggtttat | ctggctcatg | gcagctggag | gaaccattta | tgtatttctc | 720 |
| taccatgaaa | aatataaggt | ggttgaactc | ttttctatc | tcacaatggg | attctctcca | 780 |
| gccttggtgg | tgacatcaat | gaacaacacc | gatggacttc | aggaacttgc | ctgtggggc | 840 |
| ttaatttatt | gctgggagt | tgtgttcttc | aagagtgatg | gcatcattcc | atttgcccac | 900 |
| gccatctggc | acctgtttgt | ggccacggca | gctgcagtgc | attactacgc | catttggaaa | 960 |
| taccttacc | gaagtcctac | ggactttatg | cggcatttat | gaccaatctg | tactaattct | 1020 |
| ccaaaccagt | attatttcaa | ttatggcact | tgggagtggg | gtgagagcta | acattgcac | 1080 |
| agggaaagaa | aaaaataac | tgcactgact | ttatatcttt | tgaatataat | tactgtgaaa | 1140 |
| gtataaaggc | tgtgttctgg | aattttctgc | ctcacagcaa | ataaataagg | tagtgaatta | 1200 |
| attattcatt | ccattccact | atcatgaagg | actctgaata | gacttggcca | actgatgttt | 1260 |
| acaaaccaga | cttttatatt | ttaattttac | agattttact | acatgatttt | tctaaattac | 1320 |
| tatgtcaggt | tgtaaaagtc | agtgcaataa | caaaccttcc | ttttaagaa | gaaaattgtt | 1380 |
| tctattactt | tcccattcac | taggtaaaga | atcatggaca | gaacttacac | tactttttac | 1440 |
| catgtttcat | cttggcataa | catgttctt | ttttaaatag | aaactttagt | tttttgtaaa | 1500 |
| ttttaaaaa | aatatttcat | tgatatgcat | ctctgcaggt | cctcattcat | gttgtaaatt | 1560 |
| tttgcagcaa | gcagtcaaca | ttccacaaac | gaacaaacat | tatacctctt | ctgatagttt | 1620 |
| tattaagcat | ggagaaattg | ccaattttta | aaaactgcag | ttttccaaac | ttttctgcca | 1680 |
| acctcttact | ctgaattcag | tgctgctttg | ggacatatac | ttgacctagc | ttggtttacc | 1740 |
| agtgatggaa | aagtattttg | atatcattaa | cttttcaaa | agatccaact | ttttctctat | 1800 |
| gcctttgcca | cattctcttc | agggtctctt | tccacagtgg | ataaatgttt | tttctgtatt | 1860 |
| atgacagtat | tgttgtgatg | gccatctgct | ggaaactcct | gaagagcatt | atgtattaca | 1920 |
| gtgagcagtt | gtattgcctg | tttggtgccc | aatggttaag | tcattgtcac | ttagctttat | 1980 |
| attgtcagtt | tgatatttat | tttaaattgt | ggaactagat | gcataaattc | acatttctgc | 2040 |
| ctttcctttg | catcttctca | tatattgtgt | ttttttttt | tttcctaga | aaaatatttt | 2100 |
| aaagcattgt | ttgacaggta | gaaactcatg | tatctgtagt | ccatgagtta | tatcctggct | 2160 |

```
cagtggagtg atatttatgt attattttta cttttctctc agtgtcttat attaagatta    2220
acatgttgtt aatagttgct tgttgatta  atctctcttg ttggtgtttt aataaatgaa    2280
ataggcttgc ctttagatcg ggtgctgata ttgcctgttt cctagtaatg ggctgatcaa    2340
atgatcagtg gaattcttgg tttgatgata accttattaa ttgaaatttt ttactgatgt    2400
ggctttaaaa gaggtttatt ttgtatatgt ttagaactct ctgattttga tgaattatat    2460
gggaatgaga aacagaagaa gtggtatttg ctggcgagtt aaataggcaa ggtacccagt    2520
gataacacca accaaaccac tcctatctgc atgattctga acatctggat gcctgttgtt    2580
ttactgtgta tattttattt ttaatatatt aactttgtgg attcatttaa ggtctactca    2640
aaagtaacac tgtcaaaacc actaatatgt atgtaaaaat tgtgctgtat actacaataa    2700
agttgttact tggatttgtt cca                                            2723

<210> SEQ ID NO 8
<211> LENGTH: 2947
<212> TYPE: DNA
<213> ORGANISM: Homo sapiens

<400> SEQUENCE: 8 atgggggggcg gagccgaggc ctccgaagcg gaagtgggtt gctgttgagg cggcggcatc      60
tttctcgagg agctctcctg gcggctgaa  gaaggagctt cttctccgga gtgcgccggc     120
ggtggcgcct gcggacctaa ctagctccag gttaggccga gctttgcggg aaagcagcgg     180
acttgaaaat actggaaatc tgtccggatc caaattattt tgcaagccag atgagtaacc     240
agagggcatg aaaggttgag aacatttgac ttccctgcaa accttggtat agatcacttc     300
cttttctgta ggaaaggaaa ggcaccaaag agcacaatga gtacaagaaa gcgtcgtggt     360
ggagcaataa attctagaca agctcagaag cgaactcggg aagcaacctc cacccccgag     420
atctccttgg aagcagaacc catagaactc gtggaaactg ctggagatga aattgtggac     480
ctcacttgtg aatctttaga gcctgtggtg gttgatctga ctcacaatga ctctgttgtg     540
attgttgacg aaagaagaag accaaggagg aatgctagga ggctgcccca ggaccatgct     600
gacagctgtg tggtgagcag tgacgatgag gagttgtcca gggacagaga cgtatatgtg     660
actacccata ctcccagaaa cgccagggat gagggcgcta caggcctcag gccctcaggt     720
actgtcagtt gtcccatctg catggacgga tactcagaga tcgtgcagaa tggacgtctc     780
atcgtttcca cagaatgcgg ccatgtcttc tgtagccagt gcctccgtga ttccctgaag     840
aatgctaata cttgcccaac ttgtaggaaa aagatcaacc acaaacggta ccaccccatt     900
tatatatgaa gtattcagag cccccccagga gagacggatg gacagacaga cagccaggtt     960
ctccagtggt atctgcctcc attttcctga gatcaaaaag actgtttcga aaccaacatc    1020
tgatatgtaa actgctcttt tgtttccaac cccttccttt tgttatctcc agtttgatgc    1080
tatggcgctg gacccagggc cctcccaggc catctctgtt cctctggggt ggtccagttc    1140
tagagtggga gaaagggagt caggcgcatt gggaatcgtg gttccagtct ggttgcagaa    1200
tctgcacatt tgccaagaaa ttttccctgt ttggaaagtt tgcccagct  ttccgggca     1260 caccacctt  tgtcccaagt gtctgccggt cgaccaatct gcctgccaca cattgaccaa    1320
gccagacccg gttcacccag ctcgaggatc ccaggttgaa gagtggcccc ttgaggccct    1380
ggaaagacca atcactggac ttcttccctt gagagtcaga ggtcacccgt gattctgcct    1440
gcaccttatc attgatctgc agtgattct  gcaaatcaag agaaactctg cagggcactc    1500
```

-continued

```
ccctgtttcc taagaacgaa aaagtgcaat aaaggccatt cgttacctac ttttcagcag    1560
cccacaagat gtagcactat tagtgtcccc ctcagaggct taatgttgcc tgtggagcag    1620
tgcccatccc agcccgtttc tgcccaccag ttgttctcag gaaccttacc catgctccag    1680
cgtccttcac ctggcacagg acatgcaaga taaatagggc aggcacgtgt ttgggtgtcc    1740
tctcttttct gataaaatcc atcccgtgtt tgccacacgc cctccagtcc tcagttccca    1800
ctgcctaacg tctgccccg tgtagatact gagaggtggt ggcagtaatt gtggccttat     1860
cagccgctca gttccaggct tttgcccagg tcactgttgc cccatgttcg gagaacctgg    1920
cccacctgtc ttggctttct catccttccc aacccagtgc cgtttatttc agaagcttcc    1980
tggccactgg gcttggatgc ttcgggcttc tgactgctcc ataggttttg actggtgaaa    2040
caggggccca gatgacaacc tctccttcgc tccacaggta cgcgggagcc tcaggttctc    2100
tcagggcag caaagtggcc caagctgccc ctgacagcac agggcctggg gggtggctaa     2160
cgagagaggc cttacagtgc cggcatgcct cctcttccac tgtcgtcctt cctcagaggg    2220
cctcacgcca aacaaacggc cttttcgtgt gaaacatctt cagggcggga aaggggccac    2280
ttctggcttt gttagcaata actgaccttc agtttaccct tctgaaggag cagggactca    2340
gcacagaatt cactttagac ggggctgaag gagtgtccct cctctatgtg aaaagaaaat    2400
tgttttattc ttcattctga cttttaact gtttggctca cttccagtta gtttgaatga     2460
aaataataat tttctacttg gagttgaaga gggcagaatc cgcagctctc atcattgtga    2520
tgtgtagcat gtctgccctc tgactggaca tcattgccat taactttctt ctgggcatca    2580
cggcaatgtc acgatgccca gacttggagc aaggcaacct tggagtcagt ccactcataa    2640
aatatggtaa cacccatttt aaaatttaag ttttgtcctt aaagacaact tcagtggtta    2700
attataaaag ttgtgttact tcgtcctaaa ttaaattgat agaaagattt aaaaatgtgt    2760
tttgtttcta ctattcagaa actgcgaact agggaaaggt tggtatgaag aaatgtcttt    2820
ccttttttca atgtacatag ttcaactctt tctttgttac atttaaacta tatccatgga    2880
tatcagtctg ctttggactc ctctgctagt gttacagatg gaaataaaac cattaatttg    2940
aaccaaa                                                              2947
```

<210> SEQ ID NO 9
<211> LENGTH: 2842
<212> TYPE: DNA
<213> ORGANISM: Homo sapiens

<400> SEQUENCE: 9

```
gagacgctcg ctgtttgtat ccattgagga gctgcctcgc gcaggggtg tgcgaggctg      60
agtccaagag atagcaaatc gagtcttaaa taatccgggg agaaagacgc ccgggtagat    120
ttgaggtgca gccttggagg gagggattag aagccgctag acttttttc ctcccctctc     180
agtagcacgg agtccgaatt aattggattt cattcactgg ggaggaacaa aaactatctg    240
ggcagcttca ttgagagaga ttcattgaca ctaagagcca gcggctgcag ctgggtgcag    300
agagaacctc cggctttact tctgtctcgt ctgccccaac cgctagcctc ggcttgggta    360
aggcgaggcg gaattaaacc ccgctccgag agcggcagct tcgcgcgcgg tgcgctcggc    420
ctatgcctgc cccgaggggc gtctggtagg caccccgccc tctcccgcag ctcgaccccc    480
atgatagata cgctcagacc cgtgcccttc gcgtcggaaa tggcgatcag caagacggtg    540
gcgtggctca acgagcagct ggagctgggc aacgagcggc tgctgctgat ggactgccgg    600
ccgcaggagc tatacgagtc gtcgcacatc gagtcggcca tcaacgtggc catcccgggc    660
```

```
atcatgctgc ggcgcctgca gaagggtaac ctgccggtgc gcgcgctctt cacgcgcggc    720
gaggaccggg accgcttcac ccggcgctgt ggcaccgaca cagtggtgct ctacgacgag    780
agcagcagcg actggaacga gaatacgggc ggcgagtcgg tgctcgggct gctgctcaag    840
aagctcaagg acgagggctg ccgggcgttc tacctggaag gtggcttcag taagttccaa    900
gccgagttct ccctgcattg cgagaccaat ctagacggct cgtgtagcag cagctcgccg    960
ccgttgccag tgctggggct cggggggcctg cggatcagct ctgactcttc ctcggacatc   1020
gagtctgacc ttgaccgaga ccccaatagt gcaacagact cggatggtag tccgctgtcc   1080
aacagccagc cttccttccc agtggagatc ttgcccttcc tctacttggg ctgtgccaaa   1140
gactccacca acttggacgt gttggaggaa ttcggcatca agtacatctt gaacgtcacc   1200
cccaatttgc cgaatctctt tgagaacgca ggagagttta aatacaagca aatccccatc   1260
tcggatcact ggagccaaaa cctgtcccag ttttcccctg aggccatttc tttcatagat   1320
gaagcccggg gcaagaactg tggtgtcttg gtacattgct tggctggcat tagccgctca   1380
gtcactgtga ctgtggctta ccttatgcag aagctcaatc tgtcgatgaa cgatgcctat   1440
gacattgtca aaatgaaaaa atccaacata tcccctaact tcaacttcat gggtcagctg   1500
ctggacttcg agaggacgct gggactcagc agcccatgtg acaacagggt tccagcacag   1560
cagctgtatt ttaccacccc ttccaaccag aatgtatacc aggtggactc tctgcaatct   1620
acgtgaaaga ccccacaccc ctccttgctg gaatgtgtct ggcccttcag cagtttctct   1680
tggcagcatc agctgggctg ctttctttgt gtgtggcccc aggtgtcaaa atgacaccag   1740
ctgtctgtac tagacaaggt taccaagtgc ggaattggtt aatactaaca gagagatttg   1800
ctccattctc tttggaataa caggacatgc tgtatagata caggcagtag gtttgctctg   1860
tacccatgtg tacagcctac ccatgcaggg actgggattc gaggacttcc aggcgcatag   1920
ggtagaacca aatgataggg taggagcatg tgttctttag ggccttgtaa ggctgtttcc   1980
ttttgcatct ggaactgact atataattgt cttcaatgaa gactaattca attttgcata   2040
tagaggagcc aaagagagat ttcagctctg tatttgtggt atcagtttgg aaaaaaaaat   2100
ctgatactcc atttgattat tgtaaatatt tgatcttgaa tcacttgaca gtgtttgttt   2160
gaattgtgtt tgttttttcc tttgatgggc ttaaagaaaa ttatccaaag ggagaaagag   2220
cagtatgcca cttcttaaaa cagaacaaaa caaaaaagaa aaattgtgct cttttctaat   2280
ccaaagggta tatttgcagc atgcttgact ttaccaattc tgatgacatc tttacggaca   2340
ctattatcac taagacccttg ttatggcgaa gtctttagtc ttttttcatgt attttcctca   2400
tgattttttc tctttatgta gtttgactat gccttacctt tgtaaatatt tttgcttgtg   2460
ttgtcgcaaa ggggataatc tgggaaagac accaaatcat gggctcactt taaaaaaaga   2520
aagaataaaa aaaccttcag ctgtgctaaa cagtatatta cctctgtata aaattcttca   2580
gggagtgtca cctcaaatgc aatactttgg gttggtttct ttcctttaaa aaaatttgta   2640
taaaactgga agtgtgtgtg tgtgagcatg ggtacccatt tgataagaga aatgcatttg   2700
attgtgaaga agggagagtt aaattctcca ttatgttcgt ggtgtaaagt ttagagctgg   2760
aatttattat aagaatgtaa aaccttaaat tattaataaa taactatttt ggctattgaa   2820
aaaaaaaaaa aaaaaaaaaa aa                                            2842
```

<210> SEQ ID NO 10
<211> LENGTH: 7769
<212> TYPE: DNA

<213> ORGANISM: Homo sapiens

<400> SEQUENCE: 10

```
tttccagctg gttgtcattt cactcggctc ggtcctgagg agaaggactc agccgcggct      60
gcgggacccg ggcaccggga ggcggtggcg gcggcggcgg cggcagcagc ggcgacagca     120
gaggaggaag aggaggaaga aggaaagaaa aagaagaacc aggaggagtc ctcaacaacg     180
acagcgggga ctgcgggacc agggtaaagc ggcgacggcg gcgacggccc agcaaccgtg     240
aggagaaaca aaagccttct aaattatagt ttaaaaaaaa attctggggg aaaagagaga     300
gaaagccgag gggggaggcc cttctccttt aaaataacta cggtagtggg ttttcctttttt   360
ttttcctctt ttttccctct ctgcggagaa tcgaactgag ggaactgaac aaaccgcccc     420
tgggtcccat gagggaaaaa accccggag ccgcagagag gggaagaggc agaaccgca      480
ggaccttcca ggtcgccccc tcggtccccg cacccccagg ccgcccgctc accctcgtcg     540
agtctcgcta atccctcctg atcgcgaccc ccgcaagagg gagaaacggg tgtttccaac     600
cccctttcatg ggggagagga agccgcgggg agccaggaa cagcgaccgc agcaagatct     660
gcacccggag cctcaggaac agccccagag gccaaaactg caccctgcga aagagcagaa     720
aacaggacca ggaacagcag aaacctccct gcaatcatct ttccattagt caatgctgat     780
ttcctctccc gaaaccagga attcacttcc cacccagat aacctaatat aatctatata     840
tataaatata taatatataa tgttcttaaa ttattcctga tttttttttta accaagctgc     900
caagaaaaga acgtattccc ctcttagtcc tattctaatt tttatgtgag tgaatctaaa     960
ctgctgagga aaaccatatg tgattgttaa attatatata tctatatttt tactccgcgc    1020
aaggcttatt cttctacatc catagatgct tgagaagctc tgttttttgtc attcatgtac    1080
attttccttt ggaaaagaa agcgccatt ttactaacca aagacttgat ttttacccctc    1140
ttcatttta ttccctccta aaaataagcc caattggatc caagtcaatg ttttaagaga    1200
tttttttaag agttgttttt tctttcagag accagaattc caaatcagaa caatttaagg    1260
tgataagctg cgatctttga gctagctata aataagacat ttcaagcaag caagcaaaca    1320
acttaaattt ggggtagagg aaaaaaaagg cgtgagacat caggttgtca ttttttattg    1380
tgagattctg ctcctaaaga taataaatgg gggattacgg gtttggagtg ctagtgcaaa    1440
gcaatactgg gaataaatct gcttttccag tcagattcca tccacatctg cagcctccac    1500
accatcacca aaatgccacc cccagccctg ctgcttttat aaataataac acagctgcca    1560
atggcagcag tgctgggtca gcttggcttt ttcctgctcc agctacccat aacattcagg    1620
atgagatctt ggggtcagaa aaagcaaaaa gtcagcaaca ggaacagcaa gaccccttag    1680
aaaagcagca gctttccca gtccaggtc aggaagctgg aatactgcct gaaacagaga     1740
aggcaaaatc agaagaaaat caaggggaca attcttcgga aaatggcaat gggaaggaga    1800
aaataaggat cgaatctcca gtgttgacag ggtttgatta tcaagaagcc actgggctag    1860
gtacttcaac ccaaccttg acatctagcg catcgtctct tactggtttc agtaactggt    1920
cagcagcgat agcgccttcc tcctctacaa taatcaatga agatgcaagt ttctttcacc    1980
agggaggggt ccctgctgct tcggctaata acgtgctct gttgtttcaa aatttccccc    2040
atcatgtcag ccctggcttt ggaggcagct tctctcctca gatcgggcct ctctcacagc    2100
accacccaca tcaccctcat ttccagcatc atcacagcca gcatcagcag caaaggaggt    2160
ctcctgccag tccccatccc ccacccttca cacatagaaa tgctgctttt aaccagctgc    2220
ctcatttggc gaataatctt aacaaacccc cctctccgtg gagcagctac cagagtccgt    2280
```

```
caccaacacc ctcctcttcc tggagcccgg gcggtggtgg atatggtggc tggggaggtt    2340
cccaaggccg agatcaccgc agagggctga atggtggaat aacgccctg  aactccatct    2400 cgcctttgaa gaaaaatttt gcaagcaatc atattcagct ccagaagtat gctcgcccca    2460
gctctgcctt tgcacctaaa tcctggatgg aagatagctt gaacagggct gacaacattt    2520
ttccttttcc ggatcgcccc aggacattcg acatgcactc actggagagt tcactcattg    2580
acataatgag agctgaaaat gataccatta aaggtcgtct aaactattca tatccaggat    2640
ccgatagctc tctgcttatt aatgcaagga catatgggcg aaggagaggt cagtcttcac    2700
tgtttccaat ggaagatgga ttcttggatg atggccgtgg ggatcagcct cttcatagtg    2760
gcctgggttc acctcactgc ttcagtcacc agaatgggga agagtggaa  cgatattctc    2820 gaaaggtgtt tgtaggcgga ttgcctccag acattgatga agatgagatc acagctagtt    2880
ttcgtcgctt tggccctctg attgtggatt ggcctcataa agctgagagc aaatcctatt    2940
ttcctcctaa aggctatgca ttcctgctgt ttcaagatga aagctctgtg caggctctca    3000
ttgatgcatg cattgaagaa gatggaaaac tctacctttg tgtatcaagt cccactatca    3060
aggataagcc agtccagatt cggccttgga atctcagtga cagtgacttt gtgatggatg    3120
gttcacagcc acttgaccca cgaaaaacta tatttgttgg tggtgttcct cgaccattac    3180
gagctgtgga gcttgcgatg ataatggatc ggctatatgg aggtgtgtgc tacgctggga    3240
ttgataccga ccctgagcta aaatacccaa aaggagctgg gagagttgcg ttctctaatc    3300
aacagagtta catagctgct atcagtgccc gctttgttca gctgcagcat ggagagatag    3360
ataaacgggt ggaagttaag ccatatgtct tggatgatca gctgtgtgat gaatgtcagg    3420
gggcccgttg tgggggggaaa tttgctccat ttttctgtgc taatgttacc tgtctgcagt    3480
attactgtga atattgctgg gctgctatcc attctcgtgc tggcagggaa ttccacaagc    3540
ccctggtgaa ggaaggcggt gaccgccctc ggcatatttc attccgctgg aactaaagga    3600
taactgcagt gctcatttc  aggcctcaga ataagtgcac tcttctgttc attctgaccc    3660
cttcctcaac ctcttcacgc tggcatgtcc ttttgtagca gtctgtaact taactatagt    3720
ataatgaaaa gaatgaccta taatataggt gttttgtaga ttcttgtgtc actgcaaaca    3780
atatgaactc cttttcgta  ttgccatcgg gttgcatgga agttttattc tcttgttttg    3840
ctggaaacca agaggatcca aacttcctgc aacattttct tagaggagag agagaaatat    3900
taaaagagaa atgaaacaat agagtatttt gggttttaa  ttaaattatt gttaataata    3960
taacatataa gaatactttt attaaaataa ccatgcaaca ataacactat cggtctatct    4020
gacagttttt cccccaggga agtgcttttg ccttttcctt tctttttttt tttttttca     4080 tcttttttgt ctctctcttt tttccatccc ttttaatttt tttaacagc  aatggaggaa    4140 gttaacaatt tttaatggaa agagcatgtt agagcaaaca aatgcataag caagactgag    4200
cagcattata attaatttc  agggttttga ggctgaacat aatttcatta tccctcaaaa    4260
agttaccacc acatcagaaa aaataaaaaa aaaatagtaa agtaggcaga gctaggttta    4320
ttttctctta aacaattttt aaaattcaga atgtaaaaat tgggtaaatt tactactgag    4380
gggagtgcac ttatttattt aacttactta tctggtcaaa gccccaggaa acctaccaaa    4440
gctagaatta atgacaactg gtgggaaacc tagcatttcc tctcctgaag aataaatgta    4500
taaatgttat ttttgatgtt tatatataaa ctctatatcc taatttacta atactcatca    4560
gatgtcagcc tttgctctcc attttgacgt taaaaaacaa caacagatct agagatacct    4620
```

-continued

```
caaggatatc attttttgatt tgtgttaca gtacacttgt agccaaaact ggaagacaaa        4680
accaatatat aatttggctg ctgattggct tactttagga tttaaagtta ctttgggtat        4740
cctgtaattt agttgtaaca tagaaaatga aaaaacagtt aaaaaaagtg aagtagttgc        4800
aaagtgtttt gcactgttga actaagtaac tgtgtaaatc tgtgcaaagg tacgtatgtt        4860
tatcttactc ttcctataaa ctaaaataac attacagttt ccgaatttag catgggacat        4920
agtcagtgtt tgaagtgcca acttcatcaa gtaatgcatg ctttattata aataaaattc        4980
tagctttgaa aggcgttatg tgttgaacag tatgcttcag gggtaaattt aaaatagtct        5040
cttgaagccc tagtcatgga agtaactttt attttaattg acattctctt attaaatgcc        5100
ctatccatca ttaaaaggtt tattatcagt gggcaaaaca tgaaataata tgatcgaatg        5160
gcaatcttgc tagttgcgct acctaacagt accatcttgg atccttcaaa accaaagact        5220
tgccccagca ctgctgtgga accacctggc ttatgacccc tatggatgat ctttaggaaa        5280
agcagccctt tactttttaat acaggcttta atgaactata cctgttaagt tccaaaggtc        5340
aaaatggagg catttgctgt ctaatattca aacatagaaa gggagctgct tttaaagaat        5400
tccctgcaaa tactgaaagc agtcatgcga atggagggtg ctcttgtgta gctggtcagg        5460
gacttttttt tctttttctcc tgaactacat gattctaatt ggaatgttca tttgcctctt        5520
tttactcttt taaatgcttg taggtggctt ggggtgtgct atcgtgctgt tcctactcag        5580
taaacaggtg tgatgagtta acaagaaata acactgtttg agaactagct ttgaataata        5640
atttttccct ttgtacatga cctgctgaat ttcggtacag tgttttttgta gctaacttat        5700
tttgtcatgc acataatgta tatttgttat gcactacttt tgtatatctt gttttttccaa       5760
cagtgaacat ttttaggcac acttttcact gacgggatat ctctttatgc aatacctcaa        5820
tttttcatat tgcaaagagt agcttttttgt actttttatta ctgagagatc ttcatatact      5880
tcattttttta atataaataa ttttaataaa ttttatttttc ttatattctg cttttttatac     5940
atttcagtgc tctgcataca ttttaaatta tgaatgtcgt gcactggcaa tgctattttta       6000
gagtctgcag agaagagaaa gcatgttgct taaacatcct tccccagcac cagctattgg        6060
tgtacctata atttaagaaa tagtctatgt aaagtcacaa attaatgaaa aaaattcgca        6120
tgaaaatgac agataacact gtagttccta aaaaaaaaat taaatgcata agcataaggt        6180
agaaattaaa ataacaaaat tgtctacagc ttcttactaa gttttttaaaa ttattcataa       6240
aatgcagaca ttttttggtga atgtttagcc attttttaata ttaataaatt gatgttaagt      6300
gtttgattca gagatgtctg ctctttttaaa ttatatataa ggaaaaaaaa tagcctgcct       6360
tgggacaggt gtgtaatgtt agtgtgcatg actaatgtaa gaaattgtta ttctactaat        6420
atttacttgt gattgtgtga caagtgtgtt tacagattat tggttacact tcaatttaca        6480
gggcataaac aatgattatc tattactctg aactttatga ttacatgttc ttcagattac        6540
atgggattgt agtggggagt taccatgtaa ctcaaacata attaacatgt aattagttta        6600
cagattgtag ggcatcactt caattcacca agcatgtagt tctagcgcac tagcatggcg        6660
ccagccatgt acttacaatg tagttacaga gtaattacat ggtgattttt gcaatgtaaa        6720
ataaagtgtt tctgattatt ttctatgtaa aggaaccctc tcctttcccc ttctggtccc        6780
tgcgctttgg tataatatat atacttctcc atacacagac ctctgcagaa tgcaaaataa        6840
aacttgcagt gaatgaattt agcatttttat gagagtgctg ttggaaagac ttgataattc       6900
accccttttg ttttgaagag ttgaatcttc tgttaaaagg tgatttaaaa cttgaatgtg        6960
atgaattgtg gcaagttaac ttcaagttat gtgcaatact tatttcaaac ttttgaaaga        7020
```

```
tctttgcagt gtaattcttt gttttaatt gcagacattt aaaaatgtca ttttctactg    7080
ttaagagtaa tcctcttct tgctggtgtt tctaaagaaa agaatcagaa atcaatcttt    7140
ctactaatgt aaatttgaga ttatttttaa aaatggaata aaagaggttt tggtcatttg    7200 ctttattta ttatttaaa gctactgtga ttgatagcat tgtaagaatc gggacaatat     7260
tgtattcaac tgttttattt tttatatttt taaaatttaa agtataatta gttttatt aa  7320 ttttcatcag attttgtta tatttttgg aagtgaaact tttagcaagt gggtgtctag     7380
tttttactaa tccctaattt tttttccagt gtattgctca tattatcaga aggaaaagtt   7440
atttaagtat gtcagttaat tgtactactt ggctgaattt ccatatagtt tttactgtgt   7500
atggggaggt tgtagtattt attatagcat tttaaataag ggtaattcat tttttattaa   7560
agtcattttc acgttaagtt cctatttttg tatgttctac tcttaagtta tataacacag   7620
ttcctttttt aaaagagttc atttgttgaa gtgctagtga aaaattaatg ttattaaata   7680
gtttgcaaat gactatttat accagtatgc atataatttt taaatatttg taatgtgaga   7740
tgttgaatga ataaaacttt taactcaga                                     7769

<210> SEQ ID NO 11
<211> LENGTH: 4232
<212> TYPE: DNA
<213> ORGANISM: Homo sapiens

<400> SEQUENCE: 11
aaaattgcgt ttgagtttgc cgcgagccgg gccaatcggt tttgccaacg catgcccacg      60
tgctggcgaa caaatgtaaa cacggagatc gtgtgccggg cacttggttt cgtggtgggc    120
aactgtgctg ctgtttctttt tggccgcgga caaggtcggc agaggtggac ccctgcttgg   180
gagagctctt ctcgctgtgc tgacacccgc ccctaacagt cacccacccc ggggaaataa    240
tggggctcgg aggcctcctc ccagccagtg tccagcctaa gcacatcggc tcccgcagtt    300
cagaaaggtc ccgaggcccg agtcaccatt tccggctcag acctcgaccc ggaacgtggc    360
tgcccactgc cacgcccact acgcccagt ggctcgcccc aggggacgag ggcaagaag     420 cggcctccga gggcagcggc cgaaggccat tcggtccctg ctcttccca gctcgcagag    480 acccggaagc gctgcccggc cgcctgcccc tcttcagatc ccccagcacc ggaggagcag   540 cgaggggct gcgtccaggc cggctttcgg gtcggcttag gcgaatccag ctctctttg     600 cccctcccag aaggcccagc cccgtccggg cggtgttcgg gcggcgccgg gccgggcccc   660
ccgccgcccc aggctcgctc ataggcccgg aacaccacag cccgcccaga cttggctggc   720
gccgagccgg gggtggagcc agcgggttcc cgccaaaatc gcgtagctgg tccttccccc   780
gcgggctacg tcgcgccctc cttttttttt caaacccgga gctgcactgg gattggtgga   840
ctgggcactc acgtggttaa cggtcgcggg aagccgcgga gcccgaacct gagactggac   900
ctgaggagac ctcagcctcg gtgctcgggc cgccccgcct ctgccggaaa gtccgcgccg   960
ccgctgccgc caccgtccgc agcccgagcg ccccggagcc gcaggccgcc gccgcgcaga  1020
gacgccgcgg ctgcgactag gcgcgcccag ccgcacgtgg cggaccccgcc ccaggcccg   1080 cagtgtcctg gaccccgcag gcctccgctc tcctgtcctc ggccccgtcc ccagggccga   1140
gatgagcttc ctgagccgac agcagccgcc gccaccccgc cgcgccgggg cggcctgcac   1200
cttgcggcag aagctgatct tctcgccctg cagcgactgt gaggaggagg aagaaggaga   1260
ggaggaggag ggcagcggcc acagcaccgg ggaggactcg gcctttcaag agcccgactc   1320
```

```
gccgctgccg cccgcgcgga gccccacgga gcccgggccc gagcgccgcc gctcgcccgg   1380
gccgcccccc gggagcccg gcgagctgga ggaggacctg ttgctgcccg cgcctgccc   1440 gggcgcggac gaggcgggcg gtggggcgga gggcgactcg tgggaggagg agggcttcgg   1500
ctcctcgtcg ccggtcaagt cgccggcggc cccctacttc ctgggtagct ctttctcgcc   1560
ggtgcgctgc ggcggcccag gagatgcgtc gccgcgggt tgcggggcgc gccgggcggg   1620
cgaaggccgc cgctcgccgc ggccggacca cccgggcacc ccgccacaca agaccttccg   1680
caagctgcga ctcttcgaca ccccgcacac gcccaagagt ttgctctcca aagctcgggg   1740
aattgattcc agctctgtta aactccgggg tagttctctc ttcatggata cagaaaaatc   1800
aggaaaaagg gaatttgatg tgcgacagac tcctcaagtg aatattaatc ctttactcc   1860 ggattctttg ttgcttcatt cctcaggaca gtgtcgtcgt agaaagagaa cgtattggaa   1920
tgattcctgt ggtgaagaca tggaagccag tgattatgag cttgaagatg aaacaagacc   1980
tgctaagaga attacaatta ctgaaagcaa tatgaagtcc cggtatacaa cagaatttca   2040
tgagctagag aaaatcggct ctggagaatt tggttctgta tttaagtgtg tgaagaggct   2100
ggatggatgc atttatgcca ttaagcgatc aaaaaagcca ttggcgggct ctgttgatga   2160
gcagaacgct ttgagagaag tatatgctca tgcagtgctt ggacagcatt ctcatgtagt   2220
tcgatatttc tctgcgtggg cagaagatga tcatatgctt atacagaatg aatattgtaa   2280
tggtggaagt ttagctgatg ctataagtga aaactacaga atcatgagtt actttaaaga   2340
agcagagttg aaggatctcc ttttgcaagt tggccgaggc ttgaggtata ttcattcaat   2400
gtctttggtt cacatggata taaaacctag taatatttc atatctcgaa cctcaatccc   2460
aaatgctgcc tctgaagaag gagacgaaga tgattgggca tccaacaaag ttatgtttaa   2520
aataggtgat ctgggcatg taacaaggat ctccagtcca caagttgaag agggcgatag   2580 tcgtttttctt gcaaatgaag ttttacagga gaattatacc catctaccaa aagcagatat   2640
ttttgcgctt gccctcacag tggtatgtgc tgctggtgct gaacctcttc cgagaaatgg   2700
agatcaatgg catgaaatca gacagggtag attacctcgg ataccacaag tgctttccca   2760
agaatttaca gagttgctaa aagttatgat tcatccagat ccagagagaa gaccttcagc   2820
aatggcactg gtaaagcatt cagtattgct gtccgcttct agaaagagtg cagaacaatt   2880
acgaatagaa ttgaatgccg aaaagttcaa aaattcactt ttacaaaaag aactcaagaa   2940
agcacagatg gcaaaagctg cagctgagga aagagcactc ttcactgacc ggatggccac   3000
taggtccacc acccagagta atagaacatc tcgacttatt ggaaagaaaa tgaaccgctc   3060
tgtcagcctt actatatact gagctactcc tttcccacct ccccctgaac actgtgacaa   3120
gaggaagcta ggttgaaatc actgatagaa tccagtttgc aattactttc tcgattggtg   3180
tcagtagttt tactgattag gactttatt gtgaattaca gttgaaagct gtattttgat   3240
gattgctatg tcaggctttc atctaatctt accagtctgt cttctgtagg atgtgtcact   3300
gttggatgtt acaccagcct ttccagggtt aaccactgtg gtggtgtgct gcttatagtt   3360
tgctgttgca ttgtaataaa aggtgtcttt ccctgtagtg acctgtaaaa agtactcaag   3420
ggctttatta cagacatacc ctcccttga aagggacat gctaaaagac tcattactac   3480
tcagccttca atgtacctgt gtgtccatct tatatttctt ttttttttt aattgtgaat   3540 tagacttgta tatcccactg ggagcacttt gtaggcattg catgaaccat gggatgatga   3600
ttctgtggag gtattgcctt gtgaatttgc tgctatttta gttttgtctt tgctgtaaac   3660
ttgtagcatt aaacaatcat tgttgttaat aggtcttctt tttgaaacaa ttatgtgaaa   3720
```

| | |
|---|---|
| tgtatagctg cttttgatga aaagcagcta tttgccttt ttttttttcc tttgaactt | 3780 |
| gaagctagtg cattggaaaa atgcaccctt tccctccttt ggaatgctgt attaatgtag | 3840 |
| tataataatt actggttttg taacttgttc tggtaatgtc cttcccggac tctttttaaa | 3900 |
| tgtctccccc taagttttat acttgattgt attattagtc tgtttttaaa tgttttgccc | 3960 |
| ggttttctc ttcaatattt gtgtatataa accgatcttc gtgatactgt acatagctgt | 4020 |
| ttgaaatgcc agaatgactt ctgacattcc aagttttca caaaatatat tttatctgtg | 4080 |
| attagccatt tgactaataa tactggctaa cagatgttga aaaaaattgt ctgtttgttt | 4140 |
| tctcattaat tttggtctaa aacatgttg cacttgtctt tgacttgtgt tttattaaca | 4200 |
| ttgattggca tattaaaagt cactctgagc tt | 4232 |

<210> SEQ ID NO 12
<211> LENGTH: 5314
<212> TYPE: DNA
<213> ORGANISM: Homo sapiens

<400> SEQUENCE: 12

| | |
|---|---|
| agtttcaccg ctcgatcttg ggacccaccg ctgccctcag ctccgagtcc agggcgagtg | 60 |
| cagagcagag cgggcggagg accccggcg cgggcgcgga cggcacgcgg ggcatgaacc | 120 |
| tggagggcgg cggccgaggc ggagagttcg gcatgagcgc ggtgagctgc ggcaacggga | 180 |
| agctccgcca gtggctgatc gaccagatcg acagcggcaa gtaccccggg ctggtgtggg | 240 |
| agaacgagga gaagagcatc ttccgcatcc cctggaagca cgcgggcaag caggactaca | 300 |
| accgcgagga ggacgccgcg ctcttcaagg cttgggcact gtttaaagga aagttccgag | 360 |
| aaggcatcga caagccggac cctcccacct ggaagacgcg cctgcggtgc gctttgaaca | 420 |
| agagcaatga ctttgaggaa ctggttgagc ggagccagct ggacatctca gacccgtaca | 480 |
| aagtgtacag gattgttcct gagggagcca aaaaggagc caagcagctc accctggagg | 540 |
| acccgcagat gtccatgagc caccctaca ccatgacaac gccttaccct tcgctcccag | 600 |
| cccagcaggt tcacaactac atgatgccac ccctcgaccg aagctggagg gactacgtcc | 660 |
| cggatcagcc acacccggaa atcccgtacc aatgtcccat gacgtttgga ccccgcggcc | 720 |
| accactggca aggcccagct tgtgaaaatg gttgccaggt gacaggaacc ttttatgctt | 780 |
| gtgccccacc tgagtcccag gctccggag tccccacaga gccaagcata aggtctgccg | 840 |
| aagccttggc gttctcagac tgccggctgc acatctgcct gtactaccgg gaaatcctcg | 900 |
| tgaaggagct gaccacgtcc agccccgagg gctgccggat ctcccatgga catacgtatg | 960 |
| acgccagcaa cctggaccag gtcctgttcc cctacccaga ggacaatggc cagaggaaaa | 1020 |
| acattgagaa gctgctgagc cacctggaga ggggcgtggg cctctggatg gccccgacg | 1080 |
| ggctctatgc gaaaagactg tgccagagca ggatctactg ggacgggccc tggcgctgt | 1140 |
| gcaacgaccg gccaacaaa ctggagagag accagacctg caagctcttt gacacacagc | 1200 |
| agttcttgtc agagctgcaa gcgtttgctc accacggccg ctccctgcca agattccagg | 1260 |
| tgactctatg ctttggagag gagttttcag accctcagag gcaaagaaag ctcatcacag | 1320 |
| ctcacgtaga acctctgcta gccagacaac tatattattt tgctcaacaa aacagtggac | 1380 |
| atttcctgag gggctacgat ttaccagaac acatcagcaa tccagaagat taccacagat | 1440 |
| ctatccgcca ttcctctatt caagaatgaa aaatgtcaag atgagtggtt tctttttcc | 1500 |
| ttttttttt tttttttttg atacggggat acggggtctt gctctgtctc ccaggctgga | 1560 |

```
gtgcagtgac acaatctcag ctcactgtga cctccgcctc ctgggttcaa gagactctcc    1620
tgcctcagcc tccctggtag ctgggattac aggtgtgagc cactgcaccc acccaagaca    1680
agtgattttc attgtaaata tttgacttta gtgaaagcgt ccaattgact gccctcttac    1740
tgttttgagg aattcagaag tggagatttc agttcagcgg ttgaggagaa ttgcggcgag    1800
acaagcatgg aaaatcagtg acatctgatt ggcagatgag cttatttcaa aaggaagggt    1860
ggctttgcat ttcttgtgtt ctgtagactg ccatcattga tgatcactgt gaaaattgac    1920
caagtgatgt gtttacattt actgaaatgc gctctttaat ttgttgtaga ttaggtcttg    1980
ctggaagaca gagaaaactt gcctttcagt attgacactg actagagtga tgactgcttg    2040
taggtatgtc tgtgccattt ctcagggaag taagatgtaa attgaagaag cctcacacgt    2100
aaaagaaatg tattaatgta tgtaggagct gcagttcttg tggaagacac ttgctgagtg    2160
aaggaaatga atctttgact gaagccgtgc ctgtagcctt ggggaggccc atccccccacc   2220 tgccagcggt ttcctggtgt gggtccctct gccccgccct ccttcccatt ggctttctct    2280
ccttggcctt tcctggaagc cagttagtaa acttcctatt tcttgagtc aaaaaacatg     2340 agcgctactc ttggatggga cattttgtc tgtcctacaa tctagtaatg tctaagtaat     2400
ggttaagttt tcttgtttct gcatcttttt gaccctcatt ctttagagat gctaaaattc    2460
ttcgcataaa gaagaagaaa ttaaggaaca taaatcttaa tacttgaact gttgcccttc    2520
tgtccaagta cttaactatc tgttccctc ctctgtgcca cgctcctctg tttgtttggc     2580
tgtccagcga tcagccatgg cgacactaaa ggaggaggag ccggggactc ccaggctgga    2640
gagcactgcc aggacccacc actgaagca ggatggagct gactacggaa ctgcacactc     2700
agtgggctgt ttctgcttat ttcatctgtt ctatgcttcc tcgtgccaat tatagtttga    2760
cagggcctta aaattacttg gctttttcca aatgcttcta tttatagaat cccaaagacc    2820
tccacttgct taagtatacc tatcacttac attttttgtgg ttttgagaaa gtacagcagt   2880
agactggggc gtcacctcca ggccgttct catactacag atatttact attactccca     2940 ggatcagcag aagattgcgt agctctcaaa tgtgtgttcc tgcttttcta atggatattt    3000
taaattcatt caacaagcac ctagtaagtg cctgctgtat ccctacatta cacagttcag    3060
cctttatcaa gcttagtgag cagtgagcac tgaaacatta ttttttaatg tttaaaaagt    3120
ttctaatatt aaagtcagaa tattaataca attaatatta atattaacta cagaaaagac    3180
aaacagtaga gaacagcaaa aaaataaaaa ggatctcctt ttttcccagc ccaaattctc    3240
ctctctaaaa gtgtccacaa gaaggggtgt ttattcttcc aacacatttc acttttctgt    3300
aaatatacat aaacttaaaa agaaaacctc atggagtcat cttgcacaca ctttcatgca    3360
gtgctctttg tagctaacag tgaagattta cctcgttctg ctcagaggcc ttgctgtgga    3420
gctccactgc catgtaccca gtagggtttg acatttcatt agccatgcaa catggatatg    3480
tattgggcag cagactgtgt ttcgtgaact gcagtgatgt atacatctta tagatgcaaa    3540
gtattttggg gtatattatc ctaagggaag ataaagatga tattaagaac tgctgtttca    3600
cggggccctt acctgtgacc ctctttgctg aagaatattt aaccccacac agcacttcaa    3660
agaagctgtc ttggaagtct gtctcaggag caccctgtct tcttaattct ccaagcggat    3720
gctccatttc aattgctttg tgacttcttc ttctttgttt ttttaaatat tatgctgctt    3780
taacagtgga gctgaatttt ctggaaaatg cttcttggct ggggccacta cctcctttcc    3840
tatctttaca tctatgtgta tgttgacttt ttaaaattct gagtgatcca gggtatgacc    3900
tagggaatga actagctatg aaatactcag ggttaggaat cctagcactt gtctcaggac    3960
```

```
tctgaaaagg aacggcttcc tcattccttg tcttgataaa gtggaattgg caaactagaa    4020
tttagtttgt actcagtgga cagtgctgtt gaagatttga ggacttgtta aagagcactg    4080
ggtcatatgg aaaaaatgta tgtgtctccc aggtgcattt cttggtttat gtcttgttct    4140
tgagattttg tatatttagg aaaacctcaa gcagtaatta atatctcctg aacactata     4200 gagaaccaag tgaccgactc atttacaact gaaacctagg aagcccctga gtcctgagcg    4260
aaaacaggag agttagtcgc cctacagaaa acccagctag actattgggt atgaactaaa    4320
aagagactgt gccatggtga gaaaaatgta aaatcctaca gtgaaatgag cagcccttac    4380
agtattgtta ccaccaaggg caggtaggta ttagtgtttg aaaaagctgg tctttgagcg    4440
agggcataaa tacagctagc cccaggggtg aacaactct gggagtcttg ggtactcgca     4500
cctcttggct tgttgatgc tccgccagga aggccacttg tgtgtgcgtg tcagttactt     4560
ttttagtaac aattcagatc cagtgtaaac ttccgttcat tgctctccag tcacatgccc    4620
ccacttcccc acaggtgaaa gttttctga aagtgttggg attggttaag gtctttattt      4680
gtattacgta tctcccgaag tcctctgtgg ccagctgcat ctgtctgaat ggtgcgtgaa    4740
ggctctcaga ccttacacac cattttgtaa gttatgtttt acatgccccg ttttgagac     4800 tgatctcgat gcaggtggat ctccttgaga tcctgatagc ctgttacagg aatgaagtaa    4860
aggtcagttt ttttttgtat tgattttcac agctttgagg aacatgcata agaaatgtag    4920
ctgaagtaga ggggacgtga gagaagggcc aggccggcag gccaacccctc ctccaatgga   4980 aattcccgtg ttgcttcaaa ctgagacaga tgggacttaa caggcaatgg ggtccacttc    5040
cccctcttca gcatccccccg tacccccactt tctgctgaaa gaactgccag caggtaggac  5100
cccagaggcc cccaaatgaa agcttgaatt tcccctactg gctctgcgtt ttgctgagat    5160
ctgtaggaaa ggatgcttca caaactgagg tagataatgc tatgctgtcg ttggtataca   5220
tcatgaattt ttatgtaaat tgctctgcaa agcaaattga tatgtttgat aaatttatgt    5280
ttttaggtaa ataaaaactt ttaaaaattt gtta                                5314

<210> SEQ ID NO 13
<211> LENGTH: 4451
<212> TYPE: DNA
<213> ORGANISM: Homo sapiens

<400> SEQUENCE: 13
gctcatacta gggacgggaa gtcgcgacca gagccattgg agggcgcggg gactgcaacc      60
ctaatcagca gagcccaaat ggcgcagtgg gaaatgctgc agaatcttga cagcccctttt    120 caggatcagc tgcaccagct ttactcgcac agcctcctgc ctgtggacat tcgacagtac     180
ttggctgtct ggattgaaga ccagaactgg caggaagctg cacttgggag tgatgattcc     240
aaggctacca tgctattctt ccacttcttg gatcagctga actatgagtg tggccgttgc    300
agccaggacc cagagtcctt gttgctgcag cacaatttgc ggaaattctg ccgggacatt    360 cagcccttttt cccaggatcc tacccagttg gctgagatga tctttaacct ccttctggaa    420
gaaaaaagaa ttttgatcca ggctcagagg gcccaattgg aacaaggaga gccagttctc    480
gaaacacctg tggagagcca gcaacatgag attgaatccc ggatcctgga tttaagggct    540
atgatggaga agctggtaaa atccatcagc caactgaaag accagcagga tgtcttctgc    600
ttccgatata gatccaggc caaagggaag acaccctctc tggacccca tcagaccaaa      660 gagcagaaga ttctgcagga aactctcaat gaactggaca aaaggagaaa ggaggtgctg    720
```

```
gatgcctcca aagcactgct aggccgatta actaccctaa tcgagctact gctgccaaag    780
ttggaggagt ggaaggccca gcagcaaaaa gcctgcatca gagctcccat tgaccacggg    840
ttggaacagc tggagacatg gttcacagct ggagcaaagc tgttgtttca cctgaggcag    900
ctgctgaagg agctgaaggg actgagttgc ctggttagct atcaggatga ccctctgacc    960 aaagggtgg acctacgcaa cgcccaggtc acagagttgc tacagcgtct gctccacaga    1020
gcctttgtgg tagaaaccca gccctgcatg ccccaaactc cccatcgacc cctcatcctc    1080
aagactggca gcaagttcac cgtccgaaca aggctgctgg tgagactcca ggaaggcaat    1140
gagtcactga ctgtggaagt ctccattgac aggaatcctc ctcaattaca aggcttccgg    1200
aagttcaaca ttctgacttc aaaccagaaa actttgaccc ccgagaaggg gcagagtcag    1260
ggtttgattt gggactttgg ttacctgact ctggtggagc aacgttcagg tggttcagga    1320
aagggcagca ataaggggcc actaggtgtg acagaggaac tgcacatcat cagcttcacg    1380
gtcaaatata cctaccaggg tctgaagcag gagctgaaaa cggacaccct ccctgtggtg    1440
attatttcca acatgaacca gctctcaatt gcctgggctt cagttctctg gttcaatttg    1500
ctcagcccaa accttcagaa ccagcagttc ttctccaacc cccccaaggc cccctggagc    1560
ttgctgggcc ctgctctcag ttggcagttc tcctcctatg ttggccgagg cctcaactca    1620
gaccagctga gcatgctgag aaacaagctg ttcgggcaga actgtaggac tgaggatcca    1680
ttattgtcct gggctgactt cactaagcga gagagccctc ctggcaagtt accattctgg    1740
acatggctgg acaaaattct ggagttggta catgaccacc tgaaggatct ctggaatgat    1800
ggacgcatca tgggctttgt gagtcggagc caggagcgcc ggctgctgaa gaagaccatg    1860
tctggcacct ttctactgcg cttcagtgaa tcgtcagaag ggggcattac ctgctcctgg    1920
gtggagcacc aggatgatga caaggtgctc atctactctg tgcaaccgta cacgaaggag    1980
gtgctgcagt cactcccgct gactgaaatc atccgccatt accagttgct cactgaggag    2040
aatatacctg aaaacccact gcgcttcctc tatccccgaa tcccccggga tgaagctttt    2100
gggtgctact accaggagaa agttaatctc caggaacgga ggaaatacct gaaacacagg    2160
ctcattgtgg tctctaatag acaggtggat gaactgcaac aaccgctgga gcttaagcca    2220
gagccagagc tggagtcatt agagctggaa ctagggctgg tgccagagcc agagctcagc    2280
ctggacttag agccactgct gaaggcaggg ctggatctgg ggccagagct agagtctgtg    2340
ctggagtcca ctctggagcc tgtgatagag cccacactat gcatggtatc acaaacagtg    2400
ccagagccag accaaggacc tgtatcacag ccagtgccag agccagattt gccctgtgat    2460
ctgagacatt tgaacactga gccaatggaa atcttcagaa actgtgtaaa gattgaagaa    2520
atcatgccga atggtgaccc actgttggct ggccagaaca ccgtggatga ggtttacgtc    2580
tcccgcccca gccacttcta cactgatgga cccttgatgc cttctgactt ctaggaacca    2640
catttcctct gttcttttca tatctcttgc ccttcctact cctcatagca tgatattgtt    2700
ctccaaggat gggaatcagg catgtgtccc ttccaagctg tgttaactgt tcaaactcag    2760
gcctgtgtga ctccattggg gtgagaggtg aaagcataac atgggtacag aggggacaac    2820
aatgaatcag aacagatgct gagccatagg tctaaatagg atcctggagg ctgcctgctg    2880
tgctgggagg tataggggtc ctgggggcag gccagggcag ttgacaggta cttggagggc    2940
tcagggcagt ggcttctttc cagtatgaa ggatttcaac attttaatag ttggttaggc    3000
taaactggtg catactggca ttggcccttg gtggggagca cagacacagg ataggactcc    3060 atttcttttct tccattcctt catgtctagg ataacttgct ttcttctttc ctttactcct    3120
```

```
ggctcaagcc ctgaatttct tcttttcctg caggggttga gagctttctg ccttagccta     3180
ccatgtgaaa ctctaccctg aagaaaggga tggataggaa gtagacctct ttttcttacc     3240
agtctcctcc cctactctgc ccctaagctg gctgtacctg ttcctccccc ataaaatgat     3300
cctgccaatc taatgtgagt gtgaagcttt gcacactagt ttatgctacc tagtctccac     3360
tttctcaatg cttaggagac agatcactcc tggaggctgg ggatggtagg attgctgggg     3420 atttttttt ttttaaacag ggtctcactc tgttgcccag gctagagtgc aatggtgcaa     3480
tcacagctca ctgcagcctc aacctcctgg gttcaagcaa tcctcctacc tcagcctcct     3540
gggtagctag caccatggca tgcgccacca tgccctattt ttttttttta aagacagggt     3600
cttgctatat tgcccaggct ggtcttgaac tgggctcaag tgatcctcac gccttggcct     3660
cccaaagtgc tgggattata ggcatgagcc actgtgcttg ccaggatttt ttttttttt     3720 tttttgaga tggagtttct ctcttgttgt ccaggctgga gtgcaatggt gtgatctcgg     3780
ctcactgcaa cctccgcctt ccgggttcaa gtgactctcc tgcctcagcc tcccagtag     3840 ctgggattac agatctgcac caccatgccc agctaatttt gtatttttag tagagacggg     3900
gtttctccat gttggtcagg ctggtctcga actcctgacc tcaagtgatc tgtccacctc     3960
ggcctcccag agtgctggga ttacaggcgt gagccactgt tcccagcagg aatttctttt     4020
ttatagtatt ggataaagtt tggtgttttt acagaggaga agcaatgggt cttagctctt     4080
tctctattat gttatcatcc tcccttttt gtacaatatg ttgtttacct gaaaggaagg     4140
tttctattcg ttggttgtgg acctggacaa agtccaagtc tgtggaactt aaaaccttga     4200
aggtctgtca taggactctg gacaatctca caccttagct attcccaggg aaccccaggg     4260
ggcaactgac attgctccaa gatgttctcc tgatgtagct tgagatataa aggaaaggcc     4320
ctgcacaggt ggctgtttct tgtctgttat gtcagaggaa cagtcctgtt cagaaagggg     4380
ctcttctgag cagaaatggc taataaactt tgtgctgatc tggaaaaaaa aaaaaaaaa     4440 aaaaaaaaa a                                                          4451

<210> SEQ ID NO 14
<211> LENGTH: 12171
<212> TYPE: DNA
<213> ORGANISM: Homo sapiens

<400> SEQUENCE: 14 tttttcttctg cacttctgtc tggagaggtc tgtagccact gagggccccg gtcggggccg      60
ctttgcaggt ccctagtcag gaccgagcag gggagtagga taggaatccc cgccgcacct     120
ttgtacgagc ctgacccctt ccgtgggttt gttcctgggt cgccgtcaag ctgcggtctc     180
tcctcccccg cccttcagcc ccgcggtctc caggggcggc gccctgggtc tggaacgcgg     240
ttgccaccga ggaggcggcg gccctgcgtc tggaacgccg ttgccaccga ggaggcggcg     300
gccccgagcg cgcctggaag ccccgggcaa ccggccaggg tcgggcacag gtggggtccg     360
tcaggccgcc cggggctcct ctgtcccagc tctgcggccc aggggggtgac gtgatggcgg     420 cagcggtgct gacggaccgg gcccaggtgt ctgtgacctt tgatgatgtg gctgtgactt     480
tcaccaagga ggagtggggg cagctggacc tagctcagcg gaccctgtac caggaggtga     540
tgctggaaaa ctgtgggctc ctggtgtctc tggggtgtcc tgttcccaaa gctgagctga     600
tctgccacct agagcatggg caggagccat ggaccaggaa ggaagacctc tcccaagaca     660
cctgtccagg cgacaaagga aaacctaaga ccacagaacc taccacttgt gagccagcct     720
```

```
tgtcagaggg aatctcactt cagggacaag tgacacaagg aaactcagtg gactcacagt    780
tggggcaagc cgaggatcag gatgggctat cagaaatgca ggaaggacac ttcagaccag    840
gaatagatcc ccaggagaag tctcctggga agatgagccc tgaatgtgat ggtttaggga    900
cagctgatgg tgtgtgttca aggattggac aggagcaagt ctctccagga gatagagtcc    960
gtagccataa ctcatgtgag tcaggtaaag atcccatgat tcaggaagag gaaaataact   1020
ttaaatgcag tgaatgtgga aaagtattta acaagaaaca cctccttgct ggacatgaga   1080
aaattcactc tggagttaag ccctatgaat gcacagaatg tgggaaaacc tttattaaga   1140
gcacacatct cctgcaacat cacatgatcc acactgggga gaggccctat gagtgcatgg   1200
agtgtggaaa ggccttcaac cgcaagtcat accttaccca gcaccagcgg attcacagtg   1260
gagagaagcc ttacaagtgc aatgaatgcg gaaaggcctt cacccaccgc tccaattttg   1320
tcttgcataa caggagacac actggagaaa atcctttgt gtgcacagaa tgtggccaag   1380
tctttcgaca taggccaggc tttctccggc actatgttgt ccacagtggt gagaatccct   1440
atgagtgctt ggagtgtggc aaggtcttca acacaggtc atatctcatg tggcaccagc   1500
agactcatac cggggagaag ccctatgagt gcagtgaatg tgggaaggtc ttcttggaga   1560
gtgcagccct gattcaccac tatgtcatcc acactggaga gaagcccttt gagtgcctcg   1620
agtgtgggaa ggctttcaac caccgatcct acctcaagag gcaccagcgg attcacactg   1680
gggagaagcc cttcgtgtgc agtgaatgtg aaaggccttt cacccactgc tctacttta   1740 tcttgcataa aagggcccac actggagaaa agcctttcga gtgcaaagag tgtgggaaag   1800
cctttagcaa tcggaaggac ctcattcgcc acttcagcat ccacactgga gagaagccct   1860
atgagtgcgt ggagtgtgga aaggccttca cccgcatgtc gggcctcacg aggcacaagc   1920
ggattcatag tggagagaag cctatgaat gtgttgagtg tgggaaatcg ttttgctgga   1980
gcacaaacct cattcgacat gccattatcc cactggaga gaagccctat aaatgtagtg   2040
aatgtggaaa ggccttcagt cgcagctcgt ccctcactca gcatcaaagg atgcatactg   2100
ggaaaaatcc catcagtgta acagatgtgg gaagacctt tacaagtgga caaacctcag   2160
ttacccttcg agaacttctt ttagggaagg acttttttgaa tgtaaccact gaggcaaata   2220
ttttgccaga ggaaacatct tcctctgcat ctgatcaacc ataccaaaga gaaacccac   2280 aagtgtcttc actgtgagaa aaccttctgt tgctgaatat tacttgtcat ctgaagagtc   2340
atattagaaa ttcgttcagt ctagagcctt attctccatc tgataattta tcctggagag   2400
agacccagtg gttattgtgc acataggaga accttcagct gcatctttct ccttagttta   2460
cagtgcaatt ttatctcagg aattattttt aaaaggagga ggggacatag aaaaaatgaa   2520
atgcaagcac acatcttttc aggcttctct gccaagccta tggcgctttg tcatggattt   2580
cttagtgtat ttgggggaag ggaaatgttt caaggtaaag aaccttgacc ctttatgtgc   2640
ttgtatgtac atttattgct atccagtgtc agaacagtta gtttaggaaa agtatgcaaa   2700
ctttaatcgc acatcttctg tattccacaa tagtacttac tcttgagaag cataacttta   2760
tgacaactta gggggcttga gccatgaaat actcacgttt aagtcagtaa ggatacacat   2820
gttaacattc aggcttttgt cttgatgccc gtcttttggt ttacgtcatc attgtagcca   2880
tatggtaaat ttttatttgt taaatttta aaaattactt agctcaaaat gtcagtggta   2940 aattttaaa ttgagtaaag tgattcttct ttgctcttat ttaaaatcga cagcatttct   3000
agttcctttg acattccata taattttag gattagtttg tacttattta caaacagtc   3060 ttgttcagat ttttacagaa attgagttaa gtctgtggat taatctgtta agaattggta   3120
```

```
tctttactat gttgggtctt gtagttcatg agtgcaggag taggcctctt aatttataat    3180
agttaagcat tccttaaagt atttcattaa tgttaaaaat tttcagcgta tagatcccta    3240
tgcattttg ttagaatttg catcctaggg tgctttttg tttgtgtgtg tgtgtaattt      3300
gagtgattgt aaatggcatt gatgtttgaa ctttgaattg cacacaattt ttggtagtat    3360
acagaaatat aatattttg gacattgttt tgctaccctg caaccttatt gagttcactt     3420
attatttta gctatttctt tcgacagaat ccttggaatt ttctatatag aaatgtcatc     3480
tgcaaataca gaccattttt tatctttcat cttacctgta atatacctt tatttccttt     3540
ttgtttgtct tattgcattg cacaagctgg gacttccatt atagcgttga ataggaatag    3600
tgagaaaggc catccttacc tggttcctga tagtaggggg gacaatgttc agttttttgt    3660
tttttgtttt tttgtttgag acagggtctc gctctgtcac ccaggctgga gtgcagtggc    3720
acgatcttgt ctcaccatag ccttaagttc ctgggctcaa gtgatccccc cacctcagcc    3780
ctcaccaccc cccagtagct ggtactacaa gcatgcacca ccagtcccag ctaatttttg    3840
tattttttgg tagagacagg gtttcaccat ggtgcccagg ctggtcttga actcctgggc    3900
tcaagcaacc tgcttgcctg ggtctcccaa agtgctggga ttacaggcgt gagccacagt    3960
gcacagcatg ttcagttttt catcatgaag tataatgtaa gttttataaa acatatgtcc    4020
tctataaggg taaaaatttt cctctgttcc cagtttctg agactctgtg ttgctatgaa     4080
taagtgtgga attttgttca gtacttttc tccaccagtt gatgtcatta tgctatttc     4140
cttctacatc ctattgatgg aatgtattgc tttgatcaag ttttgaatat tgagccagcc    4200
ttgcatcctt agaataaacc atacttgttt gtagagtata attgttttta tatatcattt    4260
gacatcattc cctttgtttg tattttgttg aggaaatatt cctctaattt attggctaat   4320
aatgtgtagt tcttttttct tttgtttctt atgttctaaa tgtcttatgt gtggttttga    4380
tgtctaggtg atcttgacct ttcaacatga attggaagga gttctcttct aattttttgga  4440
agactgtgta gaattggtgt tatttgttct tgtcatgttt gatgacctct agtcaaccat    4500
tgggccagag attttctcc tggaggcttt taaattacat atttatttta ttggataggt    4560
agaactattc gaagtatcta tttcttgtgt aataaatttt gatagtctgt cctgttgaag    4620
gaatatttca tctgtatttg tagcactccc ttattctttt gatagcagga tctgcacttc    4680
tttttatttt taatatttaa aatgtgcata ctcattttat gattgagtct tcttagacat    4740
ttatcagttt tattgcgcat catgctgaaa gatgtaattt ttgcttcatc tctcacttca    4800
gagaactagc actttatatt aatgatttgt ctctattctt gatttctttg atttctgctc    4860
tgatcggtat tatattccac ttgctttggt tgtatttggc tctttctaac ttttcaaggt    4920
ggggttttag attattgatt tgagattttt ttgctttttt aatgtaagca ttacattgta    4980
taaatttacc tcatatcact attggtttga tcccacaagt tttaatgttt tcattacatt    5040
ttaattctaa tagtttttat ttttgagac attctctctt agccatgaat tattaaatag     5100
tatgcttaat tttctggtgt ttggcatatt tgttactgat ttctaatttg ttccatgttt    5160
gatctgactg tttaaatgtg ttaacatttt tttatgaccc aggataggt ctatcttgtt     5220
tcgtatagct gcttgaaaag aatgggtgtt ctgctgttac tgggtggagt ttctataaat    5280
gtctctatga tcctgctcat tgttattcaa gtcagctatg tccttgctga ttttctgtcc    5340
agcatttctg tcagttgctg agaggggtgt tgaagtcctg aacataggcc gggtgcagtg    5400
gctcacgcct gtaatcctag cactttgaga ccactaaggc aggtggatca cctgaggcca    5460
```

```
ggagttcgag accagcctgg ccaacatggc aaaaccctgt ctactaaaaa tacaaaaatt   5520
agccaggcat ggtggcgtgt gcctgtaatc ccagctgctg gggggctgag gcaggaggat   5580
cagttgaacg tgggaggcag aggttgcagt gagctgagat ctcaccactg cactccagcc   5640
tgggcaacag agcgagactc tgtctcaaca acaacaacaa aaagtcctga acatgattgt   5700
ggaagtgtgt tgctctttca agttctatca cttttttgttt gcaaagttca aagctgtatt   5760
gtttggtaca tatacatgta ggtttgccaa gtctttgtgg tgaattgact cttctgtcat   5820
tatgtgatgt cattttttttg cctttttaata gtcttgtcaa tactttacct gatgttctca   5880
tagtgactcc tgcatatttt gattaatgtt tgcatggtta atatttcttc attttatttt   5940
aaagcttacc tgtatcatta cttatgaagt cagtttcttt gaacagcata tactcaggcc   6000 atgcttttttt tattcattct gcatatgtct ctcttaattg gtatgttgaa atgatttaca   6060
ttaaaataat tattgatatt ttagggctta agtgtgccct taaatgattt ttgtgttctt   6120
ttttattgtt cctctgttat ttgggggttgt ttactagtct tcctataggt tacttcacct   6180
tttttttttt taataatttg atttgataca tatgtagtgt ttttttagtat agatcctcct   6240 tgacttatga tgggggttatg tcacaataaa cccattgcaa gttgaaaata ctatgtcaaa   6300
tatgcattta atacacctac cctgctgaac atcatagccg atcttgcctt cagaatgctc   6360
agaaaattta cattagcctg cagttgggca aaatcatcta acacaaggcc tactttataa   6420
taaagttact gcaagaatt ttaaataaaa attcaagtgt ggtttctact gaatgcatgt   6480
cgcattcgca ccattgtaaa gtcaagtagt aagtcgaacc atcctaagtc agggactgtc   6540
tgtatatatc tgcatttttt agtgattgtt ctactattac agtgtaaata taaacttat   6600 gacagtttaa taagttatca gcaatttagc acttacttc cattaggttc ctttagctta   6660
cctactaatg taactatctt aagtaatagt aattcctctt caaaaattga gcgctatgtt   6720
gcaagatgta atttttcttt tcctttttttt tgagaccaag tctcactctg tcacccacgc   6780
tggagtgctg tgatgcgatc tcggctctct gcaacctctg cctcccgggt tcaagcaatt   6840
aactgcctca gcttccctag taatggatta caggcgcccg ccaccacgcc tggctaattt   6900
ttgtattttt agtagagacg gggtttcacc atcttggcca ggttggtctt gaactcttga   6960
cctcatgatc cacccgcctc ggccccccaa agtgctgggg ttacaggtgt gagccactgc   7020
acccggccac aagatgtaat ttttactttta tctctcacac gtattttaca aaacgtcatg   7080
agaaacattg tctcttgacc tttttttttt ttttttttttt ttaaagagac agagtctcac   7140
tctgtcaccc aggctggagt gcagtggcac gatcttggct cactgcaacc tccgcctcct   7200
gggttcaagc gattctcctg cctcagcctc ctgagtagct gggattacag gtgtgcgccg   7260
ccacacccag ctaatttgt attttttagta gagacggggt ttcaccatgt tgctcaggct   7320
ggtctcaaac tcctgacctt gtgatccgcc aaccttggcc tgtcgacctc tttacccatt   7380
ccattgttca ttcttctttc ttgaaatccc aaaccttcta ttaacatttc ttttcagtta   7440
tacactgaac tttactgtag cctttcttct agagtaacaa atgttctttg ttttccttcc   7500
tctaaagatg tctttatgtt tccttcattc ccaaagaata ttttttgtgga atataagatt   7560 cagagttggc agttgttttc ttttagactt cagagatgta tctctctgtt ctgtacatta   7620 ttgttttaata taagaaaccct actagcattc aaataatcat tccctatttt acaatgcatc   7680
agttctgtca agcttcattc aaagtgtttt tcattgtctc tagtgttcag aagtttggct   7740
gtgatgtgcg tggcatggaa gttttttgggt gtattctatt tggcgctccc tggtgcttgc   7800
ccagcttttt gatctgtagg attatgcctt ttgcaaaatt tggggaactt tcaactatta   7860
```

```
tttcttcaaa tatttttttca ccccccagtc ttgtcttttt tagggacttc aataacatga      7920
gtggcagatc ttgttttaca ctcccatggg tccttcaggc tctcatcttt tttcttttttc     7980
cagtctattt tctgtcttgt taatattgat taattttttat tgaccttcca tggtcctcac     8040
tgattgtttt ctttgtcata cctaatctgt tgagtttgtg cagtgagttt tcattttggt     8100
tttgtatttt ccagttgttt aatttccatt gggtgggttc ttttgtacac cttctgtttc     8160
tttgcttatt ttttaacgcc aaagaaagac tctcagagaa tagacaacta tattccaaag     8220
tcatggttct ctggtggttt gtcttgacat ttgaatagaa atgttaaact atctggggga     8280
atagaaagcc cacagtcttc tgagttgtgc tacaccaata tttctatgaa cagatcttac     8340
aactgagagt gatctgcaga ttttttcagag tcatgttctc catggaatgt ttgtaaaatt     8400
ccctagctct ctgcactgag ctgagatcgt gccactgcac tccagcctgg gcaacagagc     8460
gagactccat ctcaaaaaaa aaaaaaattc tctagctctc tatgccttgt tgtatcctca     8520
ggaaggagtc acctctcttc caggatcact cttgccttttt gttattggac acattttcct     8580
acctcctgcc cagtcttttt taggctctct gtcatacttc ctcgcctagt ctttaacttg     8640
tctctgataa ccagattttt cccccataat ctgtatctgt attcaagtct ctatcctcat     8700
ccccaaatgg atttcacccc gcttgtccat cagtctctgc ccatttcttc tgtctcccac     8760
agacatggtc tgtgtagttg ttctgcacac tacccgtcct cgccccttct catttccctc     8820
actccacgga cagctacagg agggcttcca tcatttgtcc tcttacttcc ttgttagaac     8880
tttgtgctgc tgaccaccac tctgaaccaa aacttctttc ttggttcttg aaagttgctg     8940
tctttctcct ccagagggtc tgtgtcttcc ttccaactct taaacatttt tgtttcccag     9000
aatccatcat tggccattgc ttttcactt gccatgagct ctgtgaatga atggttcct      9060
gctgaagaca tttactttca atgatctaca gaatttccca aatctatgtc tccagactgg     9120
atgtttctca cgtctgtggc ccactgggca tcttctgcac tttctctgca tttgtaaaca     9180
ctgagcctgt atgcgtgtct atgtggccat ggccctggcc gtggggatgc acccataatt     9240
ataatgagag caggtgaatg tcatgtggct atgtatgaga cattgttgtg aatgttttac     9300
atgcatcagc tcttttcaaca tttacagcat ctgtgtgtgg taggtaatgt tgtttccttc     9360
attttgcaga gcagaatata gataggctca ggttaagaat ttgcccaagg ttacacagtt     9420
atgaagtttg gatttaggaa tgggaggcca cgtagactgg cttcagaatt catgtctttta    9480
accactttat tgcttctcat gttgggggt ttgttttctg gtcactattt ttactaaagt     9540
tgattcaaca atgctataat ctgttactct cattcgacaa tacatcttga ctgtttcttc     9600
aacttgagga aggtaaacca aagccactct ttaatgggtg caaatatctg ttgtaactat     9660
gtagaagata cagtgtctgg gtttgaggac aggggagtgg gaaaactgag tagggaagcg     9720
gtaagacatg catctggctt taggagtgtt tgaagtgcct aaagatcagg gtgaatttcc     9780
caaatttgaa tcttgttgcc caagccacat tgcaaccacc tctttttctc ttacctcgtc     9840
cccacatcca ggcactgccc cattctgttc attccacctt ttttttttagt agaccctcca     9900
tatatgtgtg tgttttggtg aatggccaca cacagcaaag ttattttat tgcaattttg      9960
ttgttgttgt ttgagacaca gagtctcata ctctgccacc cagactgaag tgcagtggtg    10020
cgatctcagt tcactgcaac ctccatcccc ccatgttcaa gcaattctcc tgcctcagcc    10080
tcccaagtag ctgggattac aggcatgggc caccatgccc ggctaatttt tgtatttttt    10140
gtagacacgg ggtttcacca tgttggccag gctggtctca cactcctgac ctcaggtgat    10200
```

| | | | | | |
|---|---|---|---|---|---|
| ccacccgcct | cggcctcccg | aagtgctggc | attacaggca | tgagccacca | cacccagcct | 10260
| ttattgcaat | ttttggttcc | ctcacagaat | gtttaccatg | aagctgtgcg | tataggtggt | 10320
| accatgtatg | acataccttg | acctcaaaga | taatctacct | gggctttttt | tgtttgtttg | 10380
| ttttgagatg | gagtctcact | ctgtcaccca | tgctggtgtg | cagtggcgtg | atcttggctc | 10440
| acagcagcct | ctgcctcccg | ggttcaagcg | attctcctgc | ctcagcctcc | tgagtagctg | 10500
| ggactacagg | tgcctgcgac | cacacccagc | taattttttgt | attttttagta | gtagtgggat | 10560
| ttcaccatgt | tggccaggat | ggcctccacc | tcctgacttc | atgatccacc | cgcctcggcc | 10620
| tcccaaagtg | ctgggattac | aggcgtgagc | caccgcacct | ggcctacctg | gcttttttg | 10680
| gacagatgta | catgatttta | gaaattgtta | tgaatgactg | tcttgggatc | ctcaagaaca | 10740
| cccccaggtt | tgacgatttg | ctgagaagac | tcaggtctca | gcattctgtc | atactcaaca | 10800
| gctatgattt | actgcagcaa | aaaaatacaa | agcaaatagt | aaagggaaaa | agccaaaatt | 10860
| cagagaaaac | caggcacaat | cttctgagtc | ttgtttcagt | gaagtcacag | gatgtgcctt | 10920
| atttaagttc | catctggtac | ttatgacaac | acatgctata | tgtccactgg | gaagcttatt | 10980
| agagactcag | tgccagggtt | tttattgggc | atgttttcta | gcacatccca | caattctgga | 11040
| cttccagaag | gttagcaggg | gttcagcttt | tcagctgaaa | acgttatccc | cctttcagct | 11100
| ggggggaaaa | aaaggcaccg | aaaaacaggg | cagtgagcta | ctcctgtttt | gggtgggtgg | 11160
| agcagtagta | agcctcccaa | aatctaaggt | cccacactcc | agcaagggtg | aaccttgcaa | 11220
| actcaaaagg | atagcagtct | ccaacctgct | gttttataca | gtgacttaag | tggtactaaa | 11280
| atgctatata | agtcaaattt | acgtaacatt | aagcaaataa | ttttttttca | gcaaaaaaat | 11340
| aatggtcatg | actttgtggt | gaaggcttat | gtaatgattg | taataaattc | aggtggctca | 11400
| cgcctgtgat | accagcactt | tgggaggct | gaggcgggtg | gatcacttga | ggtcaggagt | 11460
| ttgagaccag | cctagccaac | atggtgaaat | cccatctcta | caaaaatgaa | aaattagccg | 11520
| ggcgtagtgg | tacatgcatt | tagtcctagc | tacttgggag | gctgaggcag | gaaaatcgct | 11580
| tgaacctggg | aggcagaggt | tgcagtgagc | cgagatcatg | ccactgcact | ccagcctggg | 11640
| tgacagagtg | agactgtgtc | tcaaaaaaaa | aaaaaaaaa | aaaatgcctc | agttttgtta | 11700
| agaggaaaaa | gcaaatccta | agttacagtg | gaacttatga | acaccctagc | ctagagattt | 11760
| aatttagtga | tgaaaggta | cagagagagt | ctttcaagaa | aggacctagt | ctgctcgcgt | 11820
| tctctctctc | tctctctcta | tatatatata | tgtatatgtg | tgtgtacata | tggaccactt | 11880
| caagctacac | acacacacac | acatatacac | gtgtatgaat | atatatatat | ggctataagt | 11940
| ggtgcgactt | gcaggtactc | cctttgttca | cctttgtaaa | gatgttattg | ccagttcagt | 12000
| gtgtatttct | atagtatata | tgtaaacaat | ttgtcatcct | tttgttgctg | cttttgaaac | 12060
| tagttcatgg | cttcagtggg | ggagagattt | aaataaatatg | ggtttataat | ttctgcatta | 12120
| ttaaatgcag | ataacttgtg | attaaagagt | atgttattgg | aaaaaaaaaa | a | 12171

```
<210> SEQ ID NO 15
<211> LENGTH: 2723
<212> TYPE: DNA
<213> ORGANISM: Homo sapiens

<400> SEQUENCE: 15
```

| | | | | | |
|---|---|---|---|---|---|
| gagctccggg | gtgggaccag | gcgggccaag | agggccggga | cgccgcgcgg | ggcagtgtgg | 60
| gactggggcg | gaacgccgcc | cggccgcggg | tcggctctg | tgtcagcagc | cgggcggcg | 120
| ctcgggcggg | acatggcagc | ctgtacagcc | cggcgggccc | tggccgtggg | cagccgctgg | 180

```
tggtcccggt cgctgactgg ggcccggtgg ccaaggccgc tctgtgcggg ggccggagct    240
ggagccttct cgccagcgtc gaccacgacg acgcggaggc acctctcgtc ccgaaaccga    300
ccagagggca aagtgttgga gacagttggt gtgtttgagg tgccaaaaca gaatggaaaa    360
tatgagaccg ggcagctttt ccttcatagc attttttggct accgaggtgt cgtcctgttt    420
ccctggcagg ccagactgta tgaccgggat gtggcttctg cagctccaga aaaagcagag    480
aaccctgctg gccatggctc caaggaggtg aaaggcaaaa ctcacactta ctatcaggtg    540
ctgattgatg ctcgtgactg cccacatata tctcagagat ctcagacaga agctgtgacc    600
ttcttggcta accatgatga cagtcgggcc ctctatgcca tcccaggctt ggactatgtc    660
agccatgaag acatcctccc ctacacctcc actgatcagg ttcccatcca acatgaactc    720
tttgaaagat tcttctgta tgaccagaca aaagcacctc cttttgtggc tcggagacg    780 ctaagggcct ggcaagagaa gaatcacccc tggctggagc tctccgatgt tcatcgggaa    840
acaactgaga acatacgtgt cactgtcatc cccttctaca tgggcatgag ggaagcccag    900
aattcccacg tgtactggtg gcgctactgt atccgtttgg agaaccttga cagtgatgtg    960
gtacagctcc gggagcggca ctggaggata ttcagtctct ctggcacctt ggagacagtg   1020
cgaggccgag gggtagtggg cagggaacca gtgttatcca aggagcagcc tgcgttccag   1080
tatagcagcc acgtctcgct gcaggcttcc agtgggcaca tgtggggcac gttccgcttt   1140
gaaagacctg atggctccca cttttgatgtt cggattcctc ccttctccct ggaaagcaat   1200
aaagatgaga agacaccacc ctcaggcctt cactggtagg ccagctgagg ccccaagtgc   1260
ccaggcttgg tcaccgggaa gaacaactct catcccacaa ttgctgcaga actcttctct   1320
ccccatcatg ggccacagtg ggtctcttaa tttgattgtg gggttctttt tgtggggagg   1380
ggtggtataa cttttcttca gaagacccat gtgggacacc tccaaggctg gcctcctcat   1440
aagccctgcc tacaccatgt tccagtaaac ctctccacca aggaactgtg ttcagctgcc   1500
acaggcctgg aggagttttcc tggcctgtca cgtgaggttt gatcagtaaa ccagtgcacg   1560
cttggccacc cttgccatttt ctgctcccag agtctcaggc tccccttctg acccagtgtg   1620
cgcccttgac tgctttctttt gctgcccttc cagggagctg ccccccctggt agggcatgtg   1680 cctgttttccc tctcagcctg gaggctggct ggacatctcc tagggtcact gtgcctctca   1740
gctagttggc gggggtgctg gactggactc ttgttcactt taccttctgc caaatgcaga   1800
gagggaggcc agtgtcaggg tcggagtggc ctggctctta gcactgaccg accattgcca   1860
tttctggcct cgctaggccc aggagaggag ggaggcaagc cagtcgggtt tcctggagca   1920
atgggtgtgc cagccctcag catgactctg ccaagcatcc agaccacaaa tgcaggaatt   1980
tggctgagga gcagctttag gtatggattg atgactaagt caagctactt cctgagcttc   2040
tctcagattt ccaagagcca gagatgaatt gtgctgcatc ttgccccaat tcttaggatt   2100
tcttttcctc cgccactgca gtgattgtta gaggtagttt tcttgaatta atattaaatc   2160
acagttccag cccttgttat tcttgtcctt agtcctccag ggggagctgg ggttgcaggg   2220
caacagtaca gtcgcgctta cgacctggct agaacacaag gtcagatgat aaacagaagc   2280
acaggaactc agcccatggc cgcaagctgg tcaaggcctg ctcactgtaa acatggctct   2340
gtaccattga gtttaacaca atttttattag aaattagtgt ttgcttccat cacttatgct   2400
gagcaaccaa atattacagt tatgtgataa aggaaaaatt cttcctgcc caggacctgc   2460 gccatccttt aggccgacct tggtcacata ccaaattcaa taaaacccaa tactggcctg   2520
```

| | |
|---|---|
| tgttgttaac agcaggctgc caggtttctc agaaactgac aagaaaatct gaccttcatc | 2580 |
| catactttgt ttacttaccc ctgggctgct tggagttgaa aaatgcacac agccaagagt | 2640 |
| tgctttctga atagggctgg aaactttcaa agaaaacccc caaacttttta agtcacaaag | 2700 |
| tctgattaaa gaagctaaga tca | 2723 |

<210> SEQ ID NO 16
<211> LENGTH: 1435
<212> TYPE: DNA
<213> ORGANISM: Homo sapiens

<400> SEQUENCE: 16

| | |
|---|---|
| ggcggggcct gcttctcctc agcttcaggc ggctgcgacg agccctcagg cgaacctctc | 60 |
| ggctttcccg cgcggcgccg cctcttgctg cgcctccgcc tcctcctctg ctccgccacc | 120 |
| ggcttcctcc tcctgagcag tcagcccgcg cgccggccgg ctccgttatg cgacccgca | 180 |
| gccctggcgt cgtgattagt gatgatgaac caggttatga ccttgattta ttttgcatac | 240 |
| ctaatcatta tgctgaggat ttggaaaggg tgtttattcc tcatgactac attatggaca | 300 |
| ggactgaacg tcttgctcga gatgtgatga aggagatggg aggccatcac attgtagccc | 360 |
| tctgtgtgct caagggggc tataaattct ttgctgacct gctggattac atcaaagcac | 420 |
| tgaatagaaa tagtgataga tccattccta tgactgtaga ttttatcaga ctgaagagct | 480 |
| attgtaatga ccagtcaaca ggggacataa agtaattgg tggagatgat ctctcaactt | 540 |
| taactggaaa gaatgtcttg attgtggaag atataattga cactggcaaa acaatgcaga | 600 |
| ctttgctttc cttggtcagg cagtataatc caaagatggt caaggtcgca agcttgctgg | 660 |
| tgaaaaggac cccacgaagt gttggatata gccagactt tgttggattt gaaattccag | 720 |
| acaagtttgt tgtaggatat gcccttgact ataatgaata cttcagggat ttgaatcatg | 780 |
| tttgtgtcat tagtgaaact ggaaaagcaa aatacaaagc ctaagatgag agttcaagtt | 840 |
| gagtttggaa acatctggag tcctattgac atcgccagta aaattatcaa tgttctagtt | 900 |
| ctgtggccat ctgcttagta gagcttttg catgtatctt ctaagaattt tatctgtttt | 960 |
| gtactttaga aatgtcagtt gctgcattcc taaactgttt atttgcacta tgagcctata | 1020 |
| gactatcagt tccctttggg cggattgttg tttaacttgt aaatgaaaaa attctcttaa | 1080 |
| accacagcac tattgagtga aacattgaac tcatatctgt aagaaataaa gagaagtat | 1140 |
| attagttttt taattggtat tttaattttt atatatgcag gaaagaatag aagtgattga | 1200 |
| atattgttaa ttataccacc gtgtgttaga aaagtaagaa gcagtcaatt ttcacatcaa | 1260 |
| agacagcatc taagaagttt tgttctgtcc tggaattatt ttagtagtgt ttcagtaatg | 1320 |
| ttgactgtat tttccaactt gttcaaatta ttaccagtga atctttgtca gcagttccct | 1380 |
| tttaaatgca aatcaataaa ttcccaaaaa tttaaaaaaa aaaaaaaaaa aaaaa | 1435 |

<210> SEQ ID NO 17
<211> LENGTH: 23
<212> TYPE: DNA
<213> ORGANISM: Artificial Sequence
<220> FEATURE:
<223> OTHER INFORMATION: EIF2S3-F17

<400> SEQUENCE: 17

| | |
|---|---|
| ctatttcctg cttagacggc ttc | 23 |

<210> SEQ ID NO 18
<211> LENGTH: 20

```
<212> TYPE: DNA
<213> ORGANISM: Artificial Sequence
<220> FEATURE:
<223> OTHER INFORMATION: EIF2S3-R18

<400> SEQUENCE: 18
caaccaatta aacgccagtg                                                    20

<210> SEQ ID NO 19
<211> LENGTH: 20
<212> TYPE: DNA
<213> ORGANISM: Artificial Sequence
<220> FEATURE:
<223> OTHER INFORMATION: EIF2S3-F19

<400> SEQUENCE: 19
ggatgcagct cttctgttga                                                    20

<210> SEQ ID NO 20
<211> LENGTH: 21
<212> TYPE: DNA
<213> ORGANISM: Artificial Sequence
<220> FEATURE:
<223> OTHER INFORMATION: EIF2S3-R20

<400> SEQUENCE: 20
tctatagcag ccaggtgttc c                                                  21

<210> SEQ ID NO 21
<211> LENGTH: 20
<212> TYPE: DNA
<213> ORGANISM: Artificial Sequence
<220> FEATURE:
<223> OTHER INFORMATION: EIF2S3-F21

<400> SEQUENCE: 21
ccttcctctt ttggcaacat                                                    20

<210> SEQ ID NO 22
<211> LENGTH: 20
<212> TYPE: DNA
<213> ORGANISM: Artificial Sequence
<220> FEATURE:
<223> OTHER INFORMATION: EIF2S3-R22

<400> SEQUENCE: 22
tggcgtcaac ttggtaacat                                                    20

<210> SEQ ID NO 23
<211> LENGTH: 22
<212> TYPE: DNA
<213> ORGANISM: Artificial Sequence
<220> FEATURE:
<223> OTHER INFORMATION: EIF2S3-F23

<400> SEQUENCE: 23
cctcggccag aatgttatag at                                                 22

<210> SEQ ID NO 24
<211> LENGTH: 23
<212> TYPE: DNA
<213> ORGANISM: Artificial Sequence
<220> FEATURE:
<223> OTHER INFORMATION: EIF2S3-R24

<400> SEQUENCE: 24
```

```
gtcaacaaag gaaacatgtc tga                                            23

<210> SEQ ID NO 25
<211> LENGTH: 20
<212> TYPE: DNA
<213> ORGANISM: Artificial Sequence
<220> FEATURE:
<223> OTHER INFORMATION: EIF2S3-F25

<400> SEQUENCE: 25
cggagcataa tgatctgcaa                                                20

<210> SEQ ID NO 26
<211> LENGTH: 20
<212> TYPE: DNA
<213> ORGANISM: Artificial Sequence
<220> FEATURE:
<223> OTHER INFORMATION: EIF2S3-R26

<400> SEQUENCE: 26
ggggtcaatt tttgttccaa                                                20

<210> SEQ ID NO 27
<211> LENGTH: 18
<212> TYPE: DNA
<213> ORGANISM: Artificial Sequence
<220> FEATURE:
<223> OTHER INFORMATION: EIF2S3-F27

<400> SEQUENCE: 27
gagccccggc ttattgtt                                                  18

<210> SEQ ID NO 28
<211> LENGTH: 21
<212> TYPE: DNA
<213> ORGANISM: Artificial Sequence
<220> FEATURE:
<223> OTHER INFORMATION: EIF2S3-R28

<400> SEQUENCE: 28
cacctccctt aaggtcatca a                                              21

<210> SEQ ID NO 29
<211> LENGTH: 25
<212> TYPE: DNA
<213> ORGANISM: Artificial Sequence
<220> FEATURE:
<223> OTHER INFORMATION: EIF2S3-F29

<400> SEQUENCE: 29
gcacacacat atatcactga acctg                                          25

<210> SEQ ID NO 30
<211> LENGTH: 24
<212> TYPE: DNA
<213> ORGANISM: Artificial Sequence
<220> FEATURE:
<223> OTHER INFORMATION: EIF2S3-R30

<400> SEQUENCE: 30
ggagaatttg tgcctttaag tttt                                           24

<210> SEQ ID NO 31
<211> LENGTH: 18
<212> TYPE: DNA
<213> ORGANISM: Artificial Sequence
```

```
<220> FEATURE:
<223> OTHER INFORMATION: EIF2S3-F31

<400> SEQUENCE: 31
gtgcagtggc gtgatctg                                             18

<210> SEQ ID NO 32
<211> LENGTH: 19
<212> TYPE: DNA
<213> ORGANISM: Artificial Sequence
<220> FEATURE:
<223> OTHER INFORMATION: EIF2S3-R32

<400> SEQUENCE: 32
gcgcacctgt aatctcagc                                            19

<210> SEQ ID NO 33
<211> LENGTH: 20
<212> TYPE: DNA
<213> ORGANISM: Artificial Sequence
<220> FEATURE:
<223> OTHER INFORMATION: EXT2-F33

<400> SEQUENCE: 33
atctcaggtg ggtctccatc                                           20

<210> SEQ ID NO 34
<211> LENGTH: 20
<212> TYPE: DNA
<213> ORGANISM: Artificial Sequence
<220> FEATURE:
<223> OTHER INFORMATION: EXT2-R34

<400> SEQUENCE: 34
agccagcttg taacacatcg                                           20

<210> SEQ ID NO 35
<211> LENGTH: 23
<212> TYPE: DNA
<213> ORGANISM: Artificial Sequence
<220> FEATURE:
<223> OTHER INFORMATION: EXT2-F35

<400> SEQUENCE: 35
gattgaagaa atgcagagac agg                                       23

<210> SEQ ID NO 36
<211> LENGTH: 22
<212> TYPE: DNA
<213> ORGANISM: Artificial Sequence
<220> FEATURE:
<223> OTHER INFORMATION: EXT2-R36

<400> SEQUENCE: 36
tggatagatc cggtcattga ta                                        22

<210> SEQ ID NO 37
<211> LENGTH: 22
<212> TYPE: DNA
<213> ORGANISM: Artificial Sequence
<220> FEATURE:
<223> OTHER INFORMATION: EXT2-F37

<400> SEQUENCE: 37
gatcttccag agaaaggacc ag                                        22
```

<210> SEQ ID NO 38
<211> LENGTH: 19
<212> TYPE: DNA
<213> ORGANISM: Artificial Sequence
<220> FEATURE:
<223> OTHER INFORMATION: EXT2-R38

<400> SEQUENCE: 38
ggatggagac ccacctgag                                                    19

<210> SEQ ID NO 39
<211> LENGTH: 21
<212> TYPE: DNA
<213> ORGANISM: Artificial Sequence
<220> FEATURE:
<223> OTHER INFORMATION: EXT2-F39

<400> SEQUENCE: 39
gggctttcac tagaccaaac a                                                 21

<210> SEQ ID NO 40
<211> LENGTH: 20
<212> TYPE: DNA
<213> ORGANISM: Artificial Sequence
<220> FEATURE:
<223> OTHER INFORMATION: EXT2-R40

<400> SEQUENCE: 40
tcccgaagac tgaagcaaac                                                   20

<210> SEQ ID NO 41
<211> LENGTH: 23
<212> TYPE: DNA
<213> ORGANISM: Artificial Sequence
<220> FEATURE:
<223> OTHER INFORMATION: EXT2-F41

<400> SEQUENCE: 41
gaactgtgaa gatattgcca tga                                               23

<210> SEQ ID NO 42
<211> LENGTH: 21
<212> TYPE: DNA
<213> ORGANISM: Artificial Sequence
<220> FEATURE:
<223> OTHER INFORMATION: EXT2-R42

<400> SEQUENCE: 42
tgaatttctt tcgtggggtt a                                                 21

<210> SEQ ID NO 43
<211> LENGTH: 21
<212> TYPE: DNA
<213> ORGANISM: Artificial Sequence
<220> FEATURE:
<223> OTHER INFORMATION: EXT2-F43

<400> SEQUENCE: 43
cgggaaaagc agttatcaag g                                                 21

<210> SEQ ID NO 44
<211> LENGTH: 21
<212> TYPE: DNA
<213> ORGANISM: Artificial Sequence
<220> FEATURE:
<223> OTHER INFORMATION: EXT2-R44

<400> SEQUENCE: 44
ttggtctagt gaaagcccat c                                              21

<210> SEQ ID NO 45
<211> LENGTH: 20
<212> TYPE: DNA
<213> ORGANISM: Artificial Sequence
<220> FEATURE:
<223> OTHER INFORMATION: EXT2-F45

<400> SEQUENCE: 45
accaaacaca catggtggag                                                20

<210> SEQ ID NO 46
<211> LENGTH: 21
<212> TYPE: DNA
<213> ORGANISM: Artificial Sequence
<220> FEATURE:
<223> OTHER INFORMATION: EXT2-R46

<400> SEQUENCE: 46
tttgtacagg acagggtcag c                                              21

<210> SEQ ID NO 47
<211> LENGTH: 20
<212> TYPE: DNA
<213> ORGANISM: Artificial Sequence
<220> FEATURE:
<223> OTHER INFORMATION: EXT2-F47

<400> SEQUENCE: 47
gaccaaacac acatggtgga                                                20

<210> SEQ ID NO 48
<211> LENGTH: 21
<212> TYPE: DNA
<213> ORGANISM: Artificial Sequence
<220> FEATURE:
<223> OTHER INFORMATION: EXT2-R48

<400> SEQUENCE: 48
tgtacaggac agggtcagct c                                              21

<210> SEQ ID NO 49
<211> LENGTH: 22
<212> TYPE: DNA
<213> ORGANISM: Artificial Sequence
<220> FEATURE:
<223> OTHER INFORMATION: EXT2-F49

<400> SEQUENCE: 49
ggcagtattg agcgatgtgt ta                                             22

<210> SEQ ID NO 50
<211> LENGTH: 22
<212> TYPE: DNA
<213> ORGANISM: Artificial Sequence
<220> FEATURE:
<223> OTHER INFORMATION: EXT2-R50

<400> SEQUENCE: 50
tggtacaacc acagatgctc tc                                             22

<210> SEQ ID NO 51

<210> SEQ ID NO 51
<211> LENGTH: 25
<212> TYPE: DNA
<213> ORGANISM: Artificial Sequence
<220> FEATURE:
<223> OTHER INFORMATION: EXT2-F51

<400> SEQUENCE: 51
catctcctat gaagaatgga atgac                                        25

<210> SEQ ID NO 52
<211> LENGTH: 20
<212> TYPE: DNA
<213> ORGANISM: Artificial Sequence
<220> FEATURE:
<223> OTHER INFORMATION: EXT2-R52

<400> SEQUENCE: 52
ttttcagcag tcctcacaac                                              20

<210> SEQ ID NO 53
<211> LENGTH: 24
<212> TYPE: DNA
<213> ORGANISM: Artificial Sequence
<220> FEATURE:
<223> OTHER INFORMATION: MCM4-F53

<400> SEQUENCE: 53
tgagtctcag tggaatccta aaaa                                         24

<210> SEQ ID NO 54
<211> LENGTH: 22
<212> TYPE: DNA
<213> ORGANISM: Artificial Sequence
<220> FEATURE:
<223> OTHER INFORMATION: MCM4-R54

<400> SEQUENCE: 54
cagcaagagg aagatcaaat ca                                           22

<210> SEQ ID NO 55
<211> LENGTH: 21
<212> TYPE: DNA
<213> ORGANISM: Artificial Sequence
<220> FEATURE:
<223> OTHER INFORMATION: MCM4-F55

<400> SEQUENCE: 55
tgtttgctca caatgatctc g                                            21

<210> SEQ ID NO 56
<211> LENGTH: 20
<212> TYPE: DNA
<213> ORGANISM: Artificial Sequence
<220> FEATURE:
<223> OTHER INFORMATION: MCM4-R56

<400> SEQUENCE: 56
cgaataggca cagctcgata                                              20

<210> SEQ ID NO 57
<211> LENGTH: 23
<212> TYPE: DNA
<213> ORGANISM: Artificial Sequence
<220> FEATURE:
<223> OTHER INFORMATION: MCM4-F57

<400> SEQUENCE: 57
atgagaaacc tgaatccaga aga                                          23

<210> SEQ ID NO 58
<211> LENGTH: 19
<212> TYPE: DNA
<213> ORGANISM: Artificial Sequence
<220> FEATURE:
<223> OTHER INFORMATION: MCM4-R58

<400> SEQUENCE: 58
tcagctggga tgtcctgat                                               19

<210> SEQ ID NO 59
<211> LENGTH: 20
<212> TYPE: DNA
<213> ORGANISM: Artificial Sequence
<220> FEATURE:
<223> OTHER INFORMATION: MCM4-F59

<400> SEQUENCE: 59
ggcggtgcta aaggactaca                                              20

<210> SEQ ID NO 60
<211> LENGTH: 22
<212> TYPE: DNA
<213> ORGANISM: Artificial Sequence
<220> FEATURE:
<223> OTHER INFORMATION: MCM4-R60

<400> SEQUENCE: 60
tgccaatctt cctcatgtct ac                                           22

<210> SEQ ID NO 61
<211> LENGTH: 19
<212> TYPE: DNA
<213> ORGANISM: Artificial Sequence
<220> FEATURE:
<223> OTHER INFORMATION: MCM4-F61

<400> SEQUENCE: 61
cccaaatgca ttcttcagc                                               19

<210> SEQ ID NO 62
<211> LENGTH: 20
<212> TYPE: DNA
<213> ORGANISM: Artificial Sequence
<220> FEATURE:
<223> OTHER INFORMATION: MCM4-R62

<400> SEQUENCE: 62
ttcttggggt tccctctacc                                              20

<210> SEQ ID NO 63
<211> LENGTH: 23
<212> TYPE: DNA
<213> ORGANISM: Artificial Sequence
<220> FEATURE:
<223> OTHER INFORMATION: MCM4-F63

<400> SEQUENCE: 63
ggaaaccaga catttatgag agg                                          23

<210> SEQ ID NO 64
<211> LENGTH: 22
<212> TYPE: DNA

```
<213> ORGANISM: Artificial Sequence
<220> FEATURE:
<223> OTHER INFORMATION: MCM4-R64

<400> SEQUENCE: 64
caaagagctg aagcaaaatt cc                                              22

<210> SEQ ID NO 65
<211> LENGTH: 21
<212> TYPE: DNA
<213> ORGANISM: Artificial Sequence
<220> FEATURE:
<223> OTHER INFORMATION: MCM4-F65

<400> SEQUENCE: 65
ggctccaagc atttatgaac a                                               21

<210> SEQ ID NO 66
<211> LENGTH: 20
<212> TYPE: DNA
<213> ORGANISM: Artificial Sequence
<220> FEATURE:
<223> OTHER INFORMATION: MCM4-R66

<400> SEQUENCE: 66
atgttgatct cagcccgaaa                                                 20

<210> SEQ ID NO 67
<211> LENGTH: 21
<212> TYPE: DNA
<213> ORGANISM: Artificial Sequence
<220> FEATURE:
<223> OTHER INFORMATION: MCM4-F67

<400> SEQUENCE: 67
aagtggatct gcagtctgac g                                               21

<210> SEQ ID NO 68
<211> LENGTH: 21
<212> TYPE: DNA
<213> ORGANISM: Artificial Sequence
<220> FEATURE:
<223> OTHER INFORMATION: MCM4-R68

<400> SEQUENCE: 68
agagactgct cacttgccac t                                               21

<210> SEQ ID NO 69
<211> LENGTH: 20
<212> TYPE: DNA
<213> ORGANISM: Artificial Sequence
<220> FEATURE:
<223> OTHER INFORMATION: MCM4-F69

<400> SEQUENCE: 69
cagcagactc tgtccattgc                                                 20

<210> SEQ ID NO 70
<211> LENGTH: 22
<212> TYPE: DNA
<213> ORGANISM: Artificial Sequence
<220> FEATURE:
<223> OTHER INFORMATION: MCM4-R70

<400> SEQUENCE: 70
tggatgtttt caatggttgt tt                                              22
```

<210> SEQ ID NO 71
<211> LENGTH: 17
<212> TYPE: DNA
<213> ORGANISM: Artificial Sequence
<220> FEATURE:
<223> OTHER INFORMATION: MCM4-F71

<400> SEQUENCE: 71
ctgggctctg cacagaa                                                    17

<210> SEQ ID NO 72
<211> LENGTH: 20
<212> TYPE: DNA
<213> ORGANISM: Artificial Sequence
<220> FEATURE:
<223> OTHER INFORMATION: MCM4-R72

<400> SEQUENCE: 72
ccagagggtc aataaaacgc                                                 20

<210> SEQ ID NO 73
<211> LENGTH: 21
<212> TYPE: DNA
<213> ORGANISM: Artificial Sequence
<220> FEATURE:
<223> OTHER INFORMATION: MCM4-F73

<400> SEQUENCE: 73
ctcttaccca caggaagtta t                                               21

<210> SEQ ID NO 74
<211> LENGTH: 18
<212> TYPE: DNA
<213> ORGANISM: Artificial Sequence
<220> FEATURE:
<223> OTHER INFORMATION: MCM4-R74

<400> SEQUENCE: 74
gggaatcagc tgggatgt                                                   18

<210> SEQ ID NO 75
<211> LENGTH: 17
<212> TYPE: DNA
<213> ORGANISM: Artificial Sequence
<220> FEATURE:
<223> OTHER INFORMATION: MDM2-F75

<400> SEQUENCE: 75
gccccgtgaa ggaaact                                                    17

<210> SEQ ID NO 76
<211> LENGTH: 23
<212> TYPE: DNA
<213> ORGANISM: Artificial Sequence
<220> FEATURE:
<223> OTHER INFORMATION: MDM2-R76

<400> SEQUENCE: 76
tgcaccaaca gactttaata act                                             23

<210> SEQ ID NO 77
<211> LENGTH: 26
<212> TYPE: DNA
<213> ORGANISM: Artificial Sequence
<220> FEATURE:

<223> OTHER INFORMATION: MDM2-F77

<400> SEQUENCE: 77
ccatgatcta caggaacttg gtagta                                          26

<210> SEQ ID NO 78
<211> LENGTH: 24
<212> TYPE: DNA
<213> ORGANISM: Artificial Sequence
<220> FEATURE:
<223> OTHER INFORMATION: MDM2-R78

<400> SEQUENCE: 78
tcactcacag atgtacctga gtcc                                            24

<210> SEQ ID NO 79
<211> LENGTH: 18
<212> TYPE: DNA
<213> ORGANISM: Artificial Sequence
<220> FEATURE:
<223> OTHER INFORMATION: MDM2-F79

<400> SEQUENCE: 79
gactccaagc gcgaaaac                                                   18

<210> SEQ ID NO 80
<211> LENGTH: 23
<212> TYPE: DNA
<213> ORGANISM: Artificial Sequence
<220> FEATURE:
<223> OTHER INFORMATION: MDM2-R80

<400> SEQUENCE: 80
cagacatgtt ggtattgcac att                                             23

<210> SEQ ID NO 81
<211> LENGTH: 25
<212> TYPE: DNA
<213> ORGANISM: Artificial Sequence
<220> FEATURE:
<223> OTHER INFORMATION: MDM2-F81

<400> SEQUENCE: 81
tctgatagta tttcccttc ctttg                                            25

<210> SEQ ID NO 82
<211> LENGTH: 22
<212> TYPE: DNA
<213> ORGANISM: Artificial Sequence
<220> FEATURE:
<223> OTHER INFORMATION: MDM2-R82

<400> SEQUENCE: 82
tgttcactta caccagcatc aa                                              22

<210> SEQ ID NO 83
<211> LENGTH: 17
<212> TYPE: DNA
<213> ORGANISM: Artificial Sequence
<220> FEATURE:
<223> OTHER INFORMATION: GRB2-F83

<400> SEQUENCE: 83
cccttccccc tgcttca                                                    17

```
<210> SEQ ID NO 84
<211> LENGTH: 24
<212> TYPE: DNA
<213> ORGANISM: Artificial Sequence
<220> FEATURE:
<223> OTHER INFORMATION: GRB2-R84

<400> SEQUENCE: 84
aacggatgtg gtttcatttc tatg                                          24

<210> SEQ ID NO 85
<211> LENGTH: 19
<212> TYPE: DNA
<213> ORGANISM: Artificial Sequence
<220> FEATURE:
<223> OTHER INFORMATION: GRB2-F85

<400> SEQUENCE: 85
gggcctttct tatccgaga                                                19

<210> SEQ ID NO 86
<211> LENGTH: 20
<212> TYPE: DNA
<213> ORGANISM: Artificial Sequence
<220> FEATURE:
<223> OTHER INFORMATION: GRB2-R86

<400> SEQUENCE: 86
tgcacatcgt ttccaaactt                                               20

<210> SEQ ID NO 87
<211> LENGTH: 26
<212> TYPE: DNA
<213> ORGANISM: Artificial Sequence
<220> FEATURE:
<223> OTHER INFORMATION: GRB2-F87

<400> SEQUENCE: 87
ccaagaacta catagaaatg aaacca                                        26

<210> SEQ ID NO 88
<211> LENGTH: 20
<212> TYPE: DNA
<213> ORGANISM: Artificial Sequence
<220> FEATURE:
<223> OTHER INFORMATION: GRB2-R88

<400> SEQUENCE: 88
ccgctgtttg ctaagcattt                                               20

<210> SEQ ID NO 89
<211> LENGTH: 20
<212> TYPE: DNA
<213> ORGANISM: Artificial Sequence
<220> FEATURE:
<223> OTHER INFORMATION: GRB2-F89

<400> SEQUENCE: 89
ctgcgggaca tagaacaggt                                               20

<210> SEQ ID NO 90
<211> LENGTH: 20
<212> TYPE: DNA
<213> ORGANISM: Artificial Sequence
<220> FEATURE:
<223> OTHER INFORMATION: GRB2-R90
```

```
<400> SEQUENCE: 90
cctggggatc aaagtcaaag                                              20

<210> SEQ ID NO 91
<211> LENGTH: 18
<212> TYPE: DNA
<213> ORGANISM: Artificial Sequence
<220> FEATURE:
<223> OTHER INFORMATION: GRB2-F91

<400> SEQUENCE: 91
gggggacatc ctcaaggt                                                18

<210> SEQ ID NO 92
<211> LENGTH: 20
<212> TYPE: DNA
<213> ORGANISM: Artificial Sequence
<220> FEATURE:
<223> OTHER INFORMATION: GRB2-R92

<400> SEQUENCE: 92
gaatgaagcc gtcttttcca                                              20

<210> SEQ ID NO 93
<211> LENGTH: 27
<212> TYPE: DNA
<213> ORGANISM: Artificial Sequence
<220> FEATURE:
<223> OTHER INFORMATION: GRB2-F93

<400> SEQUENCE: 93
caagaactac atagaaatga aaccaca                                      27

<210> SEQ ID NO 94
<211> LENGTH: 20
<212> TYPE: DNA
<213> ORGANISM: Artificial Sequence
<220> FEATURE:
<223> OTHER INFORMATION: GRB2-R94

<400> SEQUENCE: 94
gataagaaag gccccatcgt                                              20

<210> SEQ ID NO 95
<211> LENGTH: 21
<212> TYPE: DNA
<213> ORGANISM: Artificial Sequence
<220> FEATURE:
<223> OTHER INFORMATION: GRB2-F95

<400> SEQUENCE: 95
gggacttctc cctctctgtc a                                            21

<210> SEQ ID NO 96
<211> LENGTH: 24
<212> TYPE: DNA
<213> ORGANISM: Artificial Sequence
<220> FEATURE:
<223> OTHER INFORMATION: GRB2-R96

<400> SEQUENCE: 96
cattcaaaga attgaacttc acca                                         24

<210> SEQ ID NO 97
<211> LENGTH: 23
```

```
<212> TYPE: DNA
<213> ORGANISM: Artificial Sequence
<220> FEATURE:
<223> OTHER INFORMATION: NF1-F97

<400> SEQUENCE: 97
gctcacaaag acaccaaagt ttc                                           23

<210> SEQ ID NO 98
<211> LENGTH: 22
<212> TYPE: DNA
<213> ORGANISM: Artificial Sequence
<220> FEATURE:
<223> OTHER INFORMATION: NF1-R98

<400> SEQUENCE: 98
ttgttcgctc tgctgaagtt ac                                            22

<210> SEQ ID NO 99
<211> LENGTH: 21
<212> TYPE: DNA
<213> ORGANISM: Artificial Sequence
<220> FEATURE:
<223> OTHER INFORMATION: NF1-F99

<400> SEQUENCE: 99
gctggtaaat tcactccatc g                                             21

<210> SEQ ID NO 100
<211> LENGTH: 20
<212> TYPE: DNA
<213> ORGANISM: Artificial Sequence
<220> FEATURE:
<223> OTHER INFORMATION: NF1-R100

<400> SEQUENCE: 100
atcttaggcc accaatccaa                                               20

<210> SEQ ID NO 101
<211> LENGTH: 24
<212> TYPE: DNA
<213> ORGANISM: Artificial Sequence
<220> FEATURE:
<223> OTHER INFORMATION: NF1-F101

<400> SEQUENCE: 101
tgtacccatc tattcaagca aaaa                                          24

<210> SEQ ID NO 102
<211> LENGTH: 27
<212> TYPE: DNA
<213> ORGANISM: Artificial Sequence
<220> FEATURE:
<223> OTHER INFORMATION: NF1-R102

<400> SEQUENCE: 102
agtacaacat caagcagatc tgtaatc                                       27

<210> SEQ ID NO 103
<211> LENGTH: 27
<212> TYPE: DNA
<213> ORGANISM: Artificial Sequence
<220> FEATURE:
<223> OTHER INFORMATION: NF1-F103

<400> SEQUENCE: 103
```

```
ttgattatat tggatacact ggaaaaa                                          27

<210> SEQ ID NO 104
<211> LENGTH: 25
<212> TYPE: DNA
<213> ORGANISM: Artificial Sequence
<220> FEATURE:
<223> OTHER INFORMATION: NF1-R104

<400> SEQUENCE: 104
tcgtttcatc taatctcatt gtgtc                                            25

<210> SEQ ID NO 105
<211> LENGTH: 21
<212> TYPE: DNA
<213> ORGANISM: Artificial Sequence
<220> FEATURE:
<223> OTHER INFORMATION: NF1-F105

<400> SEQUENCE: 105
tgggttatgg gaacatcaaa c                                                21

<210> SEQ ID NO 106
<211> LENGTH: 20
<212> TYPE: DNA
<213> ORGANISM: Artificial Sequence
<220> FEATURE:
<223> OTHER INFORMATION: NF1-R106

<400> SEQUENCE: 106
ttgcctggtc caaatctctt                                                  20

<210> SEQ ID NO 107
<211> LENGTH: 26
<212> TYPE: DNA
<213> ORGANISM: Artificial Sequence
<220> FEATURE:
<223> OTHER INFORMATION: NF1-F107

<400> SEQUENCE: 107
cctgcatact ttagatagtc tccgta                                           26

<210> SEQ ID NO 108
<211> LENGTH: 19
<212> TYPE: DNA
<213> ORGANISM: Artificial Sequence
<220> FEATURE:
<223> OTHER INFORMATION: NF1-R108

<400> SEQUENCE: 108
ggattccgga ttgccataa                                                   19

<210> SEQ ID NO 109
<211> LENGTH: 22
<212> TYPE: DNA
<213> ORGANISM: Artificial Sequence
<220> FEATURE:
<223> OTHER INFORMATION: NF1-F109

<400> SEQUENCE: 109
ggaaaaggga actcctctat gg                                               22

<210> SEQ ID NO 110
<211> LENGTH: 18
<212> TYPE: DNA
<213> ORGANISM: Artificial Sequence
```

```
<220> FEATURE:
<223> OTHER INFORMATION: NF1-R110

<400> SEQUENCE: 110
tttggtctgg gcttgtcg                                                 18

<210> SEQ ID NO 111
<211> LENGTH: 23
<212> TYPE: DNA
<213> ORGANISM: Artificial Sequence
<220> FEATURE:
<223> OTHER INFORMATION: NF1-F111

<400> SEQUENCE: 111
tctggggtaa gtttcacagt ttc                                           23

<210> SEQ ID NO 112
<211> LENGTH: 24
<212> TYPE: DNA
<213> ORGANISM: Artificial Sequence
<220> FEATURE:
<223> OTHER INFORMATION: NF1-R112

<400> SEQUENCE: 112
caaacaaaaa caagaaaaac atcg                                          24

<210> SEQ ID NO 113
<211> LENGTH: 21
<212> TYPE: DNA
<213> ORGANISM: Artificial Sequence
<220> FEATURE:
<223> OTHER INFORMATION: NF1-F113

<400> SEQUENCE: 113
gactcccaca tctccttacc c                                             21

<210> SEQ ID NO 114
<211> LENGTH: 20
<212> TYPE: DNA
<213> ORGANISM: Artificial Sequence
<220> FEATURE:
<223> OTHER INFORMATION: NF1-R114

<400> SEQUENCE: 114
cgttctcctt gtcgattcct                                               20

<210> SEQ ID NO 115
<211> LENGTH: 20
<212> TYPE: DNA
<213> ORGANISM: Artificial Sequence
<220> FEATURE:
<223> OTHER INFORMATION: MMD-F115

<400> SEQUENCE: 115
aggatcaatg cggttcaaga                                               20

<210> SEQ ID NO 116
<211> LENGTH: 22
<212> TYPE: DNA
<213> ORGANISM: Artificial Sequence
<220> FEATURE:
<223> OTHER INFORMATION: MMD-R116

<400> SEQUENCE: 116
tcatagcaag ttggcttgta gc                                            22
```

<210> SEQ ID NO 117
<211> LENGTH: 25
<212> TYPE: DNA
<213> ORGANISM: Artificial Sequence
<220> FEATURE:
<223> OTHER INFORMATION: MMD-F117

<400> SEQUENCE: 117 tcttttcta tctcacaatg ggatt                                  25

<210> SEQ ID NO 118
<211> LENGTH: 21
<212> TYPE: DNA
<213> ORGANISM: Artificial Sequence
<220> FEATURE:
<223> OTHER INFORMATION: MMD-R118

<400> SEQUENCE: 118
ctgaagtcca tcggtgttgt t                                     21

<210> SEQ ID NO 119
<211> LENGTH: 21
<212> TYPE: DNA
<213> ORGANISM: Artificial Sequence
<220> FEATURE:
<223> OTHER INFORMATION: MMD-F119

<400> SEQUENCE: 119
gttggtttat ctggctcatg g                                     21

<210> SEQ ID NO 120
<211> LENGTH: 26
<212> TYPE: DNA
<213> ORGANISM: Artificial Sequence
<220> FEATURE:
<223> OTHER INFORMATION: MMD-R120

<400> SEQUENCE: 120
agatagaaaa agagttcaac cacctt                                26

<210> SEQ ID NO 121
<211> LENGTH: 25
<212> TYPE: DNA
<213> ORGANISM: Artificial Sequence
<220> FEATURE:
<223> OTHER INFORMATION: RNF4-F121

<400> SEQUENCE: 121
gatctgactc acaatgactc tgttg                                 25

<210> SEQ ID NO 122
<211> LENGTH: 19
<212> TYPE: DNA
<213> ORGANISM: Artificial Sequence
<220> FEATURE:
<223> OTHER INFORMATION: RNF4-R122

<400> SEQUENCE: 122
tcactgctca ccacacagc                                        19

<210> SEQ ID NO 123
<211> LENGTH: 20
<212> TYPE: DNA
<213> ORGANISM: Artificial Sequence
<220> FEATURE:
<223> OTHER INFORMATION: RNF4-F123

```
<400> SEQUENCE: 123
gcaccaaaga gcacaatgag                                                    20

<210> SEQ ID NO 124
<211> LENGTH: 21
<212> TYPE: DNA
<213> ORGANISM: Artificial Sequence
<220> FEATURE:
<223> OTHER INFORMATION: RNF4-R124

<400> SEQUENCE: 124
gagttcgctt ctgagcttgt c                                                  21

<210> SEQ ID NO 125
<211> LENGTH: 19
<212> TYPE: DNA
<213> ORGANISM: Artificial Sequence
<220> FEATURE:
<223> OTHER INFORMATION: RNF4-F125

<400> SEQUENCE: 125
ccgagatctc cttggaagc                                                     19

<210> SEQ ID NO 126
<211> LENGTH: 20
<212> TYPE: DNA
<213> ORGANISM: Artificial Sequence
<220> FEATURE:
<223> OTHER INFORMATION: RNF4-R126

<400> SEQUENCE: 126
tcaaccacca caggctctaa                                                    20

<210> SEQ ID NO 127
<211> LENGTH: 21
<212> TYPE: DNA
<213> ORGANISM: Artificial Sequence
<220> FEATURE:
<223> OTHER INFORMATION: RNF4-F127

<400> SEQUENCE: 127
gacaagctca gaagcgaact c                                                  21

<210> SEQ ID NO 128
<211> LENGTH: 20
<212> TYPE: DNA
<213> ORGANISM: Artificial Sequence
<220> FEATURE:
<223> OTHER INFORMATION: RNF4-R128

<400> SEQUENCE: 128
ccacaatttc atctccagca                                                    20

<210> SEQ ID NO 129
<211> LENGTH: 19
<212> TYPE: DNA
<213> ORGANISM: Artificial Sequence
<220> FEATURE:
<223> OTHER INFORMATION: RNF4-F129

<400> SEQUENCE: 129
agcttcttct ccggagtgc                                                     19

<210> SEQ ID NO 130
```

```
<211> LENGTH: 25
<212> TYPE: DNA
<213> ORGANISM: Artificial Sequence
<220> FEATURE:
<223> OTHER INFORMATION: RNF4-R130

<400> SEQUENCE: 130
ggacagattt ccagtatttt caagt                                        25

<210> SEQ ID NO 131
<211> LENGTH: 24
<212> TYPE: DNA
<213> ORGANISM: Artificial Sequence
<220> FEATURE:
<223> OTHER INFORMATION: RNF4-F131

<400> SEQUENCE: 131
acaatgactc tgttgtgatt gttg                                         24

<210> SEQ ID NO 132
<211> LENGTH: 19
<212> TYPE: DNA
<213> ORGANISM: Artificial Sequence
<220> FEATURE:
<223> OTHER INFORMATION: RNF4-R132

<400> SEQUENCE: 132
agctgtcagc atggtcctg                                               19

<210> SEQ ID NO 133
<211> LENGTH: 20
<212> TYPE: DNA
<213> ORGANISM: Artificial Sequence
<220> FEATURE:
<223> OTHER INFORMATION: RNF4-F133

<400> SEQUENCE: 133
cagagatcgt gcagaatgga                                              20

<210> SEQ ID NO 134
<211> LENGTH: 24
<212> TYPE: DNA
<213> ORGANISM: Artificial Sequence
<220> FEATURE:
<223> OTHER INFORMATION: RNF4-R134

<400> SEQUENCE: 134
tcgaaacagt cttttgatc tcag                                          24

<210> SEQ ID NO 135
<211> LENGTH: 20
<212> TYPE: DNA
<213> ORGANISM: Artificial Sequence
<220> FEATURE:
<223> OTHER INFORMATION: RNF4-F135

<400> SEQUENCE: 135
acgaaagaag aagaccaagg                                              20

<210> SEQ ID NO 136
<211> LENGTH: 19
<212> TYPE: DNA
<213> ORGANISM: Artificial Sequence
<220> FEATURE:
<223> OTHER INFORMATION: RNF4-R136

<400> SEQUENCE: 136
```
tgagtatccg tccatgcag                                          19

<210> SEQ ID NO 137
<211> LENGTH: 20
<212> TYPE: DNA
<213> ORGANISM: Artificial Sequence
<220> FEATURE:
<223> OTHER INFORMATION: DUSP6-F137

<400> SEQUENCE: 137
cgactggaac gagaatacgg                                         20

<210> SEQ ID NO 138
<211> LENGTH: 20
<212> TYPE: DNA
<213> ORGANISM: Artificial Sequence
<220> FEATURE:
<223> OTHER INFORMATION: DUSP6-R138

<400> SEQUENCE: 138
ggagaactcg gcttggaact                                         20

<210> SEQ ID NO 139
<211> LENGTH: 19
<212> TYPE: DNA
<213> ORGANISM: Artificial Sequence
<220> FEATURE:
<223> OTHER INFORMATION: DUSP6-F139

<400> SEQUENCE: 139
ttcctctact tgggctgtg                                          19

<210> SEQ ID NO 140
<211> LENGTH: 17
<212> TYPE: DNA
<213> ORGANISM: Artificial Sequence
<220> FEATURE:
<223> OTHER INFORMATION: DUSP6-R140

<400> SEQUENCE: 140
ccccgggctt catctat                                            17

<210> SEQ ID NO 141
<211> LENGTH: 20
<212> TYPE: DNA
<213> ORGANISM: Artificial Sequence
<220> FEATURE:
<223> OTHER INFORMATION: CPEB4-F141

<400> SEQUENCE: 141
ctcgaccatt acgagctgtg                                         20

<210> SEQ ID NO 142
<211> LENGTH: 24
<212> TYPE: DNA
<213> ORGANISM: Artificial Sequence
<220> FEATURE:
<223> OTHER INFORMATION: CPEB4-R142

<400> SEQUENCE: 142
actctgttga ttagagaacg caac                                    24

<210> SEQ ID NO 143
<211> LENGTH: 20
<212> TYPE: DNA

```
<213> ORGANISM: Artificial Sequence
<220> FEATURE:
<223> OTHER INFORMATION: WEE1-F143

<400> SEQUENCE: 143
cacaagtgct ttcccaagaa                                              20

<210> SEQ ID NO 144
<211> LENGTH: 21
<212> TYPE: DNA
<213> ORGANISM: Artificial Sequence
<220> FEATURE:
<223> OTHER INFORMATION: WEE1-R144

<400> SEQUENCE: 144
atccggtcag tgaagagtgc t                                            21

<210> SEQ ID NO 145
<211> LENGTH: 20
<212> TYPE: DNA
<213> ORGANISM: Artificial Sequence
<220> FEATURE:
<223> OTHER INFORMATION: IRF4-F145

<400> SEQUENCE: 145
gccaagattc caggtgactc                                              20

<210> SEQ ID NO 146
<211> LENGTH: 21
<212> TYPE: DNA
<213> ORGANISM: Artificial Sequence
<220> FEATURE:
<223> OTHER INFORMATION: IRF4-R146

<400> SEQUENCE: 146
ctggctagca gaggttctac g                                            21

<210> SEQ ID NO 147
<211> LENGTH: 21
<212> TYPE: DNA
<213> ORGANISM: Artificial Sequence
<220> FEATURE:
<223> OTHER INFORMATION: STAT2-F147

<400> SEQUENCE: 147
cctttctact gcgcttcagt g                                            21

<210> SEQ ID NO 148
<211> LENGTH: 23
<212> TYPE: DNA
<213> ORGANISM: Artificial Sequence
<220> FEATURE:
<223> OTHER INFORMATION: STAT2-R148

<400> SEQUENCE: 148
cagagtagat gagcaccttg tca                                          23

<210> SEQ ID NO 149
<211> LENGTH: 20
<212> TYPE: DNA
<213> ORGANISM: Artificial Sequence
<220> FEATURE:
<223> OTHER INFORMATION: ZNF264-F149

<400> SEQUENCE: 149
ctttcaccaa ggaggagtgg                                              20
```

```
<210> SEQ ID NO 150
<211> LENGTH: 20
<212> TYPE: DNA
<213> ORGANISM: Artificial Sequence
<220> FEATURE:
<223> OTHER INFORMATION: ZNF264-R150

<400> SEQUENCE: 150
cagctttggg aacaggacac                                               20

<210> SEQ ID NO 151
<211> LENGTH: 20
<212> TYPE: DNA
<213> ORGANISM: Artificial Sequence
<220> FEATURE:
<223> OTHER INFORMATION: POLDIP2-F151

<400> SEQUENCE: 151
cctggcaaga gaagaatcac                                               20

<210> SEQ ID NO 152
<211> LENGTH: 20
<212> TYPE: DNA
<213> ORGANISM: Artificial Sequence
<220> FEATURE:
<223> OTHER INFORMATION: POLDIP2-R152

<400> SEQUENCE: 152
tccaaacgga tacagtagcg                                               20

<210> SEQ ID NO 153
<211> LENGTH: 24
<212> TYPE: DNA
<213> ORGANISM: Artificial Sequence
<220> FEATURE:
<223> OTHER INFORMATION: HPRT1-F153

<400> SEQUENCE: 153
tgaccttgat ttattttgca tacc                                          24

<210> SEQ ID NO 154
<211> LENGTH: 20
<212> TYPE: DNA
<213> ORGANISM: Artificial Sequence
<220> FEATURE:
<223> OTHER INFORMATION: HPRT1-R154

<400> SEQUENCE: 154
cgagcaagac gttcagtcct                                               20

<210> SEQ ID NO 155
<211> LENGTH: 1310
<212> TYPE: DNA
<213> ORGANISM: Homo sapiens

<400> SEQUENCE: 155
aaattgagcc cgcagcctcc cgcttcgctc tctgctcctc ctgttcgaca gtcagccgca    60
tcttcttttg cgtcgccagc cgagccacat cgctcagaca ccatgggaa ggtgaaggtc    120 ggagtcaacg gatttggtcg tattgggcgc ctggtcacca gggctgcttt taactctggt   180
aaagtggata ttgttgccat caatgacccc ttcattgacc tcaactacat ggtttacatg   240
ttccaatatg attccaccca tggcaaattc catggcaccg tcaaggctga gaacgggaag   300
```

-continued

| | |
|---|---|
| cttgtcatca atggaaatcc catcaccatc ttccaggagc gagatccctc caaaatcaag | 360 |
| tggggcgatg ctggcgctga gtacgtcgtg gagtccactg gcgtcttcac caccatggag | 420 |
| aaggctgggg ctcatttgca gggggagcc aaaagggtca tcatctctgc ccctctgct | 480 |
| gatgccccca tgttcgtcat gggtgtgaac catgagaagt atgacaacag cctcaagatc | 540 |
| atcagcaatg cctcctgcac caccaactgc ttagcacccc tggccaaggt catccatgac | 600 |
| aactttggta tcgtggaagg actcatgacc acagtccatg ccatcactgc cacccagaag | 660 |
| actgtggatg cccctccgg gaaactgtgg cgtgatggcc gcgggctct ccagaacatc | 720 |
| atccctgcct ctactggcgc tgccaaggct gtgggcaagg tcatccctga gctgaacggg | 780 |
| aagctcactg gcatggcctt ccgtgtcccc actgccaacg tgtcagtggt ggacctgacc | 840 |
| tgccgtctag aaaaacctgc caaatatgat gacatcaaga aggtggtgaa gcaggcgtcg | 900 |
| gagggccccc tcaagggcat cctgggctac actgagcacc aggtggtctc ctctgacttc | 960 |
| aacagcgaca cccactcctc cacctttgac gctggggctg gcattgccct caacgaccac | 1020 |
| tttgtcaagc tcatttcctg gtatgacaac gaatttggct acagcaacag ggtggtggac | 1080 |
| ctcatggccc acatggcctc caaggagtaa gaccccctgga ccaccagccc cagcaagagc | 1140 |
| acaagaggaa gagagagacc ctcactgctg gggagtccct gccacactca gtcccccacc | 1200 |
| acactgaatc tccctcctc acagttgcca tgtagacccc ttgaagaggg gaggggccta | 1260 |
| gggagccgca ccttgtcatg taccatcaat aaagtaccct gtgctcaacc | 1310 |

<210> SEQ ID NO 156
<211> LENGTH: 1807
<212> TYPE: DNA
<213> ORGANISM: Homo sapiens

<400> SEQUENCE: 156

| | |
|---|---|
| gcggccgcgt ctcctccctc ggcgttgtcc gcggcgcgag ccacagcgcg cggggcgagc | 60 |
| cagcgagagg gcgcgagcgg cggcgctgcc tgcagcctgc agcctgcagc ctccggccgg | 120 |
| ccggcgagcc agtgcgcgtg cgcggcggcg gcctccgcag cgaccgggga gcggactgac | 180 |
| cggcgggagg gctagcgagc cagcggtgtg aggcgcgagg cgaggccgag ccgcgagcga | 240 |
| catgggggac cgggagcagc tgctgcagcg ggcgcggctg gccgagcagg cggagcgcta | 300 |
| cgacgacatg gcctccgcta tgaaggcggt gacagagctg aatgaacctc tctccaatga | 360 |
| agatcgaaat ctcctctctg tggcctacaa gaatgtggtt ggtgccaggc gatcttcctg | 420 |
| gagggtcatt agcagcattg agcagaaaac catggctgat ggaaacgaaa agaaattgga | 480 |
| gaaagttaaa gcttaccggg agaagattga aaggagctg gagacagttt gcaatgatgt | 540 |
| cctgtctctg cttgacaagt tcctgatcaa gaactgcaat gatttccagt atgagagcaa | 600 |
| ggtgttttac ctgaaaatga agggtgatta ctaccgctac ttagcagagg tcgcttctgg | 660 |
| ggagaagaaa aacagtgtgg tcgaagcttc tgaagctgcc tacaaggaag cctttgaaat | 720 |
| cagcaaagag cagatgcaac ccacgcatcc catccggctg ggcctggccc tcaacttctc | 780 |
| cgtgttctac tatgagatcc agaatgcacc tgagcaagcc tgcctcttag ccaaacaagc | 840 |
| cttcgatgat gccatagctg agctggacac actaaacgag gattcctata aggactccac | 900 |
| gctgatcatg cagttgctgc gagacaacct caccctctgg acgagcgacc agcaggatga | 960 |
| agaagcagga gaaggcaact gaagatcctt caggtcccct ggcccttcct tcacccacca | 1020 |
| cccccatcat caccgattct tccttgccac aatcactaaa tatctagtgc taaacctatc | 1080 |
| tgtattggca gcacagctac tcagatctgc actcctgtct cttgggaagc agtttcagat | 1140 |

| | |
|---|---:|
| aaatcatggg cattgctgga ctgatggttg ctttgagccc acaggagctc ccttttgaa | 1200 |
| ttgtgtggag aagtgtgttc tgatgaggca ttttactatg cctgttgatc tatgggaaat | 1260 |
| ctaggcgaaa gtaatgggga agattagaaa gaattagcca accaggctac agttgatatt | 1320 |
| taaaagatcc atttaaaaca agctgatagt gtttcgttaa gcagtacatc ttgtgcatgc | 1380 |
| aaaaatgaat tcacccctcc cacctctttc ttcaattaat ggaaaactgt taagggaagc | 1440 |
| tgatacagag agacaacttg ctcctttcca tcagctttat aataaactgt ttaacgtgag | 1500 |
| gtttcagtag ctccttggtt ttgcctcttt aaattatgac gtgcacaaac cttcttttca | 1560 |
| atgcaatgca tctgaaagtt ttgatacttg taacttttt tttttttgg ttgcaattgt | 1620 |
| ttaagaatca tggatttatt ttttgtaact ctttggctat tgtccttgtg tatcctgaca | 1680 |
| gcgccatgtg tgtcagccca tgtcaatcaa gatgggtgat tatgaaatgc cagacttcta | 1740 |
| aaataaatgt tttggaattc aatgggtaaa taaatgctgc tttggggata ttaaaaaaaa | 1800 |
| aaaaaaa | 1807 |

<210> SEQ ID NO 157
<211> LENGTH: 3245
<212> TYPE: DNA
<213> ORGANISM: Homo sapiens

<400> SEQUENCE: 157

| | |
|---|---:|
| attttgtggc ccgctatggc ggcggtgttg aggttgggta cgggatgcgg ggtctttgac | 60 |
| tgaaggggta ggccaagtgg aggtatcagg gacgtcgcgc ggcacagaag aggaccagcc | 120 |
| tggacgccgg ggacgctgtc atgtacggcg cgagcggggg ccgcgccaaa cccgagagga | 180 |
| aaagcggcgc gaaggaggag gccgggccag gcggtgccgg cggtggggc agccgagtgg | 240 |
| agctcttggt tttcggctat gcctgcaagc tgttccggga cgacgagcgg gccctggctc | 300 |
| aggaacaggg acagcacctc atccctggat tggggaccca caagatcctc atcgacagat | 360 |
| atgatggacg tggtcacctg catgaccttt ctgagtacga tgctgagtat tccacgtgga | 420 |
| acagagatta tcagctgtct gaagaggagg cgcgaataga ggccctgtgt gatgaagaga | 480 |
| ggtatttagc cttgcatacg gacttgcttg aggaggaggc aaggcaagag gaagaataca | 540 |
| agcgattgag tgaagcacta gcagaggatg ggagctacaa tgccgtgggg ttcacttacg | 600 |
| gtagcgacta ttacgacccg tcagagccga cggaggagga ggagccttcc aaacagagag | 660 |
| aaaaaaatga ggccgaaaat ttagaggaaa atgaagagcc cttcgttgcc cccttaggat | 720 |
| tgagcgtccc gtctgacgtg gagttgccac caaccgctaa aatgcacgcc atcatcgagc | 780 |
| gcacggccag cttcgtgtgc aggcagggag cacagtttga gatcatgctg aaggccaagc | 840 |
| aggcccggaa ctcccagttt gactttctgc gcttcgacca ctacctcaac ccctactata | 900 |
| agttcatcca gaaagccatg aaagagggac gctacactgt cctggcagaa aacaaaagtg | 960 |
| acgagaaaaa aaaatcagga gtcagctctg acaatgaaga tgatgatgat gaagaagatg | 1020 |
| ggaattacct tcatccctct ctctttgcct ccaagaagtg taaccgcctt gaagagctga | 1080 |
| tgaagccctt gaaggtagtg gacccagatc atcccctcgc agcacttgtt cgtaaggcac | 1140 |
| aggctgacag ttccactccc accccacaca acgcagacgc tgcgcctgtg cagccctccc | 1200 |
| aggtggagta cacggcagac tcgaccgtgg cagccatgta ttacagctac tacatgctac | 1260 |
| cggacggcac ttactgcctg cgccgccccc ctccggaat cgacgtgact acttactaca | 1320 |
| gcacccttcc tgctggcgtg accgtgtcta actcccctgg agtgacgacc accgcccac | 1380 |

```
cacctcctgg gaccacacca ctaccgcccc caaccacagc agagactagc agcggggcca    1440
cctccacaac caccaccaca agtgcacttg cccccgtggc cgccatcatc ccccgcccc     1500
ccgacgtcca gcccgtgatt gacaagctgg ccgagtatgt cgccaggaac ggcctgaagt   1560
tcgagaccag tgttcgtgcc aagaatgatc aaagatttga gttcctgcag ccgtggcacc   1620
agtataatgc ttattatgag tttaagaagc agttcttcct ccagaaagaa ggggcgata    1680
gcatgcaggt tgtgtctgca ccagaagagg ctcccacaga ctctgctccc gagaagccaa   1740
gtgatgctgg ggaggatggc gcgcctgaag acgcagccga ggtgggagca cgggcaggct   1800
caggcgggaa gaaggaggca tcgtccagta agaccgtccc ggacgggaag ctggtgaaag   1860
cttcctttgc tccaataagc tttgcaatca aggccaaaga aaatgatctg cttcccctgg   1920
aaaaaaatcg tgttaagcta gatgatgaca gtgatgatga tgaagaaagc aaagaaggcc   1980
aagaaagttc tagtagtgct gcaaacacta acccagcagt tgccccaccc tgtgtagttg   2040
ttgaggagaa gaagcctcaa cttacccagg aggagctaga agcaaagcaa gcaaagcaaa   2100
agctggaaga tcgcctcgca gctgctgccc gggaaaagct ggcccaggcg tctaaggagt   2160
caaaagagaa acagcttcaa gcagaacgta aaggaaagc ggcgttattt ttacagaccc    2220
tcaaaaatcc tctgccggaa gcagaagctg ggaaaattga ggagagtcct ttcagtgtcg   2280
aggaatccag cactacgccc tgccctctac tgactggagg caggcctctg cctactttag   2340
aagttaaacc acccgatagg ccttcgagca aaagcaaaga tccaccgaga gaagaagaga   2400
aagaaaagaa aaagaaaaag cacaaaaaaa gatctcgaac aagatcacgt tctcccaagt   2460
accattcgtc atccaagtcc aggtctagat cacactcaaa agcaaagcat tctcttccca   2520
gtgcctatcg gacagtgcgg cggtcgaggt cccgctcccg gtcccctcgg aggagagccc   2580
actcccctga gagacggagg gaagagagga gtgtgcccac tgcctaccgc gtgagccgca   2640
gccctggggc cagcaggaag cggacccgct ccagaagtcc ccacgagaag aagaagaaga   2700
ggcggtcccg gtcgcggacc aagtccaagg ccaggtctca gtcggtgtca cccagcaagc   2760
aggcagcgcc ccggcccgcg gccccgcgg cccactcggc gcactcagcc agcgtctccc    2820
ctgtggagag tcggggctcc agccaggagc gctccagggg agtctctcag gaaaaagaag   2880
cccagatctc ttcagcaatc gtttcttccg tgcagagcaa aatcactcag gatctcatgg   2940
ccaaagtcag agcgatgctt gcagcttcca aaaacctgca aaccagcgct tcctgagacg   3000
gggccagcgg aggcagagcc gggaggctgc gtgggcttct ggcaggctc acgcagacgc    3060
cggccacacc atccacctgg ccgcctccat ggacccttgg tggcttttgt aaattaattt   3120
ttgatgacat tttgagtttt aagatttctg accagcagtc tcttacctgt atatttgtaa   3180
atatatcatg tttctgtgaa aatgtattat gaaataaaat gggaggaaac accttttcta   3240
gctag                                                              3245
```

<210> SEQ ID NO 158
<211> LENGTH: 2136
<212> TYPE: DNA
<213> ORGANISM: Homo sapiens

<400> SEQUENCE: 158

```
gggaagaggc ggagaacaat atggcggatg gcgaggagcc ggagaagaaa agaaggagaa     60
tagaggagct gctggctgag aaaatggctg ttgatggtgg gtgtggggac actggagact    120
gggaaggtcg ctggaaccat gtaaagaagt tcctcgagcg atctggaccc ttcacacacc    180
ctgatttcga accgagcact gaatctctcc agttcttgtt agatacatgt aaagttctag    240
```

```
tcattggagc tggcggctta ggatgtgagc tcctgaaaaa tctggccttg tctggtttta      300
gacagattca tgttatagat atggacacta tagatgtttc caatctaaat aggcagtttt      360
tatttaggcc taaagatatt ggaagaccta aggctgaagt tgctgcagaa tttctaaatg      420
acagagttcc taattgcaat gtagttccac atttcaacaa gattcaagat tttaacgaca      480
ctttctatcg acaatttcat attattgtat gtggactgga ctctatcatc gccagaagat      540
ggataaatgg catgctgata tctcttctaa attatgaaga tggtgtctta gatccaagct      600
ccattgtccc tttgatagat ggggggacag aaggttttaa aggaaatgcc cgggtgattc      660
tgcctggaat gactgcttgt atcgaatgca cgctggaact ttatccacca caggttaatt      720
ttcccatgtg caccattgca tctatgccca ggctaccaga acactgtatt gagtatgtaa      780
ggatgttgca gtggcctaag gagcagcctt tggagaagg ggttccatta gatggagatg       840
atcctgaaca tatacaatgg attttccaaa atccctaga gagagcatca caatataata      900
ttaggggtgt tacgtatagg ctcactcaag gggtagtaaa aagaatcatt cctgcagtag      960
cttccacaaa tgcagtcatt gcagctgtgt gtgccactga ggttttttaaa atagccacaa     1020 gtgcatacat tcccttgaat aattacttgg tgtttaatga tgtagatggg ctgtatacat      1080
acacatttga agcagaaaga aggaaaaact gcccagcttg tagccagctt cctcaaaata      1140
ttcagttttc tccatcagct aaactacagg aggttttgga ttatctaacc aatagtgctt      1200
ctctgcaaat gaaatctcca gccatcacag ccaccctaga gggaaaaaat agaacacttt      1260
acttacagtc ggtaacctct attgaagaac gaacaaggcc aaatctctcc aaaacattga     1320
aagaattggg gcttgttgat ggacaagaac tggcggttgc tgatgtcacc accccacaga      1380
ctgtactatt caaacttcat tttacttctt aaggaaaatc tccacataat agaaaactca      1440
tggaaataat atactttgtg gatgctaaga agttgaatcg atgtcatttt tagcaatagt      1500
gttgccacga tttgtctttt tttatataat gaaccactct tttttaactt tgtaaccttc      1560
ccttgaagac agaattttgg tgttggtgct tgtaagcatt ttcattaata atatgagaaa      1620
tgatacctgg agagagagat tatgagcaaa tgtattgctt cttttagagg aggaagcata      1680
caacctcttt tgtgtgaatt ttgttattat ggtcaaagaa tgcattccta agttttcatt      1740
tgagtaccca aatacacaaa aggtgtccct ttaaggaaaa taagaattaa agttttaaat      1800
aacattacat tttacaatct gacatctgga gtatattgaa cataggctat ttcttgatat      1860
aacactcatt taattgtggc catccaaatg aatattattg cagaatttat cttgttcata      1920
atgatttgta aatggtgtta tagctgaata cctgtgcatg aaaatgggca atattttcat      1980
ctgtttactt gtagtgccat agaggccaat atgcacaata ttaactaatg ccaagacatg      2040
gctgtttaaa aaatttaatg ttcaaacagt tatcactgat gcttttgcac tatttattaa      2100
taaaatcata tattgtgtaa aaaaaaaaa aaaaaa                                 2136

<210> SEQ ID NO 159
<211> LENGTH: 671
<212> TYPE: DNA
<213> ORGANISM: Homo sapiens

<400> SEQUENCE: 159
aggcatcggc gcggtcagcc tcgtggcgcg cccacgcccc cacgccggct cttcccgggg       60
tccttccgtg cgcgttgata tgattggccg gcgaatcgtg gttctctttt cctccttggc      120
tgtctgaaga tagatcgcca tcatgaacga caccgtaact atccgcacta gaaagttcat      180
```

| | |
|---|---|
| gaccaaccga ctacttcaga ggaaacaaat ggtcattgat gtccttcacc ccgggaaggc | 240 |
| gacagtgcct aagacagaaa ttcgggaaaa actagccaaa atgtacaaga ccacaccgga | 300 |
| tgtcatcttt gtatttggat tcagaactca ttttggtggt ggcaagacaa ctggctttgg | 360 |
| catgatttat gattccctgg attatgcaaa gaaaaatgaa cccaaacata gacttgcaag | 420 |
| acatggcctg tatgagaaga aaaagacctc aagaaagcaa cgaaaggaac gcaagaacag | 480 |
| aatgaagaaa gtcaggggga ctgcaaaggc caatgttggt gctggcaaaa agtgagctgg | 540 |
| agattggatc acagccgaag gagtaaaggt gctgcaatga tgttagctgt ggccactgtg | 600 |
| gattttcgc aagaacatta ataaactaaa aacttcatgt gtctggttgt ttgaaaaaaa | 660 |
| aaaaaaaaaa a | 671 |

<210> SEQ ID NO 160
<211> LENGTH: 1110
<212> TYPE: DNA
<213> ORGANISM: Homo sapiens

<400> SEQUENCE: 160

| | |
|---|---|
| ctttccgctc ggctgttttc ctgcgcagga gccgcagggc cgtaggcagc catggcgccc | 60 |
| agccggaatg gcatggtctt gaagcccac ttccacaagg actggcagcg cgcgtggcc | 120 |
| acgtggttca accagccggc ccgtaagatc cgcagacgta aggcccggca agccaaggcg | 180 |
| cgccgcatcg ccccgcgccc ccgtcgggt cccatccggc ccatcgtgcg ctgccccacg | 240 |
| gttcggtacc acacgaaggt gcgcgccggc cgcggcttca gcctggagga gctcagggtg | 300 |
| gccggcattc acaagaaggt ggcccggacc atcggcattt ctgtggatcc gaggaggcgg | 360 |
| aacaagtcca cggagtccct gcaggccaac gtgcagcggc tgaaggagta ccgctccaaa | 420 |
| ctcatcctct tccccaggaa gccctcggcc ccaagaagg gagacagttc tgctgaagaa | 480 |
| ctgaaactgg ccacccagct gaccggaccg gtcatgcccg tccggaacgt ctataagaag | 540 |
| gagaaagctc gagtcatcac tgaggaagag aagaatttca agccttcgc tagtctccgt | 600 |
| atggcccgtg ccaacgcccg gctcttcggc atacgggcaa aagagccaa ggaagccgca | 660 |
| gaacaggatg ttgaaaagaa aaaataaagc cctcctgggg acttggaatc agtcggcagt | 720 |
| catgctgggt ctccacgtgg tgtgtttcgt gggaacaact gggcctggga tggggcttca | 780 |
| ctgctgtgac ttcctcctgc caggggattt ggggctttct tgaaagacag tccaagccct | 840 |
| ggataatgct ttactttctg tgttgaagca ctgttggttg tttggttagt gactgatgta | 900 |
| aaacggtttt cttgtgggga ggttacagag gctgacttca gagtggactt tgtgtttttc | 960 |
| tttttaaaga ggcaaggttg ggctggtgct cacagctgta atcccagcac tttgaggttg | 1020 |
| gctgggagtt caagaccagc ctggccaaca tgtcagaact actaaaaata aagaaatcag | 1080 |
| ccatgaaaaa aaaaaaaaaa aaaaaaaaaa | 1110 |

<210> SEQ ID NO 161
<211> LENGTH: 2439
<212> TYPE: DNA
<213> ORGANISM: Homo sapiens

<400> SEQUENCE: 161

| | |
|---|---|
| gagagcagcg gccgggaagg ggcggtgcgg gaggcgggt gtgggcggt agtgtgggcc | 60 |
| ctgttcctgc ccgcgcggtg ttccgcattc tgcaagcctc cggagcgcac gtcggcagtc | 120 |
| ggctccctcg ttgaccgaat caccgacctc tctccccagc tgtatttcca aaatgtcgct | 180 |
| ttctaacaag ctgacgctgg acaagctgga cgttaaaggg aagcgggtcg ttatgagagt | 240 |

| | |
|---|---|
| cgacttcaat gttcctatga agaacaacca gataacaaac aaccagagga ttaaggctgc | 300 |
| tgtcccaagc atcaaattct gcttggacaa tggagccaag tcggtagtcc ttatgagcca | 360 |
| cctaggccgg cctgatggtg tgcccatgcc tgacaagtac tccttagagc cagttgctgt | 420 |
| agaactcaaa tctctgctgg gcaaggatgt tctgttcttg aaggactgtg taggcccaga | 480 |
| agtggagaaa gcctgtgcca acccagctgc tgggtctgtc atcctgctgg agaacctccg | 540 |
| ctttcatgtg gaggaagaag ggaagggaaa agatgcttct gggaacaagg ttaaagccga | 600 |
| gccagccaaa atagaagctt tccgagcttc actttccaag ctaggggatg tctatgtcaa | 660 |
| tgatgctttt ggcactgctc acagagccca cagctccatg gtaggagtca atctgccaca | 720 |
| gaaggctggt gggtttttga tgaagaagga gctgaactac tttgcaaagg ccttggagag | 780 |
| cccagagcga cccttcctgg ccatcctggg cggagctaaa gttgcagaca gatccagct | 840 |
| catcaataat atgctggaca agtcaatga gatgattatt ggtggtggaa tggcttttac | 900 |
| cttccttaag gtgctcaaca acatggagat tggcacttct ctgtttgatg aagagggagc | 960 |
| caagattgtc aaagacctaa tgtccaaagc tgagaagaat ggtgtgaaga ttaccttgcc | 1020 |
| tgttgacttt gtcactgctg acaagtttga tgagaatgcc aagactggcc aagccactgt | 1080 |
| ggcttctggc atacctgctg gctggatggg cttggactgt ggtcctgaaa gcagcaagaa | 1140 |
| gtatgctgag gctgtcactc gggctaagca gattgtgtgg aatggtcctg tggggtatt | 1200 |
| tgaatgggaa gcttttgccc ggggaaccaa agctctcatg gatgaggtgg tgaaagccac | 1260 |
| ttctagggc tgcatcacca tcataggtgg tggagacact gccacttgct gtgccaaatg | 1320 |
| gaacacggag gataaagtca gccatgtgag cactgggggt ggtgccagtt tggagctcct | 1380 |
| ggaaggtaaa gtccttcctg gggtggatgc tctcagcaat atttagtact tcctgcctt | 1440 |
| ttagttcctg tgcacagccc ctaagtcaac ttagcatttt ctgcatctcc acttggcatt | 1500 |
| agctaaaacc ttccatgtca agattcagct agtggccaag agatgcagtg ccaggaaccc | 1560 |
| ttaaacagtt gcacagcatc tcagctcatc ttcactgcac cctggatttg catacattct | 1620 |
| tcaagatccc atttgaattt tttagtgact aaaccattgt gcattctaga gtgcatatat | 1680 |
| ttatattttg cctgttaaaa agaaagtgag cagtgttagc ttagttctct tttgatgtag | 1740 |
| gttattatga ttagctttgt cactgtttca ctactcagca tggaaacaag atgaaattcc | 1800 |
| atttgtaggt agtgagacaa aattgatgat ccattaagta aacaataaaa gtgtccattg | 1860 |
| aaaccgtgat ttttttttt ttcctgtcat actttgttag gaagggtgag aatagaatct | 1920 |
| tgaggaacgg atcagatgtc tatattgctg aatgcaagaa gtggggcagc agcagtggag | 1980 |
| agatgggaca attagataaa tgtccattct ttatcaaggg cctactttat ggcagacatt | 2040 |
| gtgctagtgc ttttattcta acttttattt ttatcagtta cacatgatca taatttaaaa | 2100 |
| agtcaaggct tataacaaaa aagccccagc ccattcctcc cattcaagat cccactccc | 2160 |
| cagaggtgac cactttcaac tcttgagttt ttcaggtata tacctccatg tttctaagta | 2220 |
| atatgcttat attgttcact tctttttttt ttattttta aagaaatcta tttcatacca | 2280 |
| tggaggaagg ctctgttcca catatatttc cacttcttca ttctctcggt atagttttgt | 2340 |
| cacaattata gattagatca aaagtctaca taactaatac agctgagcta tgtagtatgc | 2400 |
| tatgattaaa tttacttatg taaaaaaaa aaaaaaaa | 2439 |

MOLECULAR MARKERS FOR LUNG AND COLORECTAL CARCINOMAS

REFERENCE TO RELATED APPLICATION

The present application claims the priority to U.S. Provisional Application Ser. No. 61/099,008, filed Sep. 22, 2008, which is herein incorporated by reference in its entirety.

FIELD OF THE INVENTION

The present invention relates generally to tumor-associated molecular markers, and more specifically to tumor-associated molecular markers in peripheral blood.

BACKGROUND OF THE INVENTION

There are two main types of lung cancer, non-small cell lung cancer (NSCLC) and small cell lung cancer. NSCLC accounts for about 80% of lung cancers. Three most common types of NSCLC in the United States are adenocarcinoma/bronchoalveolar (35-40%), squamous cell carcinoma (25-30%) and large-cell carcinoma (10-15%). Lung cancer is most easily and successfully treated if it is caught early. An early-stage cancer is less likely to have grown to a large size or to have spread to other parts of the body (metastasized). Large or metastasized cancers are much more difficult to be treated.

Colorectal cancer, also called colon cancer or large bowel cancer, includes cancerous growths in the colon, rectum and appendix. It is the third most common form of cancer and the second leading cause of cancer-related death in the Western world. Many colorectal cancers are thought to arise from adenomatous polyps in the colon. These mushroom-shaped growths are usually benign, but some may develop into cancer over time. The majority of the time the diagnosis of localized colon cancer is through colonoscopy.

Diagnostic markers for early stage lung and colorectal cancers will have a significant impact on the morbidity and mortality of these diseases. Detection of cancer cell-specific biomarkers provides an effective screening strategy. It can also screen for and detect post-operative residual tumor cells, and for occult metastases, an early indicator of tumor recurrence. Early detection can thus improve survival in patients before symptoms are detectable clinically while undergoing treatment and while in remission. Certain markers were known in the art to make predictions of a patient's cancer risk using tumor tissues, however, it was not predicted nor predictable that the same markers could be detected in blood (see "DETAILED DESCRIPTION OF THE INVENTION; Detections of cancer gene markers in tissue versus blood samples").

Therefore, a heretofore unaddressed need exists in the art to address the aforementioned deficiencies and inadequacies, especially in connection with the method of detecting lung and/or colorectal cancers from peripheral blood samples.

SUMMARY OF THE INVENTION

One aspect of the invention relates to a method for detecting the presence and/or severity of lung and/or colorectal cancer. The method comprises:
(a) obtaining a test sample of bodily fluid comprising a nucleic acid from a subject;
(b) measuring the expression level of at least one cancer gene marker selected from:
  (i) the group consisting of: DUSP6, EIF2S3, GRB2, RNF4, MMD, MCM4, NF1 and MDM2; or
  (ii) the group consisting of: DUSP6, EIF2S3, MDM2, NF1, MMD, RNF4, GRB2, and EXT2;
(c) normalizing the expression level of the at least one cancer gene marker to a housekeeping gene;
(d) applying the normalized expression level of the at least one cancer gene marker to a logistic regression prediction model which calculates the probability of cancer and/or cancer recurrence risk; and
(e) determining the presence and/or severity of lung and/or colorectal cancer based oil the calculated probability.

In one embodiment of the invention, the test sample is a blood sample.

In another embodiment of the invention, the expression level of the at least one cancer gene marker is measured by performing a real-time polymerase chain reaction (real-time PCR).

In another embodiment of the invention, measuring step (b) quantifies the mRNA expression level by the cycle number of the test sample [Ct (test)], and wherein normalizing step (c) is performed by subtracting Ct (test) from the mRNA expression level of a housekeeping gene [Ct(HK)], to give a normalized mRNA expression level of the test sample [$^{\Delta}$Ct (test)].

In another embodiment of the invention, the housekeeping gene is selected from the group consisting of hypoxanthine phosphoribosyltransferase 1 (HPRT1) and glyceraldehyde-3-phosphate dehydrogenase (GAPDH).

In another embodiment of the invention, step (b) measures the expression level of DUSP6.

In another embodiment of the invention, step (b) measures the expression levels of the following six cancer gene markers: DUSP6, MDM2, NF1, EIF2S3, MMD, and RNF4.

In another embodiment of the invention, the at least one cancer gene marker is selected from the group consisting of DUSP6, EIF2S3, MDM2, NF1, MMD, RNF4, GRB2, and EXT2, and wherein step (e) determines the presence and/or severity of colorectal cancer.

In another embodiment of the invention, step (b) measures the expression level of at least (i) eight cancer gene markers; (ii) seven cancer gene markers; (iii) six cancer gene markers; (iv) five cancer gene markers; (v) four cancer gene markers; (vi) three cancer gene markers; or (vii) two cancer gene markers.

In another embodiment of the invention, step (b) measures the expression level of:
(i) the one gene marker: DUSP6;
(ii) the two gene markers: DUSP6 and EIF2S3;
(iii) the three gene markers: DUSP6, EIF2S3, and GRB2;
(iv) the four gene makers: DUSP6, EIF2S3, GRB2, and RNF4;
(v) the five gene makers: DUSP6, EIF2S3, GRB2, RNF4, and MMD;
(vi) the six gene makers: DUSP6, EIF2S3, GRB2, RNF4, MMD, and MCM4 or NF1;
(vii) the seven gene makers: DUSP6, EIF2S3, GRB2, RNF4, MMD, MCM4, and MDM2 or NF1;
(viii) the three gene markers: DUSP6, EIF2S3, and MDM2;
(ix) the four gene markers: DUSP6, EIF2S3, MDM2, and NF1;
(x) the five gene makers: DUSP6, EIF2S3, MDM2, NF1, and MMD;
(xi) the six gene makers: DUSP6, EIF2S3, MDM2, NF1, MMD, and RNF4;
(xii) the seven gene makers: DUSP6, EIF2S3, MDM2, NF1, MMD, RNF4, and GRB2; or
(xiii) the eight gene makers: DUSP6, EIF2S3, MDM2, NF1, MMD, RNF4, GRB2, and EXT2.

In another embodiment of the invention, the expression level of each cancer gene marker is measured by real-time polymerase chain reaction (real-time PCR) with a pair of primers selected from the group consisting of primer pairs 1 to 9 as follows:
  (i) DUSP6 (SEQ ID NO: 9)-specific primer pair 1: SEQ ID NOs: 137 and 138, or SEQ ID NOs. 139 and 140;
  (ii) EIF2S3 (SEQ ID NO: 1)-specific primer pair 2: SEQ ID NOs. 17 and 18, SEQ ID NOs. 19 and 20, SEQ ID NOs. 21 and 22, SEQ ID NOs. 23 and 24, SEQ ID NOs. 25 and 26, SEQ ID NOs. 27 and 28, SEQ ID NOs. 29 and 30, or SEQ ID NOs: 31 and 32;
  (iii) MDM2 (SEQ ID NO: 4)-specific primer pair 3: SEQ ID NOs: 75 and 76, SEQ ID NOs: 77 and 78, SEQ ID NOs: 79 and 80, or SEQ ID NOs: 81 and 82;
  (iv) NF1 (SEQ ID NO: 6)-specific primer pair 4: SEQ ID NOs: 97 and 98, SEQ ID NOs: 99 and 100, SEQ ID NOs: 101 and 102, SEQ ID NOs: 103 and 104, SEQ ID NOs: 105 and 106, SEQ ID NOs: 107 and 108, SEQ ID NOs: 109 and 110, SEQ ID NOs: 111 and 112, or SEQ ID NOs: 113 and 114;
  (v) MMD (SEQ ID NO: 7)-specific primer pair 5: SEQ ID NOs: 115 and 116, SEQ ID NOs: 117 and 118, or SEQ ID NOs: 119 and 120;
  (vi) RNF4 (SEQ ID NO: 8)-specific primer pair 6: SEQ ID NOs: 121 and 122, SEQ ID NOs: 123 and 124, SEQ ID NOs: 125 and 126, SEQ ID NOs: 127 and 128, SEQ ID NOs: 129 and 130, SEQ ID NOs: 131 and 132, SEQ ID NOs: 133 and 134, or SEQ ID NOs: 135 and 136;
  (vii) GRB2 (SEQ ID NO: 5)-specific primer pair 7: SEQ ID NOs: 83 and 84, SEQ ID NOs: 85 and 86, SEQ ID NOs: 87 and 88; SEQ ID NOs: 89 and 90, SEQ ID NOs: 91 and 92, SEQ ID NOs: 93 and 94, or SEQ ID NOs: 95 and 96;
  (viii) EXT2 (SEQ ID NO: 2)-specific primer pair 8: SEQ ID NOs: 33 and 34, SEQ ID NOs: 35 and 36, SEQ ID NOs: 37 and 38, SEQ ID NOs: 39 and 40, SEQ ID NOs: 41 and 42, SEQ ID NOs: 43 and 44, SEQ ID NOs: 45 and 46, SEQ ID NOs: 47 and 48, SEQ ID NOs: 49 and 50, or SEQ ID NOs: 51 and 52; and
  (ix) MCM4 (SEQ ID NO: 3)-specific primer pair 9: SEQ ID NOs: 53 and 54, SEQ ID NOs: 55 and 56, SEQ ID NOs: 57 and 58, SEQ ID NOs: 59 and 60, SEQ ID NOs: 61 and 62, SEQ ID NOs: 63 and 64, SEQ ID NOs: 65 and 66, SEQ ID NOs: 67 and 68, SEQ ID NOs: 69 and 70, SEQ ID NOs: 71 and 72, or SEQ ID NOs: 73 and 74.

In another embodiment of the invention, the EIF2S3 (SEQ ID NO: 1)-specific primer pair 2: SEQ ID NOs: 27, 28, and SEQ ID NOs: 31 and 32, the NF1 (SEQ ID NO: 6)-specific primer pair 4: SEQ ID NOs: 103, 104, and/or the GRB2 (SEQ ID NO: 5)-specific primer pair 7: SEQ ID NOs: 91, 92 are selected if step (e) determines the presence and/or severity of lung cancer, and are not selected if step (e) determines the presence and/or severity of colorectal cancer.

In another embodiment of the invention, the EIF2S3 (SEQ ID NO: 1)-specific primer pair 2: SEQ ID NOs: 19, 20, the NF1 (SEQ ID NO: 6)-specific primer pair 4: SEQ ID NOs: 113, 114, the EXT2 (SEQ ID NO: 2)-specific primer pair 8: SEQ ID NOs: 47, 48, and/or the MCM4 (SEQ ID NO: 3)-specific primer pair 9: SEQ ID NOs: 67 and 68 are selected if step (e) determines the presence and/or severity of colorectal cancer, and are not selected if step (e) determines the presence and/or severity of lung cancer.

Another aspect of the invention relates to a method for monitoring and/or assessing the prognosis of a patient's response to a cancer therapy. The method comprises the steps of:
  (a) obtaining samples of bodily fluid comprising a nucleic acid from the patient before and after receiving a cancer therapy for a lung and/or colorectal cancer;
  (b) measuring the expression level of at least one cancer gene marker selected from the group consisting of DUSP6, EIF2S3, GRB2, RNF4, MMD, MCM4, NF1, and MDM2;
  (c) normalizing the expression level of at least one cancer gene marker to a housekeeping gene;
  (d) applying the normalized expression level of at least one cancer gene marker to a logistic regression prediction model which calculates the probability of cancer and/or cancer recurrence risk; and
  (e) evaluating the response by comparing the calculated probabilities from the samples, and thereby monitoring and/or assessing the prognosis of a patient's response to a cancer therapy;
wherein a decrease in the probability after receiving the cancer therapy is indicative of a positive response to the therapy.

Another aspect of the invention relates to a method for monitoring and/or assessing the prognosis of a patient's response to a cancer therapy. The method comprises the steps of:
  (a) obtaining a first sample of bodily fluid comprising a nucleic acid from the patient before receiving a cancer therapy for a lung and/or colorectal cancer;
  (b) obtaining a second sample of bodily fluid comprising a nucleic acid from the patient after receiving the therapy;
  (c) measuring the expression level of at least one cancer gene marker selected from the group consisting of DUSP6, EIF2S3, GRB2, RNF4, MMD, MCM4, NF1, MDM2 in the first and second samples; and
  (d) comparing the measured expression levels in the first and second samples and thereby monitoring and/or assessing the prognosis of the patient's response to the cancer therapy; wherein:
    (i) an increase in the expression level(s) of DUSP6, GRB2, MCM4 and/or NF1 in the second sample as compared to the level(s) of the corresponding gene marker(s) in the first sample is an indication that the subject is at risk of developing lung cancer and/or lung cancer recurrence;
    (ii) an increase in the expression level of MDM2 in the second sample as compared to the level of the corresponding marker in the first sample is an indication that the subject is at risk of lung cancer recurrence; and
    (iii) an increase in the expression level of EIF2S3, MMD, and/or RNF4 in the second sample as compared to the level of the corresponding marker(s) in the first sample is an indication that the subject is not at risk of developing lung cancer.

Further another aspect of the invention relates to a method for detecting the presence and/or severity of lung and/or colorectal cancer. The method comprises:
  (a) obtaining a test sample of bodily fluid comprising a nucleic acid from a subject;
  (b) measuring the expression level of at least one cancer gene marker selected from:
    (i) the group consisting of: DUSP6, EIF2S3, GRB2, RNF4, MMD, MCM4, NF1, and MDM2; or
    (ii) the group consisting of: DUSP6, EIF2S3, MDM2, NF1, MMD, RNF4, GRB2, and EXT2; and
  (c) comparing the expression level of at least one cancer gene marker to an expression level of a corresponding cancer gene marker in a sample of bodily fluids from a non-cancerous control, and thereby detecting the presence and/or severity of lung and/or colorectal cancer; wherein:
    (i) an increase in the expression level of DUSP6, GRB2, MCM4 and/or NF1 in the test sample as compared to the level of the corresponding marker in the control is an indication that the subject is at risk of developing lung cancer;

(ii) an increase in the expression level of MDM2 in the test sample as compared to the level of the corresponding marker in the control is an indication that the subject is at risk of lung cancer recurrence;

(iii) a decrease in the expression level of EIF2S3, MMD, and/or RNF4 in the test sample as compared to the level of the corresponding marker in the control is an indication that the subject is at risk of developing lung cancer;

(iv) an increase in the expression level of DUSP6, GRB2, MDM2 and/or NF1 in the test sample as compared to the level of the corresponding marker in the control is an indication that the subject is at risk of developing colorectal cancer; and (v) a decrease in the expression level of EIF2S3, MMD, EXT2, and/or RNF4 in the test sample as compared to the level of the corresponding marker in the control is an indication that the subject is at risk of developing colorectal cancer.

The method may further comprises (a) normalizing the expression level of at least one cancer gene marker to a housekeeping gene; (b) applying the normalized expression level of at least one cancer gene marker to a logistic regression prediction model which calculates the probability of cancer and/or cancer recurrence risk; and (c) determining the presence and/or severity of lung and/or colorectal cancer based on the calculated probability.

Further another aspect of the invention relates to a kit for use in the aforementioned method for detecting the presence and/or severity of lung and/or colorectal cancer. The kit comprises one or more than one primer pair selected from the group consisting of cancer gene marker-specific primer pairs as follows:

(i) a DUSP6 (SEQ ID NO: 9)-specific primer pair;
(ii) an EIF2S3 (SEQ ID NO: 1)-specific primer pair;
(iii) an MDM2 (SEQ ID NO: 4)-specific primer pair;
(iv) a NF1 (SEQ ID NO: 6)-specific primer pair;
(v) an MMD (SEQ ID NO: 7)-specific primer pair;
(vi) an RNF4 (SEQ ID NO: 8)-specific primer pair;
(vii) a GRB2 (SEQ ID NO: 5)-specific primer pair;
(viii) an EXT2 (SEQ ID NO: 2)-specific primer pair; and
(ix) an MCM4 (SEQ ID NO: 3)-specific primer pair Yet another aspect of the invention relates to a kit for use in the aforementioned method for detecting the presence and/or severity of lung and/or colorectal cancer. The kit comprises one or more than one primer pair selected from the group consisting of cancer gene marker-specific primer pairs 1-9 as follows:

(i) DUSP6 (SEQ ID NO: 9)-specific primer pair 1: SEQ ID NOs. 137 and 138, or SEQ ID NOs. 139 and 140;

(ii) EIF2S3 (SEQ ID NO: 1)-specific primer pair 2: SEQ ID NOs. 17 and 18, SEQ ID NOs. 19 and 20, SEQ ID NOs. 21 and 22, SEQ ID NOs. 23 and 24, SEQ ID NOs. 25 and 26, SEQ ID NOs. 27 and 28, SEQ ID NOs. 29 and 30, or SEQ ID NOs: 31 and 32;

(iii) MDM2 (SEQ ID NO: 4)-specific primer pair 3: SEQ ID NOs: 75 and 76, SEQ ID NOs: 77 and 78, SEQ ID NOs: 79 and 80, or SEQ ID NOs: 81 and 82;

(iv) NF1 (SEQ ID NO: 6)-specific primer pair 4: SEQ ID NOs: 97 and 98, SEQ ID NOs: 99 and 100, SEQ ID NOs: 101 and 102, SEQ ID NOs: 103 and 104, SEQ ID NOs: 105 and 106, SEQ ID NOs: 107 and 108, SEQ ID NOs: 109 and 110, SEQ ID NOs: 111 and 112, or SEQ ID NOs: 113 and 114;

(v) MMD (SEQ ID NO: 7)-specific primer pair 5: SEQ ID NOs: 115 and 116, SEQ ID NOs: 117 and 118, or SEQ ID NOs: 119 and 120;

(vi) RNF4 (SEQ ID NO: 8)-specific primer pair 6: SEQ ID NOs: 121 and 122, SEQ ID NOs: 123 and 124, SEQ ID NOs: 125 and 126, SEQ ID NOs: 127 and 128, SEQ ID NOs: 129 and 130, SEQ ID NOs: 131 and 132, SEQ ID NOs: 133 and 134, or SEQ ID NOs: 135 and 136;

(vii) GRB2 (SEQ ID NO: 5)-specific primer pair 7: SEQ ID NOs: 83 and 84, SEQ ID NOs: 85 and 86, SEQ ID NOs: 87 and 88; SEQ ID NOs: 89 and 90, SEQ ID NOs: 91 and 92, SEQ ID NOs: 93 and 94, or SEQ ID NOs: 95 and 96;

(viii) EXT2 (SEQ ID NO: 2)-specific primer pair 8: SEQ ID NOs: 33 and 34, SEQ ID NOs: 35 and 36, SEQ ID NOs: 37 and 38, SEQ ID NOs: 39 and 40, SEQ ID NOs: 41 and 42, SEQ ID NOs: 43 and 44, SEQ ID NOs: 45 and 46, SEQ ID NOs: 47 and 48, SEQ ID NOs: 49 and 50, or SEQ ID NOs: 51 and 52; and (ix) MCM4 (SEQ ID NO: 3)-specific primer pair 9: SEQ ID NOs: 53 and 54, SEQ ID NOs: 55 and 56, SEQ ID NOs: 57 and 58, SEQ ID NOs: 59 and 60, SEQ ID NOs: 61 and 62, SEQ ID NOs: 63 and 64, SEQ ID NOs: 65 and 66, SEQ ID NOs: 67 and 68, SEQ ID NOs: 69 and 70, SEQ ID NOs: 71 and 72, or SEQ ID NOs: 73 and 74.

The kit may further comprise a primer pair 10 that is specific to a housekeeping gene.

In one embodiment of the invention, the kit further comprises an HPRT1-specific primer pair 10: SEQ ID NOs: 153 and 154.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
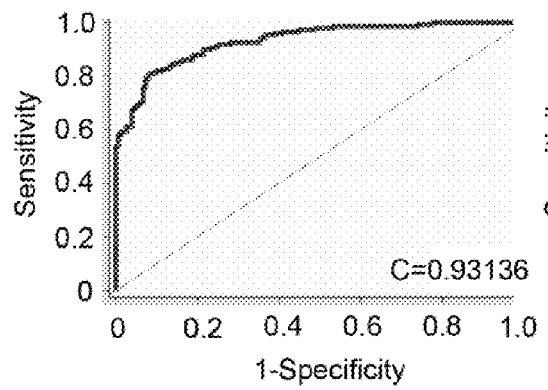
FIG. 1 is a graph of a receiver operating characteristic (ROC) curve for the prediction model PM-7 (N=300) with Area under curve (AUC) of 0.93136.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "gene" as used herein refers to a locatable region of genomic sequence. In cells, a gene is a portion of DNA that contains both "coding" sequences that determine what the gene does, and "non-coding" sequences that determine when the gene is active (expressed). A gene is a union of genomic sequences encoding a coherent set of potentially overlapping functional products. The molecules resulting from gene expression, whether RNA or protein, are known as gene products.

The term "genetic marker" as used herein refers to alteration in DNA that may indicate an increased risk of developing a specific disease or disorder.

The term "gene expression" means the production of a protein or a functional RNA from its gene.

The term "gene signature" or "Genetic signatures" are characteristic patterns of gene activity in cells.

As used herein, a "housekeeping gene" is a typically a constitutive gene that is transcribed at a relatively constant level across many or all known conditions. The housekeeping gene's products are typically needed for maintenance of the cell. It is generally assumed that their expression is unaffected by experimental conditions. Housekeeping genes that have been tested by applicants of this invention using clinical tumor/normal tissues, spike-in cultured cancer cells in the blood of healthy person, or clinical blood samples (lung cancer and controls) are GAPDH (glyceraldehyde 3-phosphate dehydrogenase; NM_002046; SEQ ID NO: 155), YWHAH (tyrosine 3-monooxygenase/tryptophan 5-monooxygenase activation protein, eta polypeptide; NM_003405; SEQ ID NO: 156), SFRS8 (Homo sapiens splicing factor, arginine/serine-rich 8 (suppressor-of-white-apricot homolog, *Drosophila*; NM_004592; SEQ ID NO: 157), UBA3 (Ubiquitin-activating enzyme 3; NM_003968; SEQ ID NO: 158), RPS24 (ribosomal protein S24; NM_033022; SEQ ID NO: 159), RPL13 (ribosomal protein L13; NM_000977; SEQ ID NO: 160) PGK1 (phosphoglycerate kinase 1; NM_000291; SEQ ID NO: 161) (Also see Dheda et al. (2004) *Biotechniques* 37(1): 112-4, 116, 118-9; Human Reference Gene Panel (Roche); Vandesompele et al. (2002) *Genome Biology* 3(7):research0034.1-0034.11).

The term "prognosis" means a forecasting of the probable course and outcome of a disease, esp. of the chances of recovery.

The term "primer" refers to a strand of nucleic acid that serves as a starting point for DNA replication.

The term "overexpressed" refers to a state wherein there exists any measurable increase over normal or baseline levels. For example, a molecule that is overexpressed in a disease is one that is manifested in a measurably higher level in the presence of the disease than in the absence of the disease.

The term "underexpressed" refers to a state wherein there exists any measurable decrease over normal or baseline levels. For example, a molecule that is underexpressed in a disease is one that is manifested in a measurably lower level in the presence of the disease than in the absence of the disease.

The terms "detecting" and "diagnosing" are used interchangeably.

The term "normal tissue samples" or "control" refers to lung or colorectal tissue and/or body fluid from a subject determined to be negative for lung or colorectal cancer.

The terms "individual," "host," "patient," and "subject," used interchangeably herein, refer to a mammal, including, but not limited to, murines, simians, humans, non-human primates, felines, canines, equines, bovines, porcines, and ovines.

Detections of Cancer Gene Markers in Tissue Versus Blood Samples

The invention relates to detection of cancer-associated nucleic acid in blood samples using real time-PCR assays. The discoveries of a panel of gene markers that may be measured in blood samples for detecting lung and/or colorectal cancer risks are unexpected. It has been known that certain cancer gene markers in tumor tissues may be used for predicting a patient's cancer risk. It was, however, not predicted nor predictable that the same markers could be detected in blood samples (See U.S. application Ser. No. 11/437,607. which is incorporated by reference in its entirety) discloses a list of 12 genes (with Hazard Ratio greater than 1) that were thought to be "RISK" factors and thus tested in blood samples. The four risk genes for lung cancer prognosis, HGF, HMMR, ErbB3 and DLG2, resulted in much lower expression levels of mRNA because their Ct values were each greater than 30. In addition, these four genes sometimes were not measurable in blood samples. Furthermore, it was unexpected that the experimental results showed that two genes, MMD, RNF4, seemed to play a protective role in the logistic regression model of the current application (See U.S. application Ser. No. 11/437,607).

Further proofs that cancer markers in the tissue samples are not predicted nor predictable in the blood samples are the following: EIF2S3 was considered to be a protective gene in the present prediction models in blood assays, while it was as a risk gene for metastasis of lung cancer when the test was performed on tissue samples. MCM4 was identified as a tumor-associated marker in lung cancer tissue. It was deemed to be a risk factor in blood studies for lung cancer, but seemed to act protectively in the full model of colorectal cancer (Table 14). The expression level GRB2was positively correlated to the metastasis of lung cancer. The relative transcript of GRB2 gene represented a risk for lung cancer and colorectal cancer based on the odds ratio in Tables 4 and 9, but acted as a protective factor in the full model of colorectal cancer (Table 14). CPEB4 acted as a risk factor in the tissue sample studies, but a protective factor in the blood sample assays (Table 14). POLDIP2 was selected as a protective gene in the tissue sample studies, but a risk factor in the blood sample assays (Table 14).

Thus, the gene markers disclosed herein as cancer markers in blood samples for diagnosis and predictions of cancer risks are unexpected results.

Lung and Colorectal Cancer-Associated Genetic Markers

The invention relates to identification and applications of genetic signatures for detecting, diagnosing lung and/or colorectal cancers, monitoring therapeutic response, and prognosis prediction, such as recurrence possibility. Expression levels of lung and colorectal cancer gene markers were detected and measured in blood samples from patients and controls.

In one embodiment, expression levels of 8 genetic markers were examined in the blood samples using real-time PCR. Three genes, DUSP6, MCM4 and NF1, showed higher expression in the blood samples collected from the lung and/or colorectal cancer patients, which indicated that these three genes were associated with lung and/or colorectal cancers. Therefore, they can serve as genetic markers for predicting the risk of lung and/or colorectal cancer. Using statistical approach based on the mRNA expression levels of the 8 genes, several prediction models were built to predict the risk of one getting lung and/or colorectal cancer. Table 1 lists lung and colorectal cancer gene markers.

TABLE 1

| Lung and colorectal cancer-associated gene marker | | SEQ |
|---|---|---|
| Full name | Symbol | ID NO |
| Eukaryotic translation initiation factor 2, subunit 3 gamma | EIF2S3 | 1 |
| Exostoses (multiple) 2 | EXT2 | 2 |
| Minichromosome maintenance complex component 4 | MCM4 | 3 |
| Mdm2, transformed 3T3 cell double minute 2, p53 binding protein (mouse) | MDM2 | 4 |
| Growth factor receptor-bound protein 2 | GRB2 | 5 |
| Neurofibromin 1 (neurofibromatosis, von Recklinghausen disease, Watson disease) | NF1 | 6 |
| Monocyte to macrophage differentiation-associated | MMD | 7 |
| Ring finger protein 4 | RNF4 | 8 |
| Dual specificity phosphatase 6 | DUSP6 | 9 |
| Cytoplasmic polyadenylation element binding protein 4 | CPEB4 | 10 |
| Wee+ (*S. pombe*) homolog | WEE1 | 11 |
| Interferon regulatory factor 4 | IRF4 | 12 |
| Signal transducer and activator of transcription 2, 113 kD | STAT2 | 13 |
| zinc finger protein 264 | ZNF264 | 14 |
| DNA polymerase delta interacting protein 2 | POLDIP2 | 15 |
| Hypoxanthine phosphoribosyltransferase 1* | HPRT1 | 16 |

Expression of cancer gene markers can be detected by a variety of means including reverse transcription polymerase chain reaction (RT-PCR), real-time RT-PCR, TAQMAN assay, Northern blotting, in situ hybridization, and microarray technology.

PCR primers may be designed to be specific for the polynucleotide of genetic markers disclosed. Alternatively, primers may be designed to cross react with related polynucleotides, e.g., to allow hybridization to variants of cancer genetic markers. PCR-based assays of transcript expression profiles of genes may detect a single polynucleotide or multiple polynucleotides simultaneously ("multiplex" PCR). The amplified products may be detected by electrophoresis. Individual PCR products corresponding to cancer genetic markers may be identified by electrophoretic mobility. Alternatively, a PCR primer may be labeled for detecting PCR products. A primer comprising a fluorescent label may be used and the PCR product detected by detecting fluorescence. Where multiple polynucleotides are detected simultaneously, a mixture of primers each with a distinct label may be used in a PCR reaction. The products produced are detected based on the label. For example, fluorescent labels each with unique emission spectra may be used for labeling primers.

Polynucleotides expressed by the cancer marker genes may be detected by SAGE and by Massively Parallel Signature Sequencing (MPSS). See e.g., Brenner et al., "Gene expression analysis by massively parallel signature sequencing (MPSS) on microbead arrays," Nature Biotechnology 18: 630-34 (2000).

Prediction Models

Statistical analysis of expression profiling of investigated genes may be used to predict the risk of an individual getting lung and/or colorectal cancers. An odds ratio (OR) is used as an estimate of the relative risk for lung and/or colorectal cancer. The odds ratio is a measure of effect size, describing the strength of association or non-independence between two binary data values. It is used as a descriptive statistic and plays an important role in logistic regression.

The odds ratio is defined as the ratio of the odds of an event occurring in one group to the odds of it occurring in another group. In statistics, the odds is the probability of an event occurring divided by the probability of an event not occurring. The odds ratio is a way of comparing whether the probability of a certain event is the same for two groups. An odds ratio of 1 implies that the event is equally likely to occur in both groups. An odds ratio greater than one implies that the event is more likely to occur in the first group. An odds ratio less than one implies that the event is less likely to occur in the first group.

If the probabilities of the event in each of the groups are $p_1$ (first group) and $p_2$ (second group), then the odds ratio is:

$$\frac{p_1/(1-p_1)}{p_2/(1-p_2)}$$

Logistic regression (sometimes called the logistic model or logit model) is used for prediction of the probability of occurrence of an event by fitting data to a logistic curve. The logistic regression model gives the probability that the response occurs as an exponential function of independent variables. The model is written in terms of a probability (P), which is in the range from 0 to 1.

The logistic regression begins with the logistic function:

$$f(Y) = \frac{1}{1 + \exp^{-Y}} = P$$

The "input" is Y and the "output" is f(Y), i.e., P. The output is confined to values between 0 and 1. The variable Y represents the exposure to some set of risk factors, while f(Y) represents the probability (P) of a particular outcome, given that set of risk factors. The variable Y is a measure of the total contribution of all the risk factors used in the model and is known as the logit. The variable Y is usually defined as $Y=\beta_0+\beta_1 x_1+\beta_2 x_2+ \ldots +\beta_k x_k$, where $\beta_0$ is called the "intercept" and $\beta_1$, $\beta_2$, $\beta_3$, and so on, are called the "regression coefficients" of $x_1$, $x_2$, $x_3$, respectively. The intercept is the value of Y when the value of all risk factors is zero (i.e., the value of z in someone with no risk factors). Each of the regression coefficients describes the size of the contribution of that risk factor. A positive regression coefficient means that that risk factor increases the probability of the outcome, while a negative regression coefficient means that risk factor decreases the probability of that outcome; a large regression coefficient means that the risk factor strongly influences the probability of that outcome; while a near-zero regression coefficient means that that risk factor has little influence on the probability of that outcome. Logistic regression is a useful way of describing the relationship between one or more risk factors and an outcome.

In the present invention, a person will be suspected of having "lung or colorectal cancer", if the calculated probability (P) is greater than 0.5. However, the setting of the cutoff value for probability for having a higher sensitivity or specificity of prediction model can be achieved.

Further, the clinical performance of a laboratory test can be described in terms of diagnostic accuracy, or the ability to correctly classify subjects into clinically relevant subgroups (Zweig and Campbell, 1993, Receiver-Operating Characteristic (ROC) plots. Clinical Chemistry 39:561-577). Terms commonly used for evaluation of clinical performances of a diagnostic test include sensitivity, specificity, efficiency, accuracy, utility, usefulness, and efficacy.

ROC plots may be used. ROC plots provide a pure index of accuracy by demonstrating the limits of a test's ability to discriminate between alternative states of health over the complete spectrum of operating conditions. A ROC curve is a graphical plot of the sensitivity vs. (1-specificity) for a binary classifier system as its discrimination threshold is varied (FIG. 1). The ROC curve can also be presented equivalently by plotting the fraction of true positives (TPR=true positive rate) vs. the fraction of false-positives (FPR=false positive rate). The closer a ROC curve is to the upper left-hand corner of the graph, the more accurate it is, because the true-positive rate is 1 and the false-positive rate is 0. ROC curves are useful for evaluating the clinical utility of a diagnostic test based on a molecular marker.

The value of the area under the ROC curve (AUC) indicates the tests' ability (prediction model) to discriminate the disease (lung or colorectal cancer) group from normal subjects. The greater is the AUC, the better is the diagnostic test. Generally, the AUC of 0.7 to 0.8 is a marginally useful test, 0.8 to 0.9 is a good test, and those tests with an area greater than 0.9 are excellent (Nakamur et al. (2004), "Cancer Diagnostics, Current and Future Trends" Humana Press, Totowa, N.J., USA; p 403).

These tumor markers can further be used in combination, e.g., in a panel or a prediction model that comprises two or more markers. A panel of 3, 4, 5, 6, 7, 8, 9, 10, 11, 12, 13, 14 or 15 markers may be used. It is likely that many lung cancers will overexpress at least one of the gene markers DUSP6, MDM2, MCM4, NF1 and GRB2, and/or underexpress at least one of the markers EIF2S3, MMD and RNF4, and many colorectal cancers will overexpress at least one of MDM2, GRB2, NF1 and DUSP6. and/or underexpress at least one of EIF2S3, EXT2, MMD and RNF4. Thus, combining these markers into a prediction model will provide a comprehensive screen for certain cancers.

A kit may contain, in separate containers, one or more primer pairs comprising polynucleotides sequences that are complementary to the mRNAs of genes comprising nucleotide sequences of SEQ ID NO: 1-9 or at least 90% identical to the nucleotide sequences of SEQ ID NO: 1-9.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Procedures for Blood Test for Lung and Colorectal Cancer Molecular Markers

Preparation of mononuclear cells. Peripheral blood (5-8 ml) collected from lung and colorectal cancer patients, and healthy subjects was used to isolate mononuclear cell (MNC) fraction using BD VACUTAINER® CPT™ tube (BD, USA) according to the manufacturer instructions. The MNC fraction was supplemented with PBS buffer with three volumes of the original whole blood sample and followed by centrifugation at 2000 rpm for 10 min. The MNC fraction was further washed with 1 ml of PBS followed by centrifugation at 2000 rpm for 5 min. The final pellet was supplemented with 2 ml of Super RNAPURE™ reagent (contained in SUPER-RNAPURE™ kit, Genesis, Taiwan).

Real-time PCR analysis of cancer marker gene expression. Total RNA was extracted from the MNC fraction using Super RNAPURE™ kit according to the manufacturer's instructions. The RNA pellet was dissolved in DEPC-treated water and stored at −80° C. until use. The RNA quality was ascertained with gel electrophoresis using 1% agarose and also with $OD_{260}/OD_{280}$ ratio greater than 1.7. Around 1 μg of total RNA was used for cDNA synthesis with random hexamer primers (Amersham Bioscience, UK) and SUPERSCRIPT™II reverse transcriptase (Invitrogen, USA). The reaction mixture and conditions for reverse transcription reaction were according to the manufacturer's instructions.

Table 1 lists 16 genes that were chosen as lung and colorectal cancer molecular markers for real-time PCR analysis of mRNA expression level. They are: (1) eukaryotic translation initiation factor 2, subunit 3 gamma, 52 kDa (EIF2S3), (2) exostoses (multiple) 2 (EXT2), (3) minichromosome maintenance complex component 4 (MCM4), (4) Mdm2, transformed 3T3 cell double minute 2, p 53 binding protein (mouse) (MDM2), (5) growth factor receptor-bound protein 2 (GRB2), (6) neurofibromin 1 (neurofibromatosis, von Recklinghausen disease, Watson disease) (NF1), (7) monocyte to macrophage differentiation-associated (MMD), (8) ring finger protein 4 (RNF4), (9) dual specificity Is phosphatase 6 (DUSP6), (10) cytoplasmic polyadenylation element binding protein 4 (CPEB4), (11) wee+ (S. pombe) homolog (WEE1), (12) interferon regulatory factor 4 (IRF4), (13) signal transducer and activator of transcription 2, 113 kD (STAT2), (14) zinc finger protein 264 (ZNF264), (15) DNA polymerase delta interacting protein 2 (POLDIP2), and (16) hypoxanthine phosphoribosyltransferase 1 (HPRT1).

Real-time PCR analysis of mRNA expression level of each gene was performed using Roche LIGHTCYCLER® 1.5 according to the manufacturer instructions. A total volume of 20 μl reaction mixture contained 20-100 ng of cDNA, primer, Probe (Universal ProbeLibrary probe), and Master Mix LIGHTCYCLER® TaqMan® Master Mix (Roche, Germany). Amplification was performed after 10 min at 95° C., which was followed by 40 cycles of 5 sec at 95° C., 20 sec at 60° C., and with a final extension at 72° C. for 1 sec. The control was performed for each batch by performing RT-PCR on a reaction mixture without cDNA to confirm no contamination in the assay.

Table 2 lists the primer pairs and probes used for synthesizing each of the amplicons in RT-PCR. The combination of a gene-specific primer pair and a nucleotide probe selected from UNIVERSAL PROBELIBRARY™ (F. Hoffmann-La Roche Ltd, Basel, Switzerland) could generate mores gene-specific amplicon during the Real-time PCR assay.

TABLE 2

| Gene (SEQ ID NO.) | Positions of amplicon | Forward Primer | SEQ ID NO. | Reverse Primer | SEQ ID NO. | Probe No.* |
|---|---|---|---|---|---|---|
| EIF2S3 (1) | 1143-1388 | EIF2S3-F17 | 17 | EIF2S3-R18 | 18 | 47 |
| | 477-554 | EIF2S3-F19 | 19 | EIF2S3-R20 | 20 | 30 |
| | 4-111 | EIF2S3-F21 | 21 | EIF2S3-R22 | 22 | 78 |
| | 310-423 | EIF2S3-F23 | 23 | EIF2S3-R24 | 24 | 32 |
| | 989-1056 | EIF2S3-F25 | 25 | EIF2S3-R26 | 26 | 1 |
| | 778-853 | EIF2S3-F27 | 27 | EIF2S3-R28 | 28 | 76 |
| | 2071-2194 | EIF2S3-F29 | 29 | EIF2S3-R30 | 30 | 72 |
| | 1784-1872 | EIF2S3-F31 | 31 | EIF2S3-R32 | 32 | 2, 30, 51, 75 |
| EXT2 (2) | 1255-1502 | EXT2-F33 | 33 | EXT2-R34 | 34 | 85 |
| | 1639-1747 | EXT2-F35 | 35 | EXT2-R36 | 36 | 37 |
| | 1208-1275 | EXT2-F37 | 37 | EXT2-R38 | 38 | 69 |
| | 2471-2543 | EXT2-F39 | 39 | EXT2-R40 | 40 | 22 |
| | 2359-2444 | EXT2-F41 | 41 | EXT2-R42 | 42 | 49 |
| | 2403-2488 | EXT2-F43 | 43 | EXT2-R44 | 44 | 76 |
| | 2484-2593 | EXT2-F45 | 45 | EXT2-R46 | 46 | 77 |
| | 2483-2591 | EXT2-F47 | 47 | EXT2-R48 | 48 | 31 |
| | 1471-1585 | EXT2-F49 | 49 | EXT2-R50 | 50 | 76 |
| | 1756-2037 | EXT2-F51 | 51 | EXT2-R52 | 52 | 43 |
| MCM4 (3) | 2071-2164 | MCM4-F53 | 53 | MCM4-R54 | 54 | 42 |
| | 1326-1410 | MCM4-F55 | 55 | MCM4-R56 | 56 | 64 |
| | 1022-1097 | MCM4-F57 | 57 | MCM4-R58 | 58 | 9 |
| | 2263-2375 | MCM4-F59 | 59 | MCM4-R60 | 60 | 20 |
| | 429-524 | MCM4-F61 | 61 | MCM4-R62 | 62 | 33 |
| | 1572-1667 | MCM4-F63 | 63 | MCM4-R64 | 64 | 41 |
| | 1609-1728 | MCM4-F65 | 65 | MCM4-R66 | 66 | 47 |
| | 588-648 | MCM4-F67 | 67 | MCM4-R68 | 68 | 84 |
| | 1988-2115 | MCM4-F69 | 69 | MCM4-R70 | 70 | 74 |
| | 563-743 | MCM4-F71 | 71 | MCM4-R72 | 72 | 84 |
| | 892-1102 | MCM4-F73 | 73 | MCM4-R74 | 74 | 9 |
| MDM2 (4) | 218-425 | MDM2-F75 | 75 | MDM2-R76 | 76 | 68 |
| | 598-667 | MDM2-F77 | 77 | MDM2-R78 | 78 | 18 |
| | 256-318 | MDM2-F79 | 79 | MDM2-R80 | 80 | 68 |
| | 852-988 | MDM2-F81 | 81 | MDM2-R82 | 82 | 21 |
| GRB2 (5) | 313-535# | GRB2-F83 | 83 | GRB2-R84 | 84 | 66 |
| | 599-674## | GRB2-F85 | 85 | GRB2-R86 | 86 | 7 |
| | 503-591## | GRB2-F87 | 87 | GRB2-R88 | 88 | 21 |
| | 799-868### | GRB2-F89 | 89 | GRB2-R90 | 90 | 66 |
| | 420-502### | GRB2-F91 | 91 | GRB2-R92 | 92 | 13 |
| | 504-612## | GRB2-F93 | 93 | GRB2-R94 | 94 | 29 |
| | 635-745## | GRB2-F95 | 95 | GRB2-R96 | 96 | 6 |
| NF1 (6) | 5509-5581 | NF1-F97 | 97 | NF1-R98 | 98 | 56 |
| | 1560-1619 | NF1-F99 | 99 | NF1-R100 | 100 | 9 |
| | 6233-6302 | NF1-F101 | 101 | NF1-R102 | 102 | 60 |
| | 583-655 | NF1-F103 | 103 | NF1-R104 | 104 | 61 |
| | 3475-3547 | NF1-F105 | 105 | NF1-R106 | 106 | 84 |
| | 7293-7367 | NF1-F107 | 107 | NF1-R108 | 108 | 6 |
| | 2314-2391 | NF1-F109 | 109 | NF1-R110 | 110 | 18 |
| | 10791-10883 | NF1-F111 | 111 | NF1-R112 | 112 | 81 |
| | 8538-8665 | NF1-F113 | 113 | NF1-R114 | 114 | 21 |
| MMD (7) | 279-365 | MMD-F115 | 115 | MMD-R116 | 116 | 19 |
| | 749-822 | MMD-F117 | 117 | MMD-R118 | 118 | 19 |
| | 671-761 | MMD-F119 | 119 | MMD-R120 | 120 | 65 |
| RNF4 (8) | 514-623 | RNF4-F121 | 121 | RNF4-R122 | 122 | 43 |
| | 322-397 | RNF4-F123 | 123 | RNF4-R124 | 124 | 22 |
| | 416-515 | RNF4-F125 | 125 | RNF4-R126 | 126 | 67 |
| | 377-478 | RNF4-F127 | 127 | RNF4-R128 | 128 | 38 |
| | 96-205 | RNF4-F129 | 129 | RNF4-R130 | 130 | 1 |
| | 524-607 | RNF4-F131 | 131 | RNF4-R132 | 132 | 75 |
| | 755-1010 | RNF4-F133 | 133 | RNF4-R134 | 134 | 16 |
| | 548-756 | RNF4-F135 | 135 | RNF4-R136 | 136 | 43 |
| DUSP6 (9) | 789-912 | DUSP6-F137 | 137 | DUSP6-R138 | 138 | 66 |
| | 1117-1331 | DUSP6-F139 | 139 | DUSP6-R140 | 140 | 22 |
| CPEB4 (10) | 3169-3308 | CPEB4-F141 | 141 | CPEB4-R142 | 142 | 33 |
| WEE1 (11) | 2745-2994 | WEE1-F143 | 143 | WEE1-R144 | 144 | 56 |
| IRF4 (12) | 1247-1345 | IRF4-F145 | 145 | IRF4-R146 | 146 | 55 |

TABLE 2-continued

| Gene (SEQ ID NO.) | Positions of amplicon | Forward Primer/ SEQ ID NO. | | Reverse Primer/ SEQ ID NO. | | Probe No.* |
|---|---|---|---|---|---|---|
| STAT2 (13) | 1868-1960 | STAT2-F147 | 147 | STAT2-R148 | 148 | 68 |
| ZNF264 (14) | 478-594 | ZNF264-F149 | 149 | ZNF264-R150 | 150 | 79 |
| POLDIP2 (15) | 788-941 | POLDIP2-F151 | 151 | POLDIP2-R152 | 152 | 20 |
| HPRT1** (16) | 218-319 | HPRT1-F153 | 153 | HPRT1-R154 | 154 | 73 |

*Probe No. indicates Universal ProbLibrary probe ™ number.
**HPRT1 serves as a reference gene.
Sequence of primer 184-1R (SEQ ID NO. 149) is perfect match to variant 2 (NM_203506), with one mismatch at 5' end to variant 1 (SEQ ID NO. 5, NM_002086). Both variant mRNAs could be amplified using 184-1F/184-1R primer pair.
Only variant 1 (SEQ ID NO. 5, NM_002086) could be amplified using the primer pair.
Both variant mRNAs (SEQ ID No. 5, NM_002086 and NM_203506) could get the same amplicon.

Example 2

Blood Test for Lung Cancer-Associated Molecular Markers

Materials and Methods

Blood sample collections from lung cancer patients. One hundred fifty patients with histologically confirmed lung cancer were enrolled at 3 hospitals in this study. Forty lung cancer patients among them were enrolled at the National Taiwan University Hospital (Taipei, Taiwan; Area A), 30 patients at the Tri-Service General Hospital (Taipei, Taiwan; Area A), and 80 patients at the Taichung Veterans General Hospital (Taichung, Taiwan; Area B) between April 2006 and March 2007. The last group included 28 patients with recurrence of lung cancer. Tables 3 lists the detailed clinicopathological features of all (n=150) and new incidents of lung cancer patients (n=122). All patients were enrolled in a prospective investigational protocol approved by the Institutional Review Board (IRB) of each hospital, respectively.

Eight milliliters of peripheral blood per patient was collected using BD VACUTAINER® CPT™ tube (BD, USA). Preparation of MNC from blood samples, total RNA extraction and RT-PCR analysis of cancer marker gene expression were performed according to the methods disclosed in Example 1.

Data normalization and statistical analysis. Real-time or quantitative PCR (qPCR) techniques rely on the ability to detect the PCR product at each cycle during the exponential phase. Real-time instrumentation, which couples fluorescence detection and thermal cycling, measures the change of signal (in relative fluorescence units, RFU) at every cycle. Results obtained during the exponential phase give the best estimate of the amount of starting material. An amplification threshold is set within the early exponential phase. The cycle number at which the amplification curve crosses this threshold is the cycle threshold (Ct) of the sample. The Ct value decreases linearly with an increasing quantity of the input DNA template and can be used as a quantitative measure of mRNA expression of a gene analyzed.

TABLE 3

| | | Characteristic | | | |
|---|---|---|---|---|---|
| | | First cohort All lung cancer patients | | Second cohort New lung cancer patients | |
| | Area | A | B | A | B |
| Patient No. (%) | | 70 | 80 | 70 | 52 |
| Age (Mean ± SD) | | 66.3 ± 12.6 | 63.4 ± 12.8 | 66.3 ± 12.6 | 63.5 ± 12.6 |
| Gender | Male | 39 (26%) | 54 (36%) | 39 (32%) | 37 (31%) |
| | Female | 31 (21%) | 26 (17%) | 31 (25%) | 15 (12%) |
| Stage | I | 13 (9%) | 15 (10%) | 13 (11%) | 7 (6%) |
| | II | 2 (1%) | 12 (8%) | 2 (1%) | 9 (7%) |
| | III | 22 (15%) | 23 (15%) | 22 (18%) | 12 (10%) |
| | IV | 33 (22%) | 30 (20%) | 33 (27%) | 24 (20%) |
| Cell Type | Adenocarcinomas | 51 (34.0%) | 56 (37.3%) | 51 (72.9%) | 38 (73.1%) |
| | Squamous cell carcinomas | 9 (6.0%) | 16 (10.7%) | 9 (12.8%) | 7 (13.5%) |
| | Other NSCLC* | 5 (3.3%) | 1 (0.7%) | 5 (7.1%) | 1 (1.9%) |
| | SCLC** | 1 (0.7%) | 0 | 1 (1.5%) | 0 |
| | Others | 4 (2.6%) | 7 (4.7%) | 4 (5.7%) | 6 (11.5%) |

*NSCLC stands for non-small cell lung cancer.
**SCLC stands for small cell lung cancer.

Control samples. Seventy eight peripheral blood samples were collected from normal volunteers consisting of 28 males and 50 females with an average age of 60.9±11.0 in Area A (Taipei, Taiwan). In Area B (Taichung, Taiwan), 72 peripheral blood samples were collected from normal volunteers (without clinical cancer disease) consisting of 24 males and 48 females with an average age of 55.3±9.3. Informed consent of each sample donor was obtained.

Relative quantities of mRNA expression for each gene were used for statistical analysis using Statistical program SAS version 9.1.3 Service Pack 3. Data were normalized as follows: $^{\Delta}Ct(test)=Ct(HK)-Ct(test)$, where Ct (test) stands for the cycle number of a gene analyzed, Ct(HK) stands for the cycle number of the endogenous housekeeping gene HPRT1 (HK).

Results

A chi-square test and analysis of variance (ANOVA) were used to analyze the data. ANOVA gives a statistical test of whether the means of several groups are all equal and determines whether any significant differences exist among two or more groups of subjects on one or more factors. Messenger RNA expression levels of all investigated genes in the control group were shown to be significantly correlated with geographical parameters, while only the mRNA expression levels of EIF2S3, MDM2, and DUSP6 in lung cancer patients were significantly correlated. In this study, "geographical" effect was controlled because the control group's blood samples were collected in the same two "geographical" areas as those of the lung cancer patient group.

Multiple logistic regression was applied to evaluate the correlation between gene expression level and lung cancer since more than one independent variable was included in the prediction equation. The data from the first and second cohort studies were analyzed separately for statistical significance.

The first cohort had a sample number (N) of 300, including 150 lung cancer patients (new and recurrent cases) and 150 controls. The statistic results from the first study cohort indicated that the mRNA expression levels of the following seven genes significantly correlated (p<0.05) with lung cancer: EIF2S3, MCM4, MDM2, GRB2, MMD, RNF4 and DUSP6 (Table 4).

In Table 4, an OR greater than 1 indicates that a patient with a relatively high mRNA expression level of investigated gene, such as MCM4, MDM2, GRB2 or DUSP6, is more likely classified under the lung cancer group. The OR of 11.873 for mRNA expression level of GRB2 gene means a person in the lung cancer group is over 10 times more likely to develop lung cancer than a person in the control group, where $^\Delta Ct(test)$ for GRB2 mRNA is increased by one unit. An OR less than 1 indicates a person with a relatively high mRNA expression level of EIF2S3, MMD or RNF4 genes is less likely to develop lung cancer.

The second cohort had a sample number (N) of 272, including 122 new incidents of lung cancer and the same control group (150) as the first cohort's. The second cohort included only new cases without the 28 recurrent cases. The OR from the second study cohort indicated that the following seven genes significantly correlated with lung cancer: EIF2S3, MCM4, GRB2, NF1, MMD RNF4 and DUSP6. Of these genes, 6 genes except the NF1 gene showed the correlation in both study cohorts (Table 4). The MCM4, GRB2, NF1 and DUSP6 genes with relatively higher mRNA expression levels were considered as risk factors for lung cancer, while EIF2S3, MMD, and RNF4 genes were considered as protective genes (Table 4).

The mRNA expression level of MDM2 was significantly associated with the 28 recurrent cases of lung cancer, which indicated that the MDM2 gene expression might be correlated with the lung cancer recurrence. A comparison of statistical analysis of the first and second study cohort data indicated that the NF1 gene expression might more likely correlate with the occurrence of lung cancer.

TABLE 4

| Gene | SEQ ID NO. | First cohort N = 300 | | Second cohort N = 272 | |
|---|---|---|---|---|---|
| | | OR* | P value | OR | P value |
| EIF2S3 | 1 | 0.053 | <0.0001 | 0.004 | <0.0001 |
| MCM4 | 3 | 2.999 | 0.0024 | 2.252 | 0.0293 |
| MDM2 | 4 | 2.528 | 0.0272 | — | — |
| GRB2 | 5 | 11.873 | <0.0001 | 14.724 | <0.0001 |
| NF1 | 6 | — | — | 4.628 | 0.007 |
| MMD | 7 | 0.443 | 0.0004 | 0.326 | <.0001 |

TABLE 4-continued

| Gene | SEQ ID NO. | First cohort N = 300 | | Second cohort N = 272 | |
|---|---|---|---|---|---|
| | | OR* | P value | OR | P value |
| RNF4 | 8 | 0.147 | <0.0001 | 0.160 | <0.0001 |
| DUSP6 | 9 | 5.301 | <0.0001 | 8.722 | <0.0001 |

*OR stands for odds ratio.

Example 3

Gene Signature and Prediction of Clinical Outcome in Lung Cancer

Prediction models were generated based on the mRNA expression levels of investigated genes for predicting the risk of getting lung cancer, evaluating therapeutic response to a particular drug or treatment. Equations for prediction models were derived by using a step-wise variable selection method of multiple regression approach and with the criteria of p-value less than 0.1.

The DUSP6 gene was chosen first by the statistical analysis program using logistic regression to form a prediction model for N=300 and N=272. The gene EIF2S3 was then added to the prediction model for the same analysis. Other significant genes were serially added and processed as mentioned above until the optimal validity indexes were fulfilled for the study cohorts of N=300 and N=272, such as sensitivity>80%, specificity>85%, accuracy>85% and AUC (area under the ROC)>0.9.

Table 5 shows calculations of validity indices, such as sensitivity, specificity and accuracy. When a person is tested for cancer, the test outcome can be either positive (sick) or negative (healthy). Sensitivity=(No. of True Positives)/(No. of True Positives+False Negatives); Specificity=(No. of True Negatives)/(No. of True Negatives+False Positives); Accuracy=(No. of True Positives+No. of True Negatives)/(No. of True Positives+False Negatives+False Positives+True Negatives).

TABLE 5

| | | Condition (e.g., disease) as determined by "Gold" standard | |
|---|---|---|---|
| | | True | False |
| Test outcome | Positive | True Positive (TP) | False Positive (FP) | Positive Predictive Value (PPV) |
| | Negative | False Negative (FN) | True Negative (TN) | Negative Predictive Value (NPV) |
| | | Sensitivity | Specificity | Accuracy |

One-Gene Signature: DUSP6

An increase in the relative mRNA expression level of the DUSP6 gene was detected in the peripheral blood samples of lung cancer patients, but not in the samples from normal controls. An elevated mRNA expression level of DUSP6 was highly associated with lung cancer for both study cohorts. In addition, the odds ratio of 5.3 and 8.7 for the mRNA expression level of the DUSP6 gene (Table 4) means that a person with a relatively higher mRNA expression level of the DUSP6 gene is about 5- and 9-times more at risk of developing lung cancer than a person with lower gene expression in study cohort N=300 and N=272, respectively.

The measurement of the DUSP6 gene mRNA expression is sufficient as a single variable in the prediction model PM-1 and PM-8 for the study cohorts N=300 and N=272, respectively. Both models delivered good validity indexes, such as sensitivity=69-72%, specificity=80-83%, accuracy=72-77%, and AUC=79-81% (Tables 6 and 7). These results indicated that the relative mRNA expression level of the DUSP6 gene can be potentially used as a molecular index for detection of lung cancer because an AUC of 0.8 to 0.9 is generally considered as a good test.

The DUSP6 gene can be further applied as a prognostic marker (index) for monitoring the therapeutic response, recurrence, and survival because the higher mRNA quantity of DUSP6 was consistently found in peripheral blood samples obtained from lung cancer patients, but not in the samples obtained from normal controls. For example, a reduction in the mRNA expression of the DUSP6 gene can be a direct or an indirect result from a positive therapeutic response or as an indication for a lower possibility of recurrence, better prognosis, and a longer survival period.

TABLE 6

Prediction models (PM) for study cohort n = 300 based on multiple regression analysis with step-wise approach

| Model ID | Gene Set for Prediction Model (PM) | SEQ ID NO: | Sensitivity % | Specificity % | Accuracy % | AUC |
|---|---|---|---|---|---|---|
| PM-1 | DUSP6 | 9 | 72.0 | 80.0 | 72.0 | 0.79013 |
| PM-2 | DUSP6, EIF2S3 | 9, 1 | 77.3 | 80.7 | 79.0 | 0.86998 |
| PM-3 | DUSP6, EIF2S3, GRB2 | 9, 1, 5 | 78.0 | 86.0 | 82.0 | 0.89249 |
| PM-4 | DUSP6, EIF2S3, GRB2, RNF4 | 9, 1, 5, 8 | 82.0 | 88.7 | 85.3 | 0.90824 |
| PM-5 | DUSP6, EIF2S3, GRB2, RNF4, MMD, | 9, 1, 5, 8, 7 | 81.3 | 88.0 | 84.7 | 0.91849 |
| PM-6 | DUSP6, EIF2S3, GRB2, RNF4, MMD, MCM4 | 9, 1, 5, 8, 7, 3 | 82.7 | 88.7 | 85.7 | 0.92676 |
| PM-7 | DUSP6, EIF2S3, GRB2, RNF4, MMD, MCM4, MDM2 | 9, 1, 5, 8, 7, 3, 4 | 82 | 88.0 | 85.0 | 0.93136 |

The prediction model equations were as follow:
(1) PM-1: $Y = -2.9954 + 1.5474 \times DUSP6$;
(2) PM-2: $Y = 2.2095 + 2.0365 \times DUSP6 - 1.7257 \times EIF2S3$;
(3) PM-3: $Y = 1.4289 + 1.4017 \times DUSP6 - 2.5814 \times EIF2S3 + 1.9511 \times GRB2$;
(4) PM-4: $Y = 3.1608 + 1.5836 \times DUSP6 - 2.7234 \times EIF2S3 + 2.5838 \times GRB2 - 1.3237 \times RNF4$;
(5) PM-5: $Y = 3.5445 + 1.7293 \times DUSP6 - 2.3917 \times EIF2S3 + 2.7266 \times GRB2 - 1.6062 \times RNF4 - 0.7211 \times MMD$;
(6) PM-6: $Y = 6.0403 + 1.7820 \times DUSP6 - 2.4374 \times EIF2S3 + 2.5568 \times GRB2 - 1.8151 \times RNF4 - 0.7617 \times MMD + 1.0296 \times MCM4$;
(7) PM-7: $Y = 9.0793 + 1.6680 \times DUSP6 - 2.9325 \times EIF2S3 + 2.4742 \times GRB2 - 1.9206 \times RNF4 - 0.8141 \times MMD + 1.0983 \times MCM4 + 0.9274 \times MDM2$.

TABLE 7

Prediction models (PM) for study cohort n = 272 based on multiple regression analysis with step-wise approach

| Model ID | Gene Set for Prediction Model (PM) | SEQ ID NO: | Sensitivity % | Specificity % | Accuracy % | AUC |
|---|---|---|---|---|---|---|
| PM-8 | DUSP6 | 9 | 69.7 | 83.3 | 77.2 | 0.81328 |
| PM-9 | DUSP6, EIF2S3 | 9, 1 | 76.2 | 86.7 | 82.0 | 0.87221 |
| PM-10 | DUSP6, EIF2S3, GRB2 | 9, 1, 5 | 73.0 | 87.3 | 80.9 | 0.89423 |
| PM-11 | DUSP6, EIF2S3, GRB2, RNF4 | 9, 1, 5, 8 | 79.5 | 90.7 | 85.7 | 0.90623 |
| PM-12 | DUSP6, EIF2S3, GRB2, RNF4. MMD | 9, 1, 5, 8, 7 | 78.7 | 88.7 | 84.2 | 0.92383 |
| PM-13 | DUSP6, EIF2S3, GRB2, RNF4, MMD, NFI | 9, 1, 5, 8, 7, 6 | 78.7 | 88.0 | 83.8 | 0.92948 |
| PM-14 | DUSP6, EIF2S3, GRB2, RNF4, MMD, NFI, MCM4 | 9, 1, 5, 8, 7, 6, 3 | 80.3 | 90.0 | 85.7 | 0.93448 |

The prediction model equations were as follow:
(1) PM-8: $Y = -3.8260 + 1.8525 \times DUSP6$;
(2) PM-9: $Y = 1.4569 - 1.7287 \times EIF2S3 + 2.3448 \times DUSP6$;
(3) PM-10: $Y = 0.6016 - 2.4501 \times EIF2S3 + 1.7576 \times GRB2 + 1.7607 \times DUSP6$;
(4) PM-11: $Y = 2.1254 - 2.5506 \times EIF2S3 + 2.3450 \times GRB2 - 1.2167 \times RNF4 + 1.8972 \times DUSP6$;
(5) PM-12: $Y = 2.7212 - 2.2022 \times EIF2S3 + 2.5379 \times GRB2 - 0.8757 \times MMD - 15887 \times RNF4 + 2.1095 \times DUSP6$;
(6) PM-13: $Y = 4.7530 - 3.1491 \times EIF2S3 + 1.5388 \times NFI + 2.8198 \times GRB2 - 1.1177 \times MMD - 1.7172 \times RNF4 + 2.1433 \times DUSP6$;
(7) PM-14: $Y = 6.7266 - 3.2199 \times EIF2S3 + 0.8119 \times MCM4 + 1.5322 \times NFI + 2.6894 \times GRB2 - 1.1209 \times MMD - 1.8324 \times RNF4 + 2.1659 \times DUSP6$.

Two-Gene Signature: DUSP6, EIF2S3

The EIF2S3 gene was chosen to improve the prediction performances for both study cohorts. The relative mRNA expression level of EIF2S3 gene seemed to be negatively correlated with the incidence of lung cancer. An extremely low odds ratio (0.004 and 0.053, Table 4) for the EIF2S3 gene indicated that an increase in one unit of $^\Delta$Ct(test) can result in a reduction of 99.6% ($=(1-0.004)\times100\%$) and 94.7% ($=(1-0.053)\times100\%$) probability for having lung cancer in the study cohort of N=272 and N=300, respectively.

The prediction models PM-2 and PM-9 each contained two molecular markers, EIF2S3 and DUSP6 genes, to discriminate lung cancer patients and non-cancer control samples with a high specificity. 87% for PM-9 and 81% for PM-2. The three validity indexes sensitivity, accuracy, and AUC of both models using a two-gene signature were increased about 6-9% as compared to the models using one-gene signature (Tables 6 and 7).

Using a two-gene signature prediction model gave a better specificity than a one-gene signature prediction model for the study cohort of N=272, while the specificity remained the same for the study cohorts of N=300.

The value of the area under the ROC curve (AUC=0.86998 for N=300; AUC=0.87221 for N=272) for the prediction model using a two-gene signature presented an assay with a good diagnostic accuracy. Potential clinical utilities should include applications for detecting lung cancer, monitoring the therapeutic response and prognosis, such as the recurrence possibility within a certain follow-up period and survival.

Three-Gene Signature: DUSP6, EIF2S3, GRB2

The prediction model using a 3-gene signature (PM-3) gave an increased validity indexes in the study cohort of N=300 as compared to that using a two-gene signature (PM-2, Table 6). In the study cohort of N=272, however, the prediction model using a three-gene signature (PM-10) only slightly improved the specificity as compared to that using a two-gene signature (PM-9) (Table 7).

A higher AUC, LIP to 0.89, of both models based on a three-gene signature indicated an increased potential for clinical uses in detecting lung cancer, monitoring the therapeutic response and prognosis, such as the recurrence possibility within a certain follow-up period and survival.

Four-Gene Signature: DUSP6, EIF2S3, GRB2, RNF4

The mRNA expression level of the RNF4 gene was negatively correlated with lung cancer and was the fourth significant factor added to the modeling (PM-4 and PM-11; Tables 6 and 7). The odds ratios of 0.147 and 0.16 for the RNF4 gene in N=300 and N=272 cohorts indicated that the probability of having lung cancer can reduce 85.3%, i.e., $(1-0.147)\times100\%$, and 84%, i.e., $(1-0.16)\times100\%$, respectively, with an increase by one unit of $^\Delta$Ct(test).

A lung cancer patient can be accurately discriminated from a non-cancerous individual by models based on a 4-gene signature since the AUC in both models were greater than 0.9, which is generally considered as an excellent test. Other validity indexes of both models also met the performance of a good diagnostic test, such as 80-82% sensitivity, 89-91% specificity, and 86% accuracy (Tables 6 and 7).

The potential clinical uses of a four-gene signature include development of tests for detecting lung cancer, monitoring the therapeutic response and prognosis, such as the recurrence possibility within a certain follow-up period and survival.

Five-Gene Signature: DUSP6, EIF2S3, GRB2, RNF4, MMD

The gene MMD was added as the fifth cancer-associated molecular marker to form the prediction model PM-5 and PM-12 (Tables 6 and 7). The relative mRNA expression levels of MMD, EIF2S3 and RNF4 genes were negatively correlated with lung cancer, since the OR was 0.443, 0.053 and 0.147 for N=300 cohort and 0.326, 0.004 and 0.160 for N=272 cohort, respectively (Table 4). These genes should therefore be considered as protective genes for lung cancer in their predictive models.

The diagnostic performance of a five-gene signature in both prediction models (PM-5 and PM-12) was slightly improved as compared to the models using a four-gene signature (PM-4 and PM-11). Only the AUC value increased from 0.908 to 0.918 for N=300 and from 0.906 to 0.923 for N=272 cohorts, whereas other validity indexes, sensitivity, specificity and accuracy in both models were almost the same. The five-gene signature can also be applied to develop tests for detecting lung cancer, monitoring the therapeutic response and prognosis, such as the recurrence possibility within a certain follow-up period and survival.

Six-Gene Signature: DUSP6, EIF2S3, GRB2, RNF4, MMD, MCM4/or NF1

The gene MCM4 was selected as the sixth cancer-associated market in the prediction model PM-6 for the study cohort of N=300, while the gene NF1 was added in the prediction model PM-13 for the study cohort of N=272. Based on the OR of 2.999 for N=300 and 2.252 for N=272 cohorts, a person with an increase by one unit of $^\Delta$Ct(test) for the relative mRNA expression of MCM4 gene was 2-3 times more at risk of developing lung cancer. The higher mRNA expression of NF1 gene was also represented as a risk factor for lung cancer disease.

The diagnostic performance of the prediction model PM-6 was slightly better than PM-5 for the study cohort of N=300 as to an increased sensitivity, specificity, accuracy and AUC (Table 6). The prediction model PM-13 for the study cohort of N=272 showed almost the same performance as the prediction model PM-12 (Table 7). Both six-gene signature prediction models can potentially be used for the development of clinical tests for detecting lung cancer, monitoring the therapeutic response and prognosis, such as the recurrence possibility within a certain follow-up period and survival.

Seven-Gene Signature: DUSP6, EIF2S3, GRB2, RNF4, MMD, MCM4 and MDM2 or NF1

The gene MDM2 was the seventh molecular marker added to the aforementioned 6 genes, DUSP6, EIF2S3, GRB2, RNF4, MMD and MCM4, in the prediction model PM-7 for the study cohort of N=300 using logistic multiple regression (Table 6). The higher mRNA expression of the MDM2 gene was significantly correlated to lung cancer only when the study cohort included recurrent and new incident cases. It, however, disappeared from the list of significant molecular factors after removal of recurrent cases. The result indicated that the mRNA expression level of the MDM2 gene might play a special role in the progression of lung cancer recurrence.

Based on the study cohort of N=300, the prediction model PM-7 using a seven-gene signature was optimized for clearly discriminating those lung cancer patients from normal controls with an excellent diagnostic performance, such as 82% sensitivity, 88% specificity, 85% accuracy and an estimated AUC of 0.93136. FIG. 1 shows the ROC curve for the prediction model PM-7 and the value of the estimated area (C).

The prediction model PM-14 for the study cohort of N=272 contained seven lung cancer-associated molecular markers: DUSP6, EIF2S3, GRB2, RNF4, MMD, NF1 and MCM4 genes (Table 7). A higher mRNA expression level of the NF1 gene appeared to be a significant risk factor for lung cancer based on the study cohort of N=272, which included only new cases of lung cancer.

The prediction model PM-14 showed an excellent diagnostic performance with 80% sensitivity, 90% specificity, 86% accuracy and an estimated AUC of 0.93448, similar to that of the prediction model PM-7. The validity indexes such as specificity and AUC of the prediction model PM-14 were slightly higher than those of the prediction model PM-7

Figure 2:
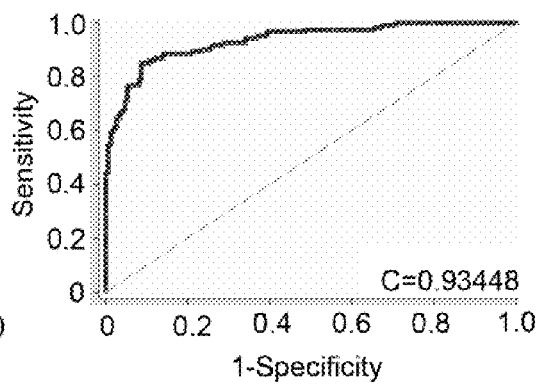
FIG. 2 is a graph of an ROC curve for prediction model PM-14 for N=272 with AUC=0.93448.

(Table 7). FIG. 2 shows the ROC curve for the prediction model PM-7 and the value of the estimated area under the ROC curve (AUC).

Example 4

Procedures for Blood Test for Colorectal Cancer-Associated Molecular Markers

Fifty patients with histologically confirmed colorectal cancer were enrolled in a prospective investigational protocol, which was approved by the Institutional Review Board at the Cheng Hsin Rehabilitation Medical Center (Taipei, Taiwan). Table 8 lists the detailed clinicopathological features of the patients.

Eight milliliters of peripheral blood of each patient was collected using BD VACUTAINER® CPT™ tubes (BD, USA). For control samples, statistical analysis was performed on assay data of 78 peripheral blood samples of normal volunteers (without clinical cancer) collected in Taipei (Taiwan). The control group contained 28 males and 50 females with an average age of 60.9±11.0.

Total RNA was extracted from blood samples and cDNA was then synthesized as described in Example 1. The mRNA expression of sixteen genes EIF2S3, EXT2, MCM4, MDM2, GRB2, NF1, MMD, RNF4, DUSP6, CPEB4, WEE1, IRF4, STAT2, ZNF264, POLDIP2, and HPRT1 (as reference gene) in each sample was quantified using real-time PCR assay as described in Example 1. Data normalization and statistical analysis of experimental data were performed as described in Example 2.

TABLE 8

Clinicopathologic Characteristic of all colorectal cancer patients (N = 50)

| Characteristic | No. of Patients (%) |
|---|---|
| Area A | 50 (100%) |
| Age(Mean ± SD) | 66.3 ± 12.6 |
| Gender | |
| Male | 29 (58%) |
| Female | 21 (42%) |
| Stage | |
| I | 10 (20%) |
| II | 10 (20%) |
| III | 15 (30%) |
| IV | 11 (22%) |
| Others | 4 (8%) |

Results

Chi-square test and analysis of variance (ANOVA) of the mRNA expression levels of investigated genes obtained from the colorectal cancer patient group and from the control group were performed to examine the correlation and independency of variants.

Age and gender-associated gene expression was identified neither in colorectal cancer group nor in control group. The effects derived from the geographical factor were excluded because both control and colorectal cancer samples were collected in the same geographical area.

The mRNA expression levels of EIF2S3, MDM2, GRB2, NF1, MMD, RNF4, and DUSP6 significantly correlated with colorectal cancer with p-value<0.05 (Table 9). Although the p-value for the mRNA expression level of the EXT2 gene was 0.06, close to 0.05, it was used as a colorectal cancer-associated molecular marker for modeling.

An odds ratio greater than 1 indicates that an individual with a higher mRNA expression level of an investigated gene such as MDM2, GRB2, NF1 or DUSP6 is more likely to develop colorectal cancer than an individual with a lower expression level of the same gene. An odds ratio of less than 1 indicates that an individual with a lower mRNA expression level of an investigated gene such as EIF2S3, EXT2, MMD, or RNF4 is more likely to develop colorectal cancer. In other words, the higher mRNA expression levels of MDM2, GRB2, NF1 and DUSP6 genes in peripheral blood samples were considered as risk factors for colorectal cancer, while the higher mRNA expression of EIF2S3, EXT2, MMD and RNF4 genes seemed to play a protective role.

TABLE 9

Colorectal cancer-associated genetic markers

| Gene | SEQ ID NO: | OR | P value |
|---|---|---|---|
| EIF2S3 | 1 | 0.006 | <0.0001*** |
| EXT2 | 2 | 0.240 | 0.0623 |
| MDM2 | 4 | 17.745 | 0.0009** |
| GRB2 | 5 | 6.993 | 0.0153* |
| NF1 | 6 | 42.825 | 0.0032** |
| MMD | 7 | 0.223 | 0.0003** |
| RNF4 | 8 | 0.195 | 0.0117* |
| DUSP6 | 9 | 5.309 | 0.0019** |

*p < 0.05;
**p < 0.01;
***p < 0.001

Example 5

Gene Signatures for Colorectal Cancer

The statistical approach used for predicting colorectal cancer, evaluating the therapeutic response and prognosis was as described in Example 2. Briefly, the prediction models were derived based on the mRNA expression of investigated genes. Equations for prediction models were derived by using a step-wise variable selection method of multiple regression approach and with the criteria of p-value<0.1 (Table 9). The DUSP6 gene was chosen as the first gene by the statistical analysis program to form a prediction model. Then the EIF2S3 gene was added to the prediction model to perform the same analysis procedures. Other significant genes were serially added and processed as mentioned above until optimal validity indexes were fulfilled, such as >80% sensitivity, >85% specificity, >85% accuracy and an AUC (area under the ROC ) of >0.9 (Table 10).

TABLE 10

Prediction models (PM) for study cohort n = 128 based on multiple regression analysis with step-wise approach

| Model ID | Gene Set for Prediction Model | SEQ ID NO: | Sensitivity % | Specificity % | Accuracy % | AUC |
|---|---|---|---|---|---|---|
| PM-15 | DUSP6 | 9 | 58.0 | 82.1 | 72.7 | 0.77077 |
| PM-16 | DUSP6, EIF2S3 | 9, 1 | 64.0 | 84.6 | 76.6 | 0.82615 |

TABLE 10-continued

Prediction models (PM) for study cohort n = 128
based on multiple regression analysis with step-wise approach

| Model ID | Gene Set for Prediction Model | SEQ ID NO: | Sensitivity % | Specificity % | Accuracy % | AUC |
|---|---|---|---|---|---|---|
| PM-17 | DUSP6, EIF2S3, MDM2 | 9, 1, 4 | 74.0 | 87.2 | 82.0 | 0.88679 |
| PM-18 | DUSP6, EIF2S3, MDM2, NF1 | 9, 1, 4, 6 | 70.0 | 87.2 | 80.5 | 0.90641 |
| PM-19 | DUSP6, EIF2S, MDM2, NF1, MMD | 9, 1, 4, 6, 7 | 74.0 | 89.7 | 83.6 | 0.91962 |
| PM-20 | DUSP6, EIF2S3, MDM2, NF1, MMD, RNF4 | 9, 1, 4, 6, 7, 8 | 80.0 | 89.7 | 85.9 | 0.93795 |
| PM-21 | DUSP6, EIF2S3, MDM2, NF1, MMD, RNF4, GRB2 | 9, 1, 4, 6, 7, 8, 5 | 74.0 | 91.0 | 84.4 | 0.94410 |
| PM-22 | DUSP6, EIF2S3, MDM2, NF1, MMD, RNF4, GRB2, EXT2 | 9, 1, 4, 6, 7, 8, 5, 2 | 76.0 | 88.5 | 83.6 | 0.94551 |

The prediction model equations were as follows.
(1) PM-15: $Y = -3.5600 + 1.5766 \times DUSP6$;
(2) PM-16: $Y = 1.8263 - 1.5721 \times EIF2S3 + 1.6581 \times DUSP6$;
(3) PM-17: $Y = 8.5768 - 2.9997 \times EIF2S3 + 2.5961 \times MDM2 + 1.2722 \times DUSP6$;
(4) PM-18: $Y = 9.1597 - 3.9042 \times EIF2S3 + 1.9563 \times MDM2 + 2.4926 \times NF1 + 1.3385 \times DUSP6$;
(5) PM-19: $Y = 9.9823 - 3.9749 \times EIF2S3 + 1.8787 \times MDM2 + 2.8088 \times NF1 - 0.7192 \times MMD + 1.6132 \times DUSP6$;
(6) PM-20: $Y = 14.9816 - 4.0103 \times EIF2S3 + 2.5131 \times MDM2 + 2.6702 \times NF1 - 1.1964 \times MMD - 1.7016 \times RNF4 + 2.0085 \times DUSP6$;
(7) PM-21: $Y = 15.0677 - 4.6737 \times EIF2S3 + 2.4380 \times MDM2 + 1.3340 \times GRB2 + 3.2085 \times NF1 - 1.3968 \times MMD - 1.9878 \times RNF4 + 1.7477 \times DUSP6$;
(8) PM-22: $Y = 13.9614 - 5.1493 \times EIF2S3 - 1.428 \times EXT2 + 2.8761 \times MDM2 + 1.9449 \times GRB2 + 3.7571 \times NF1 - 1.4987 \times MMD - 1.6345 \times RNF4 + 1.6694 \times DUSP6$.

One-Gene Signature: DUSP6

A consistent increase in the mRNA expression of the DUSP6 gene was found in the peripheral blood samples obtained from the colorectal cancer patients but not from the normal controls. The mRNA expression level of the DUSP6 gene was significantly correlated with colorectal cancer (p-value=0.0019). An odds ratio of 5.3 for the DUSP6 gene meant that a person with a relatively high mRNA expression level of DUSP6 is about 5-times more at risk of developing colorectal cancer than a person with a lower expression level (decrease of $^{\Delta}Ct(test)$ by one unit).

The measurement of the DUSP6 gene mRNA expression level was sufficient in the prediction model PM-15 and delivered a high specificity (0.82) and other good validity indexes as shown in Table 10. The results indicated that the mRNA expression level of the DUSP6 gene can be potentially used as a molecular marker for detecting colorectal cancer disease since an AUC of 0.7 to 0.8 is generally considered as a marginally useful test.

The mRNA expression level of the DUSP6 gene can be further applied as an index for monitoring the therapeutic response and as a prognostic marker for evaluation of the recurrence possibility within a certain follow-up period and survival. For example, a reduction in the mRNA expression level of the DUSP6 gene can be a direct or an indirect result from a positive therapeutic response or as an indication for a lower possibility of recurrence, better prognosis and a longer survival period.

Two-Gene Signature: DUSP6, EIF2S3

The mRNA expression level of the EIF2S3 gene was selected as the second colorectal cancer-associated molecular marker (p-value<0.0001) to improve the prediction performance during modeling (Table 10). An extremely low odds ratio of 0.006 for the EIF2S3 gene indicated that an increase in one unit of $^{\Delta}Ct(test)$ could result in a reduction of 99.4% ((1−0.006)*100) probability for having colorectal cancer.

The prediction model PM-16, which was based on the mRNA expression levels of the EIF2S3 and DUSP6 genes, discriminated the colorectal cancer patient from the control with a high specificity (nearly 85%). Other diagnostic performance characters of the PM-16 model, such as the sensitivity, accuracy and AUC, increased about 5-10% as compared to the PM-15 model, which contained only one molecular marker, DUSP6.

The value of AUC for the prediction model PM-16 was 0.82615 (Table 10), which met the criteria for a good diagnostic test. Potential clinical utilities of a two-gene signature test include applications for detecting colorectal cancer, monitoring the therapeutic response and prognosis prediction, i.e., the recurrence possibility within a certain follow-up period and survival.

Three-Gene Signature: DUSP6, EIF2S3, MDM2

The MDM2 gene (p-value=0.0009), which had a high odds ratio of 17.745, was the third cancer-associated molecular marker added for modeling of PM-16. A person with a relatively high mRNA expression level of the MDM2 gene is about 17-times more at risk of developing colorectal cancer than a person with a lower mRNA expression level (decrease of $^{\Delta}Ct(test)$ by one unit).

A 10 percent increase in the sensitivity was achieved using the PM-17 model as compared to the PM-16 model. Other three validity indexes, specificity, accuracy and AUC, of this model met the criteria for a diagnostic test with a good performance. An AUC of 0.88679 in the PM-17 model indicated potential clinical uses in developing detection assays for colorectal cancer, monitoring the therapeutic response and prognosis prediction, i.e., the recurrence possibility within a certain follow-up period and survival.

Four-Gene Signature: DUSP6, EIF2S3, MDM2, NF1

The NF1 gene was the fourth colorectal cancer-associated molecular marker (p-value=0.0032) added for modeling. The prediction model PM-18 represented a four-gene signature (Table 10). A very high odds ratio of 42.825 for NF1 provided information that an individual with a relatively high mRNA expression level is approximately 43-times more at risk of developing colorectal cancer than those with a lower expression level (decrease of $^A$Ct(test) by one unit).

An AUC of 0.90641 was obtained for PM-18, which is generally considered as an excellent diagnostic test. Furthermore, the high specificity (87%) and accuracy (81%) of this model also met the perfomiance requirement of a good diagnostic test. The potential clinical uses of a four-gene signature test include development of a diagnostic test for colorectal cancer, monitoring the therapeutic response and prognosis prediction, i.e., the recurrence possibility within a certain follow-up period and survival.

Five-Gene Signature: DUSP6, EIF2S3, MDM2, NF1, MMD

The MMD gene was added as the fifth colorectal cancer-associated molecular marker (p-value=0.0003) for the model PM-19. A higher mRNA expression level of the MMD gene was considered to have a protective effect against colorectal cancer based on the odds ratio of 0.223 (less than 1).

The diagnostic performance of PM-19 based on a five-gene signature was improved as compared to that using a four-gene signature (PM-18) since all the four validity indexes of test quality, i.e., the sensitivity, specificity, accuracy and AUC, were increased (Table 10). The five-gene signature can be applied to develop detection tests for colorectal cancer, monitoring the therapeutic response, and prognosis prediction, i.e., the recurrence possibility within a certain follow-up period and survival.

Six-Gene Signature: DUSP6, EIF2S3, MDM2, NF1, MMD, RNF4

The RNF4 gene was the sixth significant factor (p-value=0.0117) for optimization of the prediction model. Based on the odds ratio (0.195), there was an 80.5%, i.e., (1−0.195)×100) probability for decreasing the colorectal cancer risk with an increase in one unit of $^A$Ct(test), which was the normalized mRNA expression level for the RNF4 gene.

The validity indexes of the model PM-20 fulfilled the criteria of an excellent performance for diagnostic tests with 80% sensitivity, 90% specificity, 86% accuracy, and an AUC (i.e., area under the ROC) of 0.94. The six-gene signature test can potentially be used for development of clinical tests for detecting colorectal cancer, monitoring the therapeutic response and prognosis, i.e., the recurrence possibility within a certain follow-up period and survival.

Seven-Gene Signature: DUSP6, EIF2S3, MDM2, NF1, MMD, RNF4, GRB2

The GRB2 gene was chosen as the seventh molecular marker (p-value=0.0153) for further optimization of the prediction efficacy of the model. A high odds ratio (6.993) for the GRB2 gene meant an individual with a relatively high mRNA expression level of the GRB2 gene will be approximately 7-times more at risk of developing colorectal cancer than an individual with a lower mRNA expression level (decrease of $^A$Ct(test) by one unit).

The high specificity (91%), accuracy (84%) and AUC (0.94410) indicated that a seven-gene signature test can be an excellent test for diagnostic use rather than for screening purpose since the sensitivity was 74%. The adjustment of cutoff value can further increase the test's sensitivity. The seven-gene signature test can potentially be used for detecting colorectal cancer, monitoring the therapeutic response and prognosis, such as the recurrence within a certain period and survival.

Eight-Gene Signature: DUSP6, EIF2S3, MDM2, NF1, MMD, RNF4, GRB2, EXT2

The EXT2 gene has been assumed as a colorectal cancer-associated molecular marker with a p-value=0.0623, very close to the value of significance. The mRNA expression of the EXT2 gene appeared to play a protective role for colorectal cancer because of its odds ratio at 0.24.

The diagnostic accuracy of the eight-gene signature test of PM-22 was excellent with respect to its high AUC at 0.94551. Taken together with other validity indexes of the PM-22 model, the eight-gene signature test can potentially be used for development of tests for detecting colorectal cancer, monitoring the therapeutic response and prognosis of colorectal cancer.

Example 6

Primers and Probes for Quantitative Measurement of Cancer-Associated Gene Expression Table 2 lists the information on primers and probes used for quantitative measurement of mRNA levels of cancer-associated genes. To test the specificity of the primers, cDNA templates were prepared from ten different lung and colon carcinoma cell lines purchased from the Food industry Research and Development Institute (FIRDI, Hsinshu, Taiwan) and American Type Culture Collection (ATCC; Manassas, USA). The cultures were maintained under the conditions described in the instruction manual. The list of mammalian cell lines used for the preparation of cDNA templates were as follows: the human colon adenocarcinoma cell lines CC-M1 (FIRDI/BCRC 60448), DLD-1 (FIRDI/BCRC 60132), LS174T (FIRDI/BCRC 60053), the human lung carcinoma cell line A549 (FIRDI/BCRC 60074), the human lung adenocarcinoma cell line NCI-H23 (ATCC/CRL 5800), the human lung squamous cell carcinoma cell line NCI-H520 (FIRDI/BCRC 60124), the human prostate carcinoma cell line PC3 (FIRDI/BCRC 60122), the human breast carcinoma cell line MCF-7 (FIRDI/BCRC 60436), the human normal prostate cell line PZ-HPV-7 (FIRDI/BCRC 60136), and the human normal lung cell line W138 (FIRDI/BCRC 60047).

Extraction of the total mRNA from cell lines and synthesis of cDNA using reverse transcription were performed as described in Example 1. Three different pools of cDNA templates were prepared for PCR amplification tests. The first pool was the lung cDNA pool, which contained equal amount of cDNA prepared from three lung cancer cell lines, A549, NCI-H23 and NCI-H520. The second pool was the colon cDNA pool, which contained equal amounts of cDNA prepared from three colon cancer cell lines, CC-M1, DLD-1, and LS174T. The third pool was a cDNA mix, which consisted of equally mixed cDNA from seven different sources of cancer and normal cell lines, including A549, LS174T, MCF-7, CC-M1, PZ-HPV-7, PC3 and W138.

Three programs used for designing primers and probes included the web-based PROBEFINDER™ software, Primer Select (Lasergene, DNASTAR, USA) and PRIMER EXPRESS® Software, LIGHTCYCLER® Probe Design Software 2.0. The PROBEFINDER™ software from the UNIVERSAL PROBELIBRARY™ Assay Design Center helped select an optimal combination of a UNIVERSAL PROBELIBRARY™ probe (F. Hoffmann-La Roche Ltd, Basel, Switzerland) and a gene-specific primer set for gene expression analysis using a real-time PCR assay. PROBELIBRARY™ probes contain only 8-9 nucleotides in length and often target sequences near exon-exon junctions. Therefore, the total RNA sample contaminated with genomic DNA during preparation would not interfere with the measurement of transcript level of an investigated gene. Table 2 lists information on specific primer pairs, probe sets and theoretical sequences of respective corresponding amplified products.

For every amplification PCR test, the reaction mixture contained 50 ng of cDNA template, 0.2 μM each of forward and reverse primers and TAQ™ DNA Polymerase Kit (TAKARA™; Japan). Amplification reaction was performed using MJ Research PTC-100™ (Global Medical Instrumentation, Inc, MN, USA). The PCR conditions were 50° C. for 2 min, 95° C. for 10 min, 44 cycles of 95° C. for 15 sec and 60° C. for 1 min. The amplified products were analyzed using 3% agarose gel electrophoresis for confirmation of specificity.

Results

Most of the tested primer pairs were highly specific or specific for amplification of expected products. No amplicon was observed for the negative control (i.e., without the cDNA template) (Table 11). Some primer pairs, such as EIF2S3-F19/R20 (NOs: 19 and 20), EXT2-F47/R48 (SEQ ID NOs: 47 and 48), MCM4-F67/R68 (NOs. 67 and 68) and NF1-F113/R114 (SEQ ID NOs. 113 and 114), might not be suitable for assaying samples containing lung cancer cells, they were however suitable for assaying colorectal cancer. Table 2 lists the SEQ ID NOs. of primers.

Some primer pairs, such as EIF2S3-F27/R28 (SEQ ID NOs. 27 and 28), EIF2S3-F31/R32 (SEQ ID NOs. 31 and 32), GRB2-F91/R92 (SEQ ID NOs. 91 and 92) and NF1-F103/R104 (SEQ ID NOs. 103 and 104), did not show to be useful for assaying samples containing colorectal cancer cells but were suitable for assaying lung cancer.

TABLE 11*

Specificity test results of designed primer pairs

| Primer Pair Forward/Reverse | SEQ ID NO. | Size of expected amplicon (bp) | Lung cDNA pool | Colon cDNA pool | cDNA mix | NTC |
|---|---|---|---|---|---|---|
| EIF2S3 (SEQ ID NO: 1) | | | | | | |
| EIF2S3-F19/R20 | 19/20 | 78 | NN | H | H | NN |
| EIF2S3-F21/R22 | 21/22 | 108 | O | H | H | NN |
| EIF2S3-F23/R24 | 23/24 | 114 | O | H | O | NN |
| EIF2S3-F25/R26 | 25/26 | 68 | H | H | O | NN |
| EIF2S3-F27/R28 | 27/28 | 76 | H | NN | NN | NN |
| EIF2S3-F29/R30 | 29/30 | 124 | H | H | O | NN |
| EIF2S3-F31/R32 | 31/32 | 89 | O | NN | H | NN |
| EXT2 (SEQ ID NO: 2) | | | | | | |
| EXT2-F35/R36 | 35/36 | 109 | O | H | O | NN |
| EXT2-F37/R38 | 37/38 | 68 | H | H | H | NN |
| EXT2-F39/R40 | 39/40 | 73 | H | H | H | NN |
| EXT2-F41/R42 | 41/42 | 86 | H | H | O | NN |
| EXT2-F43/R44 | 43/44 | 86 | O | H | H | NN |
| EXT2-F45/R46 | 45/46 | 110 | O | H | H | NN |
| EXT2-F47/R48 | 47/48 | 109 | NN | O | O | NN |
| EXT2-F49/R50 | 49/50 | 115 | O | H | O | NN |
| EXT2-F51/R52 | 51/52 | 282 | H | H | H | NN |
| MCM4 (SEQ ID NO: 3) | | | | | | |
| MCM4-F55/R56 | 55/56 | 85 | H | O | H | NN |
| MCM4-F57/R58 | 57/58 | 76 | H | H | H | NN |
| MCM4-F59/R60 | 59/60 | 113 | H | H | O | NN |
| MCM4-F61/R62 | 61/62 | 96 | H | O | H | NN |
| MCM4-F63/R64 | 63/64 | 96 | O | O | H | NN |
| MCM4-F65/R66 | 65/66 | 120 | H | H | H | NN |
| MCM4-F67/R68 | 67/68 | 61 | NN | H | O | NN |
| MCM4-F69/R70 | 69/70 | 128 | O | O | O | NN |
| MCM4-F71/R72 | 71/72 | 181 | H | H | H | NN |
| MCM4-F73/R74 | 73/74 | 211 | H | H | H | NN |
| MDM2 (SEQ ID NO: 4) | | | | | | |
| MDM2-F77/R78 | 77/78 | 70 | O | H | H | NN |
| MDM2-F79/R80 | 79/80 | 63 | H | H | O | NN |
| MDM2-F81/R82 | 81/82 | 137 | H | H | H | NN |
| GRB2 (SEQ ID NO: 5) | | | | | | |
| GRB2-F85/R86 | 85/86 | 76 | H | H | H | NN |
| GRB2-F87/R88 | 87/88 | 89 | O | H | NN | NN |
| GRB2-F89/R90 | 89/90 | 70 | H | H | O | NN |
| GRB2-F91/R92 | 91/92 | 83 | H | NN | NN | NN |
| GRB2-F93/R94 | 93/94 | 109 | O | H | H | NN |
| GRB2-F95/R96 | 95/96 | 111 | H | H | H | NN |
| NF1 (SEQ ID NO: 6) | | | | | | |
| NF1-F99/R100 | 99/100 | 60 | H | H | H | NN |
| NF1-F101/R102 | 101/102 | 70 | H | H | H | NN |
| NF1-F103/R104 | 103/104 | 73 | H | NN | H | NN |
| NF1-F105/R106 | 105/106 | 73 | H | H | H | NN |
| NF1-F107/R108 | 107/108 | 75 | H | H | H | NN |
| NF1-F109/R110 | 109/110 | 78 | H | H | H | NN |
| NF1-F111/R112 | 111/112 | 93 | O | O | O | NN |
| NF1-F113/R114 | 113/114 | 128 | NN | H | H | NN |

TABLE 11*-continued

Specificity test results of designed primer pairs

| Primer Pair Forward/Reverse | SEQ ID NO. | Size of expected amplicon (bp) | Lung cDNA pool | Colon cDNA pool | cDNA mix | NTC |
|---|---|---|---|---|---|---|
| MMD (SEQ ID NO: 7) | | | | | | |
| MMD-F117/R118 | 117/118 | 74 | H | H | H | NN |
| MMD-F119/R120 | 119/120 | 91 | O | H | O | NN |
| RNF4 (SEQ ID NO: 8) | | | | | | |
| RNF4-F123/R124 | 123/124 | 76 | O | H | O | NN |
| RNF4-F125/R126 | 125/126 | 100 | H | H | H | NN |
| RNF4-F127/R128 | 127/128 | 102 | H | H | H | NN |
| RNF4-F129/R130 | 129/130 | 110 | O | H | H | NN |
| RNF4-F131/R132 | 131/132 | 84 | H | H | H | NN |
| RNF4-F133/R134 | 133/134 | 256 | O | H | H | NN |
| RNF4-F135/R136 | 135/136 | 209 | H | H | H | NN |
| DUSP6 (SEQ ID NO: 9) | | | | | | |
| DUSP6-F139/R140 | 139/140 | 215 | H | H | O | NN |

*The full names for abbreviations used in Table 11 are as follows:
"NTC" for negative control assay containing the same reaction mixture but no template;
"H" for highly specific, only one single product obtained;
"O" for specific, amplified product was not shown in the NTC assay;
"NTC" for no expected amplicon obtained.

Example 7

Colorectal Cancer Marker Gene Expression Analysis Based on Case-Control Studies

Fifteen molecular markers were further investigated for detecting colorectal cancer in subjects using case-control studies, in which the cases were colorectal cancer patients and the controls were normal subjects without clinical cancer.
Methods Sixty-five patients with histologically confirmed colorectal cancer were enrolled in a prospective investigational protocol approved by the Institutional Review Board at the Cheng Hsin Rehabilitation Medical Center (Taipei, Taiwan). In this example, 15 colorectal cancer patients were included in addition to the patient population disclosed in Example 4 (Table 8). The peripheral blood of each patient was collected as described in Examples 2. Table 12 lists the detailed clinicopathological features of the patient population.

TABLE 12

Clinicopathologic characteristics of colorectal cancer patients (N = 65)

| Characteristics | No. of Patients (%) |
|---|---|
| Area A | 65 (100%) |
| Age(Mean ± SE) | 62.63 (1.47) |
| Gender | |
| Male | 35 (53.8%) |
| Female | 30 (46.2%) |
| Stage | |
| 0 | 3 (4.6%) |
| I | 14 (21.5%) |
| II | 13 (20%) |
| III | 17 (26.2%) |
| IV | 13 (20%) |
| Others | 5 (7.7%) |

Sixty-five normal volunteers (without cancer) as controls were chosen from the control population in Area A (Taipei, Taiwan) described in Example 2, including 35 males and 30 females with an average age (SE) of 59.55 ( 1.63). Sample preparations, total RNA extraction, reverse transcription reaction, quantification of mRNA expression levels using real-time PCR assay and raw data normalization were as described in Example 1.

A matched case-control design with one control for each patient was applied in the study (N=130). The matching criteria included the age and gender. Sixty five consecutive patients were identified with colorectal cancer who met the inclusion criteria, while 65 controls with matched age (±3) and gender were included. Chi-square test and t-test were employed to confirm gender and age distributions between cases and controls. The mRNA expression levels of 15 investigated genes were tested statistically between cases and controls using t-test. The logistic regression models and odds ratios were used to develop a model using a combination of investigated genes to predict whether subjects had colorectal cancer. The ROC curve and AUC indicated the probability of each investigated gene and/or a combination of multiple genes in predicting whether subjects (patients) had colorectal cancer. The statistical $\alpha$ level was 0.05.

Table 13 lists the mRNA expression levels of nine genes, RNF4, GRB2, MDM2, DUSP6, NF1, IRF4, EIF2S3, EXT2, and POLDIP2, in cases and controls (with p-value<0.05) and indications of significant difference between case and control subjects using t-test (Table 13).

TABLE 13

Difference in gene mRNA expression between colorectal cancer patients and controls using t-test

| Variable and Gene | SEQ ID NO. | Average of Normalized Cycle Number (SD) | | P value |
|---|---|---|---|---|
| | | Colorectal Cancer Patients (N = 65) | Controls (N = 65) | |
| Male | | 35 (53.8%) | 35 (53.8%) | 1.000 |
| Age (SD) | | 62.83 (1.47) | 59.55 (1.63) | 0.138 |
| MCM4 | 3 | −1.2174 (0.07213) | −1.3571 (0.07946) | 0.106 |

TABLE 13-continued

Difference in gene mRNA expression between colorectal cancer patients and controls using t-test

| Variable and Gene | SEQ ID NO. | Average of Normalized Cycle Number (SD) | | P value |
|---|---|---|---|---|
| | | Colorectal Cancer Patients (N = 65) | Controls (N = 65) | |
| ZNF264 | 14 | −1.9862 (0.05972) | −1.9766 (0.09086) | 0.732 |
| RNF4 | 8*** | 2.7128 (0.08647) | 2.2608 (0.08484) | <0.001 |
| GRB2 | 5* | 2.4745 (0.07682) | 2.3145 (0.08847) | 0.050 |
| MDM2 | 4** | −0.4900 (0.06590) | −0.2260 (0.07570) | 0.001 |
| STAT2 | 13 | 2.1217 (0.07906) | 2.2074 (0.09667) | 0.694 |
| WEE1 | 11 | −0.1528 (0.09475) | −0.2843 (0.08316) | 0.059 |
| DUSP6 | 9*** | 1.6312 (0.07803) | 2.1391 (0.09396) | <0.001 |
| CPEB4 | 10 | 1.5274 (0.07096) | 1.6942 (0.09829) | 0.274 |
| MMD | 7 | 1.8295 (0.13526) | 1.7954 (0.14593) | 0.784 |
| NF1 | 6* | 0.7423 (0.07101) | 0.9678 (0.05011) | 0.030 |
| IRF4 | 12* | 0.7186 (0.07178) | 0.5135 (0.11368) | 0.032 |
| EIF2S3 | 1*** | 3.6342 (0.08035) | 3.3588 (0.06314) | <0.001 |
| EXT2 | 2** | −0.2835 (0.07266) | −0.5194 (0.06489) | 0.001 |
| POLDIP2 | 15* | 2.7789 (0.07937) | 2.5734 (0.06925) | 0.026 |

*p < 0.05;
**p < 0.01;
***p < 0.001

Logistic Regression Model

The mRNA expression levels of the six genes RNF4, MDM2, DUSP6, MMD, NF1 and EIF2S3 were statistically significant to discriminate whether patients had colorectal cancer in Logistic Regression analysis (Table 14). The three genes GRB2, EXT2 and POLDIP2 were no longer significant after controlling other investigated genes in the Logistic Regression analysis and might have a weaker correlation with colorectal cancer than the above-mentioned six genes. When the age and gender were controlled in both case and control populations, the expression level of the GRB2 gene was not significantly associated with colorectal cancer (p-value=0.125; Table 14). The expression of the GRB2 gene might have an interaction with the age or gender. When the age and gender were not controlled in Example 4, up-regulation of the GRB32 gene was associated with colorectal cancer (Table 9). However, the colorectal cancer and normal subjects in Example 4 had a similar range of age (66.3±12.6 vs. 60.9±11.0).

The mRNA expression levels of three genes MDM2, DUSP6, and NF1 were found to increase, while the other three genes RNF4, MMD and EIF2S3 were found to decrease, in the peripheral blood of colorectal cancer patients. The MDM2, DUSP6, and NF1 three genes could thus be considered as risk genes for colorectal cancer.

The odds ratios (95% confidence intervals) of significantly up-regulated genes MDM2, DUSP6 and NF1 were 9.19 (1.93~43.67), 6.017 (1.864~19.415) and 84.164 (6.596~1073.92), respectively, while those of significantly down-regulated genes RNF4, MMD and EIF2S3 were 0.072 (0.016~0.32), 0.385 (0.168~0.877) and 0.039 (0.007~0.209), respectively. The prediction model based on all 15 genes is as follows: Y=9.999−0.928×MCM4+0.763×ZNF264−2.636×RNF4−1.437×GRB2+2.218×MDM2+1.216×STAT2+0.066×WEE1+1.795×DUSP6−0.153×CPEB4−0.955×MMD+4.433×NF1+0.081×IRF4−3.248×EIF2S3−0.973×EXT2+1.539×POLDIP2. It has 82.3% accuracy rate, 81.5% sensitivity and 83.1% specificity.

TABLE 14

Prediction model based on mRNA expression of each gene using logistic regression model (82.3% accuracy)

| Gene | SEQ ID NO. | B | P value | OR | 95% C.I. of OR | |
|---|---|---|---|---|---|---|
| | | | | | Upper | Lower |
| MCM4 | 3 | −0.928 | 0.165 | 0.395 | 0.107 | 1.466 |
| ZNF264 | 14 | 0.763 | 0.233 | 2.146 | 0.612 | 7.526 |
| RNF4 | 8** | −2.636 | 0.001 | 0.072 | 0.016 | 0.321 |
| GRB2 | 5 | −1.437 | 0.125 | 0.238 | 0.038 | 1.493 |
| MDM2 | 4** | 2.218 | 0.005 | 9.190 | 1.934 | 43.669 |
| STAT2 | 13 | 1.216 | 0.074 | 3.373 | 0.891 | 12.772 |
| WEE1 | 11 | 0.066 | 0.924 | 1.069 | 0.272 | 4.193 |
| DUSP6 | 9** | 1.795 | 0.003 | 6.017 | 1.864 | 19.415 |
| CPEB4 | 10 | −0.153 | 0.761 | 0.858 | 0.321 | 2.297 |
| MMD | 7** | −0.955 | 0.023 | 0.385 | 0.168 | 0.879 |
| NF1 | 6*** | 4.433 | 0.001 | 84.164 | 6.596 | 1073.920 |
| IRF4 | 12 | 0.081 | 0.880 | 1.085 | 0.377 | 3.122 |
| EIF2S3 | 1*** | −3.248 | 0.000 | 0.039 | 0.007 | 0.209 |
| EXT2 | 2 | −0.973 | 0.279 | 0.378 | 0.065 | 2.200 |
| POLDIP2 | 15 | 1.539 | 0.076 | 4.662 | 0.852 | 25.522 |
| Constant | | 9.999 | 0.014 | 22012.838 | | |

B: regression coefficient;
OR: odds ratio;
C.I.: confidence interval;
*p < 0.05;
**p < 0.01;
***p < 0.001.

Step-Wise Logistic Regression Model

The step-wise logistic regression analysis showed that the mRNA expression levels of the six genes RNF4, MDM2, DUSP6, MMD, NF1 and EIF2S3 were significant to identify whether subjects had colorectal cancer. The three genes MDM2, DUSP6, and NF1 were significantly up-regulated, and the other three genes, RNF4, MMD, and EIF2S3 were down-regulated in colorectal cancer cases. The odds ratios (95% confidence intervals) of significantly up-regulated genes MDM2, DUSP6, and NF1 were 5.694 (1.717~18.885), 6.127 (2.429~15.46) and 34.182 (4.964~235.386), respectively, and those of significantly down-regulated genes RNF4, MMD and EIF2S3 were 0.132 (0.048~0.369), 0.432 (0.241~0.773) and 0.05 (0.012~0.211), respectively. Hosmer-Lemeshow test was insignificant (p=0.281), and accuracy rate was 84.6%.

TABLE 15

Step-wise Logistic Regression Model based on mRNA expression of colorectal cancer-associated molecular markers

| Variable | SEQ ID NO. | B | P value | OR | 95% C.I. of OR | |
|---|---|---|---|---|---|---|
| | | | | | Upper | Lower |
| RNF4 | 8*** | −2.022 | <0.001 | 0.132 | 0.048 | 0.369 |
| MDM2 | 4** | 1.739 | 0.004 | 5.694 | 1.717 | 18.885 |
| DUSP6 | 9*** | 1.813 | <0.001 | 6.127 | 2.429 | 15.460 |
| MMD | 7** | −0.840 | 0.005 | 0.432 | 0.241 | 0.773 |
| NF1 | 6*** | 3.532 | <0.001 | 34.182 | 4.964 | 235.386 |
| EIF2S3 | 1*** | −3.003 | <0.001 | 0.050 | 0.012 | 0.211 |
| Constant | | 11.231 | <0.001 | 75429.989 | | |

*p < 0.05;
**p < 0.01;
***p < 0.001;
B: Regression coefficient;
OR: odds ratio;
C.I.: confidence interval.

Table 16 lists all possible prediction models using multiple regression analysis with the step-wise approach for the case-control study cohort of N=130. The following prediction models have a good diagnostic performance and can be potentially used for development of clinical tests for detecting colorectal cancer, monitoring the therapeutic response, and prognosis, i.e., the recurrence possibility within a certain follow-up (or progress-free) period and survival.

One-Gene Signature: DUSP6, RNF4, MDM2, EIF2S3, NF1 or MMD

Each of the six colorectal cancer-correlated molecular markers DUSP6, RNF4, MDM2, EIF2S3, NF1 and MMD genes is the single variable for the prediction models PM-23, PM-24, PM-25, PM-26, PM-27 and PM-28, respectively (Table 16). The sensitivity, specificity and AUC of the one-gene signature-based prediction model ranged from about 44.6 to about 67.7%, from about 50.8 to about 72.3% and from about 0.486 to about 0.727, respectively. The PM-23 model containing the DUSP6 gene showed the best diagnostic performance, especially the AUC, among other models using the one-gene signature. The mRNA expression level of the DUSP6 gene is sufficient as a single variable in the prediction model PM-23 based on the case-control designed study cohort of N=130. The same result has been shown in the PM-15 model in Example 5, although there was a difference in the population of both study cohorts. The PM-23 model delivered a good validation index AUC of 0.727.

Two-Gene Signature: DUSP6 and RNF4

The mRNA expression level of the RNF4 gene was selected as the second colorectal cancer-associated molecular marker for the prediction model PM-29. The sensitivity of PM-29 (67.7%) was slightly higher than that of PM-16 (64%), while the specificity, accuracy, and AUC of the PM16 model showed a better performance. The PM-29 model can generally be considered as a useful test since its AUC was 0.786.

Three-Gene Signature: DUSP6, RNF4 and MDM2

The MDM2 gene was selected as the third molecular marker, which was the same as the PM-17 model (Example 5), in the prediction model PM-30 based on a 3-gene signature. The diagnostic performance of PM-30 showed an improvement in the sensitivity, accuracy and AUC. The AUC of the PM-30 model was 0.818, which met the criteria for a good diagnostic test.

Four-Gene Signature: DUSP6, RNF4, MDM2, EIF2S3

The mRNA expression level of the EIF2S3 gene, which was down-regulated in most of the colorectal cancer cases, was chosen as the fourth factor in the prediction model PM-31 in addition to DUSP6, RNF4, and MDM2.

The AUC of PM-31 was 0.86, which met the criteria for a good diagnostic test. The other validation indexes such as the sensitivity, specificity and accuracy were higher than 76%.

Five-Gene Signature: DUSP6, RNF4, MDM2, EIF2S3, NF1

The NF1 gene was added as the fifth molecular marker in the prediction model PM-32. The OR (34.2) of the NF1 gene was the highest among the colorectal-associated molecular markers based on the case-control study design (N=130). The same result was observed in the analysis disclosed in Example 5, even though not the same population of the study cohort was used for the statistical analysis.

In addition, the RNF4 gene in the PM-32 model was the only one different colorectal cancer-associated molecular marker chosen in a five-gene signature as compared to the PM-19 model in Example 4. The PM-32 model showed a better sensitivity than did the PM-19 model.

The overall diagnostic performance of the PM-32 model (a five-gene signature) was improved over the PM-31 (four-gene signature). The sensitivity, specificity and accuracy were greater than 81%. Especially, the AUC (0.893) of the PM-32 model almost met the criteria for an excellent diagnostic test.

Six-Gene Signature: DUSP6, RNF4, MDM2, EIF2S3, NF1 and MMD

The MMD gene was selected as the sixth molecular marker for the construction of the prediction model PM-33. The same six colorectal cancer-associated molecular markers were selected both in PM-33 and PM-20 (Example 5) but with different regression coefficients. The statistical analysis based on a careful case-control study cohort might be the reason for the difference.

The validity indices of the PM-33 model fulfilled the criteria of an excellent performance for diagnostic tests with 87.7% sensitivity, 81.5% specificity, 84.6% accuracy and an AUC of 0.912.

Conclusion

The risk of colorectal cancer was related to the up-regulation of the MDM2, DUSP6 and NF1 genes and the down-regulation of the RNF4, MMD and EIF2S3 genes on the basis of a case-control study design (N=130). Patients with the up-regulated expression of the MDM2, DUSP6 and/or NF1 genes were at an increased risk for colorectal cancer. The expression of the RNF4, MMD and EIF2S3 genes appeared to be independent suppressors for colorectal cancer. The same were concluded in Example 4.

Figure 3:
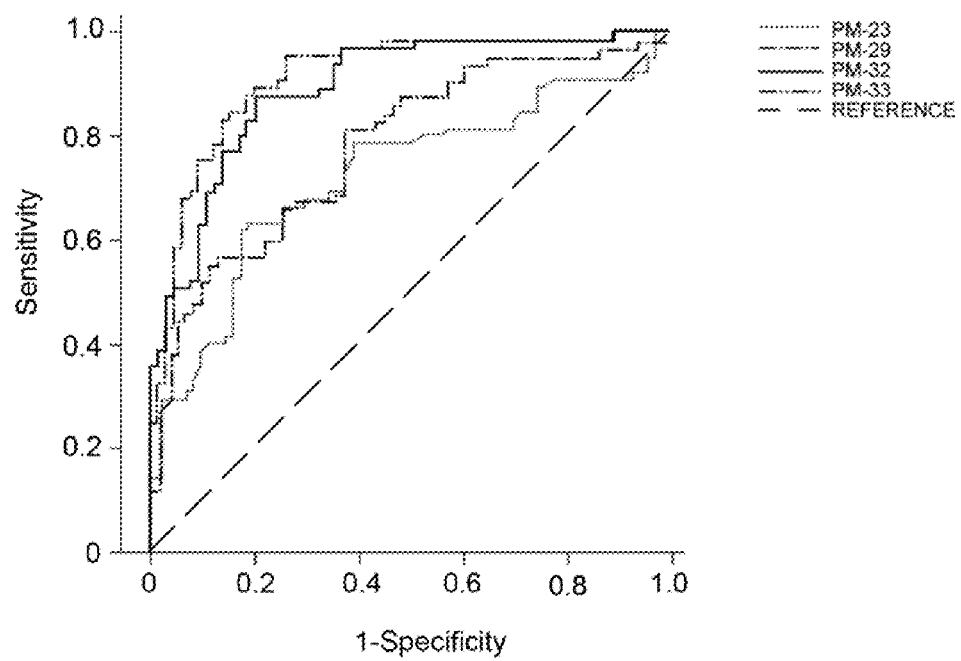
FIG. 3 is a graph of an ROC curve for prediction models using different molecular marker or combination of multiple markers listed in Table 15.

The AUC of a one-gene signature-based model for predicting whether the patients had colorectal cancer was ranging from about 49% to about 73%. Enhancements of the AUCs of the prediction models by step-wised additions of next identified colorectal cancer-associated molecular markers were shown in FIG. 3 and Table 16. The accuracy rate (the sensitivity, specificity and accuracy) of tie prediction models could clearly be improved. The optimized prediction model PM-33, which used multiple molecular markers, achieved die best diagnostic performance with the validity indexes: 88% sensitivity, 82% specificity, 85% accuracy, and an AUC of 0.912.

TABLE 16

Diagnostic performance of prediction models for study cohort N = 130 based on multiple regression analysis with step-wise approach

| Model ID | Gene No. | Sensitivity % | Specificity % | Accuracy % | AUC | SE (a) | P Value (b) | 95% C.I. Lower | Upper |
|---|---|---|---|---|---|---|---|---|---|
| PM-23 | 1 | 67.7 | 70.8 | 69.3 | 0.727 | 0.045 | <.001 | 0.638 | 0.816 |
| PM-24 | 1 | 63.1 | 67.7 | 65.4 | 0.685 | 0.047 | <.001 | 0.592 | 0.777 |
| PM-25 | 1 | 63.1 | 60.0 | 61.5 | 0.675 | 0.047 | 0.001 | 0.582 | 0.768 |
| PM-26 | 1 | 56.9 | 72.3 | 64.6 | 0.693 | 0.046 | <.001 | 0.602 | 0.784 |
| PM-27 | 1 | 58.5 | 50.8 | 54.6 | 0.610 | 0.049 | 0.030 | 0.514 | 0.707 |
| PM-28 | 1 | 44.6 | 50.8 | 47.7 | 0.486 | 0.051 | 0.784 | 0.386 | 0.586 |
| PM-29 | 2 | 67.7 | 72.3 | 70.0 | 0.786 | 0.040 | <.001 | 0.708 | 0.864 |

TABLE 16-continued

Diagnostic performance of prediction models for study cohort N = 130 based on multiple regression analysis with step-wise approach

| Model ID | Gene No. | Sensitivity % | Specificity % | Accuracy % | AUC | SE (a) | P Value (b) | 95% C.I. Lower | Upper |
|---|---|---|---|---|---|---|---|---|---|
| PM-30 | 3 | 78.5 | 72.3 | 75.4 | 0.818 | 0.037 | <.001 | 0.747 | 0.890 |
| PM-31 | 4 | 76.9 | 78.5 | 77.7 | 0.860 | 0.032 | <.001 | 0.798 | 0.923 |
| PM-32 | 5 | 83.1 | 81.5 | 82.3 | 0.893 | 0.028 | <.001 | 0.839 | 0.947 |
| PM-33 | 6 | 87.7 | 81.5 | 84.6 | 0.912 | 0.026 | <.001 | 0.862 | 0.963 |

AUC: area under ROC curve;
C.I.: Confidence Interval;
(a): nonparametric estimation;
(b): null hypothesis is AUC = 0.5.

The prediction model equations were as follows: PM-23=Y=−2.141+1.127×DUSP6; PM-24: Y=2.47×0.988×RNF4; PM-25: Y=0.335+0.982×MDM2; PM-26: Y=3.216−0.916×EIF2S3; PM-27: Y=−0.928+1.07×NF1; PM-28: Y=0.049×0.027×MMD; PM-29: Y=0.512+1.342×DUSP6−1.221×RNF4; PM-30: Y=2.19+1.235×DUSP6−1.602×RNF4+1.527×MDM2; PM-31: Y=8.174+1.185×DUSP6−1.602×RNF4+2.094×MDM2−1.607×EIF2S3; PM-32: Y=9.64+1.287×DUSP6−1.488×RNF4+1.648×MDM2−2.952×EIF2S3+2.93×NF1; PM-33: Y=11.231+1.813×DUSP6−2.022×RNF4+1.739×MDM2−3.003×EIF2S3+3.532×NF1−0.84×MMD.

Initial detection of lung or colorectal cancer in patients with or without symptoms of cancer can be done by a physician. When a physician suspects that a patient may have a lung or colorectal cancer, or is at risk of getting a lung or colorectal cancer, a physician can take a sample of blood or tissue for cancer screening according to one embodiment of the invention. The invention can also be used as a general patient screening tool. The expression levels of cancer-associated genes can be compared before and during the treatment to predict the therapeutic response to a particular cancer treatment. Similarly, the prognosis of lung or colorectal cancer can also be determined by comparing the expression levels of cancer-associated genes.

Table 17 illustrates measurements of mRNA levels of cancer marker genes in two blood samples using real-time PCR. The unit of mRNA quantity is in cycle number (Ct).

TABLE 17

| Sample | HPRT1 | EIF2S3 | EXT2 | MDM2 | GRB2 | RNF4 | MCM4 | NF1 | MMD | DUSP6 |
|---|---|---|---|---|---|---|---|---|---|---|
| LTS077 | 26.09 | 23.52 | 27.46 | 25.11 | 23.80 | 24.67 | 27.91 | 25.23 | 22.60 | 23.74 |
| NCI301 | 25.19 | 20.83 | 26.38 | 26.02 | 22.82 | 23.53 | 27.14 | 24.16 | 23.34 | 24.23 |

Normalization of measurements for each gene is made by subtracting respective cycle numbers of each gene from the reference gene HPRT1. Using DUSP6 as an example, its normalized mRNA expression level is Ct(HPRT1)−Ct(DUSP6). Table 18 shows the normalized mRNA level for each gene.

TABLE 18

| Sample | EIF2S3 | EXT2 | MDM2 | GRB2 | RNF4 | MCM4 | NF1 | MMD | DUSP6 |
|---|---|---|---|---|---|---|---|---|---|
| LTS077 | 2.57 | −1.37 | 0.98 | 2.29 | 1.42 | −1.82 | 0.86 | 3.49 | 2.35 |
| NCI301 | 4.36 | −1.19 | −0.83 | 2.37 | 1.66 | −1.95 | 1.03 | 1.85 | 0.96 |

Applying the normalized data to the prediction models such as PM-1, PM-6 or PM-7 to obtain Y and probability (P) using the logistic regression model.

TABLE 19

| | PM-1 | | PM-6 | | PM-7 | |
|---|---|---|---|---|---|---|
| Sample | Y | Probability | Y | Probability | Y | Probability |
| LTS077 | 0.641 | 0.6550 | 2.7093 | 0.9376 | 4.47 | 0.9887 |
| NCI301 | −1.51 | 0.181 | −3.246 | 0.0375 | −3.847 | 0.0209 |

Base on the cut-off value of 0.5 for the probability, sample LTS077 is predicted as "Positive" for lung Cancer, while sample NCI301 is predicted as "Negative" for lung cancer, i.e., normal.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which die present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for detecting the presence and/or severity of lung and/or colorectal cancer, comprising the steps of:
   (a) obtaining a test sample of bodily fluid comprising a nucleic acid from a subject;
   (b) isolating RNA molecules from the sample;
   (c) reverse-transcribing the RNA molecules to synthesize cDNA fragments;
   (d) amplifying the cDNA fragments of at least six cancer gene markers with primers that comprise a fluorescent label, wherein the at least six cancer gene makers are selected from:
      (i) the group consisting of: DUSP6, EIF2S3, MDM2, GRB2, RNF4, NF1, MMD, and MCM4; or
      (ii) the group consisting of: DUSP6, EIF2S3, MDM2, GRB2, RNF4, NF1, MMD, and EXT2;
   (e) measuring the quantity of the amplified cDNA fragments of the at least six cancer gene markers;
   (f) normalizing the measured quantity of the amplified cDNA fragments of each of the at least six cancer gene markers to a housekeeping gene to obtain a normalized quantity of the amplified cDNA fragments of each of the at least six cancer gene markers;
   (g) providing a logistic regression prediction model containing a positive coefficient for MDM2, GRB2, MCM4, NF1 and DUSP6 each and a negative coefficient for EIF2S3, RNF4, and MMD each;
   (h) applying the normalized quantity of the amplified cDNA fragments of each of the at least six cancer gene markers to the logistic regression prediction model to calculate the probability of cancer and/or cancer recurrence risk; and
   (i) determining the presence and/or severity of lung and/or colorectal cancer based on the calculated probability.

2. The method of claim 1, wherein the test sample is a blood sample.

3. The method of claim 1, wherein step (d) amplifies the cDNA fragments of the following six cancer gene markers: DUSP6, EIF2S3, MDM2, RNF4, NF1 and MMD.

4. The method of claim 1, wherein step (d) amplifies the cDNA fragments of the following six cancer gene markers: DUSP6, EIF2S3, GRB2, RNF4, MMD and MCM4.

5. The method of claim 1, wherein step (d) amplifies the cDNA fragments of the following eight gene markers: DUSP6, EIF2S3, MDM2, GRB2, RNF4, NF1, MMD, and MCM4.

6. The method of claim 1, wherein step (d) amplifies the cDNA fragments of the following seven cancer gene markers: DUSP6, EIF2S3, MDM2, GRB2, RNF4, NF1 and MMD.

7. The method of claim 1, wherein step (d) amplifies the cDNA fragments of the following six cancer gene markers: DUSP6, EIF2S3, GRB2, RNF4, NF1 and MMD.

8. The method of claim 1, wherein step (d) amplifies the cDNA fragments of at least:
   (i) eight cancer gene markers;
   (ii) seven cancer gene markers; or
   (iii) six cancer gene markers.

9. The method of claim 1, wherein step (d) amplifies the cDNA fragments of:
   (i) the six gene markers: DUSP6, EIF2S3, GRB2, RNF4, MMD, and MCM4/ or NF1;
   (ii) the seven gene markers: DUSP6, EIF2S3, GRB2, RNF4, MMD, MCM4, and MDM2/ or NF1;
   (iii) the six gene markers: DUSP6, EIF2S3, MDM2, NF1, MMD, and RNF4;
   (iv) the seven gene markers: DUSP6, EIF2S3, MDM2, NF1, MMD, RNF4, and GRB2; or
   (v) the eight gene markers: DUSP6, EIF2S3, MDM2, NF1, MMD, RNF4, GRB2, and EXT2.

10. The method of claim 9, wherein the amplifying step is performed by real-time polymerase chain reaction with at least one pair of primers selected from the group consisting of cancer gene marker-specific primer pairs 1 to 9 as follows:
   (i) DUSP6(SEQ ID NO: 9)-specific primer pair 1: SEQ ID NOs: 137 and 138, or SEQ ID NOs. 139 and 140;
   (ii) EIF2S3(SEQ ID NO: 1)-specific primer pair 2: SEQ ID NOs. 17 and 18, SEQ ID NOs. 19 and 20, SEQ ID NOs. 21 and 22, SEQ ID NOs. 23 and 24, SEQ ID NOs. 25 and 26, SEQ ID NOs. 27 and 28, SEQ ID NOs. 29 and 30, or SEQ ID NOs: 31 and 32;
   (iii) MDM2(SEQ ID NO: 4)-specific primer pair 3: SEQ ID NOs: 75 and 76, SEQ ID NOs: 77 and 78, SEQ ID NOs: 79 and 80, or SEQ ID NOs: 81 and 82;
   (iv) NF1(SEQ ID NO: 6)-specific primer pair 4: SEQ ID NOs: 97 and 98, SEQ ID NOs: 99 and 100, SEQ ID NOs: 101 and 102, SEQ ID NOs: 103 and 104, SEQ ID NOs: 105 and 106, SEQ ID NOs: 107 and 108, SEQ ID NOs: 109 and 110, SEQ ID NOs: 111 and 112, or SEQ ID NOs: 113 and 114;
   (v) MMD (SEQ ID NO: 7)-specific primer pair 5: SEQ ID NOs: 115 and 116, SEQ ID NOs: 117 and 118, or SEQ ID NOs: 119 and 120;
   (vi) RNF4 (SEQ ID NO: 8)-specific primer pair 6: SEQ ID NOs: 121 and 122, SEQ ID NOs: 123 and 124, SEQ ID NOs: 125 and 126, SEQ ID NOs: 127 and 128, SEQ ID NOs: 129 and 130, SEQ ID NOs: 131 and 132, SEQ ID NOs: 133 and 134, or SEQ ID NOs: 135 and 136;
   (vii) GRB2 (SEQ ID NO: 5)-specific primer pair 7: SEQ ID NOs: 83 and 84, SEQ ID NOs: 85 and 86, SEQ ID NOs: 87 and 88; SEQ ID NOs: 89 and 90, SEQ ID NOs: 91 and 92, SEQ ID NOs: 93 and 94, or SEQ ID NOs: 95 and 96;
   (viii) EXT2 (SEQ ID NO: 2)-specific primer pair 8: SEQ ID NOs: 33 and 34, SEQ ID NOs: 35 and 36, SEQ ID NOs: 37 and 38, SEQ ID NOs: 39 and 40, SEQ ID NOs: 41 and 42, SEQ ID NOs: 43 and 44, SEQ ID NOs: 45 and 46, SEQ ID NOs: 47 and 48, SEQ ID NOs: 49 and 50, or SEQ ID NOs: 51 and 52; and
   (ix) MCM4 (SEQ ID NO: 3)-specific primer pair 9: SEQ ID NOs: 53 and 54, SEQ ID NOs: 55 and 56, SEQ ID NOs: 57 and 58, SEQ ID NOs: 59 and 60, SEQ ID NOs: 61 and 62, SEQ ID NOs: 63 and 64, SEQ ID NOs: 65 and 66, SEQ ID NOs: 67 and 68, SEQ ID NOs: 69 and 70, SEQ ID NOs: 71 and 72, or SEQ ID NOs: 73 and 74.

11. The method of claim 10, wherein the EIF2S3 (SEQ ID NO: 1)-specific primer pair 2: SEQ ID NOs: 27 and 28, or SEQ ID NOs: 31 and 32, the NF1 (SEQ ID NO: 6)-specific primer pair 4: SEQ ID NOs: 103 and 104, and/or the GRB2 (SEQ ID NO: 5)-specific primer pair 7: SEQ ID NOs: 91 and 92 are selected if step (e) determines the presence and/or severity of lung cancer, and are not selected if step (e) determines the presence and/or severity of colorectal cancer.

12. The method of claim 10, wherein the EIF2S3 (SEQ ID NO: 1)-specific primer pair 2: SEQ ID NOs: 19 and 20, the NF1 (SEQ ID NO: 6)-specific primer pair 4: SEQ ID NOs: 113 and 114, the EXT2 (SEQ ID NO: 2)-specific primer pair 8: SEQ ID NOs: 47 and 48, and/or the MCM4 (SEQ ID NO: 3)-specific primer pair 9: SEQ ID NOs: 67 and 68 are selected if step (e) determines the presence and/or severity of colorectal cancer, and are not selected if step (e) determines the presence and/or severity of lung cancer.

13. A method for monitoring and/or assessing the prognosis of a patient's response to a cancer therapy, comprising the steps of:
- (a) obtaining samples of bodily fluid comprising a nucleic acid from the patient before and after receiving a cancer therapy for a lung and/or colorectal cancer;
- (b) isolating RNA molecules from the sample;
- (c) reverse-transcribing the RNA molecules to synthesize cDNA fragments;
- (d) amplifying the cDNA fragments of at least six cancer gene markers with primers that comprise a fluorescent label, wherein the at least six cancer gene markers are selected from the group consisting of DUSP6, EIF2S3, MDM2, GRB2, RNF4, NF1, MMD, MCM4;
- (e) measuring the quantity of the amplified cDNA fragments of the at least six cancer gene markers;
- (f) normalizing the measured quantity of the amplified cDNA fragments of each of the at least six cancer gene markers to a housekeeping gene to obtain a normalized quantity of the amplified cDNA fragments of each of the at least six cancer gene markers;
- (g) providing a logistic regression prediction model containing a positive coefficient for MDM2, GRB2, MCM4, NF1 and DUSP6 each and a negative coefficient for EIF2S3, RNF4, and MMD each;
- (h) applying the normalized quantity of the amplified cDNA fragments of each of the at least six cancer gene markers to a logistic regression prediction model to calculate the probability of cancer and/or cancer recurrence risk; and
- (i) evaluating the response by comparing the calculated probabilities from the samples, and thereby monitoring and/or assessing the prognosis of a patient's response to a cancer therapy;
- wherein a decrease in the probability after receiving the cancer therapy is indicative of a positive response to the therapy.

14. The method of claim 13, wherein step (d) amplifies the cDNA fragments of at least:
- (i) eight cancer gene markers;
- (ii) seven cancer gene markers; or
- (iii) six cancer gene markers.

15. The method of claim 13, wherein the test samples are blood samples.

16. A method for detecting the presence and/or severity of lung and/or colorectal cancer, comprising the steps of:
- (a) obtaining a test sample of bodily fluid comprising a nucleic acid from a subject;
- (b) isolating RNA molecules from the sample;
- (c) reverse-transcribing the RNA molecules to synthesize cDNA fragments;
- (d) amplifying the cDNA fragments of at least six cancer gene markers with primers that comprise a fluorescent label, wherein the at least six cancer gene markers are selected from:
  - (i) the group consisting of: DUSP6, EIF2S3, MDM2, GRB2, RNF4, NF1, MMD, MCM4; or
  - (ii) the group consisting of: DUSP6, EIF2S3, MDM2, GRB2, RNF4, NF1, MMD, and EXT2; and
- (e) measuring the quantity of the amplified cDNA fragments of the at least six cancer gene markers;
- (f) normalizing the measured quantity of the amplified cDNA fragments of each of the at least six cancer gene markers to a housekeeping gene to obtain a normalized quantity of the amplified cDNA fragments of each of the at least six cancer gene markers; and
- (g) comparing the normalized quantity of the amplified cDNA fragments of each of the at least six cancer gene markers to a normalized quantity of the amplified cDNA fragments of each corresponding cancer gene marker in a sample of bodily fluids from a noncancerous control; and
- (hi) determining that the subject is at risk of developing lung cancer when there is:
  - (i) an increase in the normalized quantity of the amplified cDNA fragments of DUSP6, GRB2, MCM4 and NF1 in the test sample as compared to the normalized quantity of the amplified cDNA fragments of the corresponding marker in the control; and
  - (ii) a decrease in the normalized quantity of the amplified cDNA fragments of EIF2S3, MMD, and RNF4 in the test sample as compared to the normalized quantity of the amplified cDNA fragments of the corresponding marker in the control; or
- (hii) determining that the subject is at risk of lung cancer recurrence when there is an increase in the normalized quantity of the amplified cDNA fragments of MDM2 in the test sample as compared to the normalized quantity of the amplified cDNA fragments of the corresponding marker in the control; or
- (hiii) determining that the subject is at risk of developing colorectal cancer when there is an increase in the normalized quantity of the amplified cDNA fragments of DUSP6, GRB2, MDM2 and NF1 in the test sample as compared to the normalized quantity of the amplified cDNA fragments of the corresponding marker in the control; or
- (hiv) determining that the subject is at risk of developing colorectal cancer when there is a decrease in the normalized quantity of the amplified cDNA fragments of EIF2S3, MMD, EXT2, and RNF4in the test sample as compared to the normalized quantity of the amplified cDNA fragments of the corresponding marker in the control.

17. The method of claim 16, further comprising the steps of:
- (a) normalizing the quantity of the amplified cDNA fragments of each of the at least six cancer gene markers to a housekeeping gene to obtain a normalized quantity of the amplified cDNA fragments of each of the at least six cancer gene markers;
- (b) applying the normalized quantity of the amplified cDNA fragments of each of the at least six cancer gene markers to a logistic regression prediction model to calculate the probability of cancer and/or cancer recurrence risk; and
- (c) determining the presence and/or severity of lung and/or colorectal cancer based on the calculated probability.

18. The method of claim 16, wherein the test sample is a blood sample.

19. A method for detecting the presence and/or severity of lung and/or colorectal cancer, comprising the steps of:
- (a) obtaining a test sample of bodily fluid comprising a nucleic acid from a subject;
- (b) isolating RNA molecules from the sample;
- (c) reverse-transcribing the RNA molecules to synthesize cDNA fragments;
- (d) amplifying the cDNA fragments of a set of cancer gene markers with primers that comprise a fluorescent label, wherein the set of cancer gene markers consists of 4, 5, 6, 7, or 8 genes selected from the group consisting of: DUSP6, EIF2S3, MDM2, GRB2, RNF4, NF1, MMD, and MCM4;

(e) measuring the quantity of the amplified cDNA fragments of the 4, 5, 6, 7, or 8 cancer gene markers;

(f) normalizing the measured quantity of the amplified cDNA fragments of each of the 4, 5, 6, 7, or 8 cancer gene markers to a housekeeping gene to obtain a normalized quantity of the amplified cDNA fragments of each of the at least four cancer gene markers;

(g) providing a logistic regression prediction model containing a positive coefficient for MDM2, GRB2, MCM4, NF1 and DUSP6 each and a negative coefficient for EIF2S3, RNF4, and MMD each;

(h) applying the normalized quantity of the amplified cDNA fragments of each of the 4, 5, 6, 7, or 8 cancer gene markers to the logistic regression prediction model to calculate the probability of cancer and/or cancer recurrence risk; and (i) determining the presence and/or severity of lung and/or colorectal cancer based on the calculated probability.

20. The method of claim 19, wherein step (d) amplifies the cDNA fragments of the following four gene markers: DUSP6, EIF2S3, GRB2 and RNF4.

21. The method of claim 19, wherein step (d) amplifies the cDNA fragments of the following four gene markers: DUSP6, EIF2S3, MDM2 and NF1.

22. The method of claim 19, wherein step (d) amplifies the cDNA fragments of the following four gene markers: DUSP6, EIF2S3, MDM2, and RNF4.

23. The method of claim 19, wherein:
step (d) amplifies the cDNA fragments of at least five cancer gene markers selected from the group consisting of: DUSP6, EIF2S3, MDM2, GRB2, RNF4, NF1, MMD, and MCM4;
step (e) measures the quantity of the amplified cDNA fragments of the at least five cancer gene markers;
step (f) normalizes the measured quantity of the amplified cDNA fragments of each of the at least five cancer gene markers to a housekeeping gene to obtain a normalized quantity of the amplified cDNA fragments of each of the at least five cancer gene markers;
step (g) provides a logistic regression prediction model containing a positive coefficient for MDM2, GRB2, MCM4, NF1 and DUSP6 each and a negative coefficient for EIF2S3, RNF4, and MMD each;
step (h) applies the normalized quantity of the amplified cDNA fragments of each of the at least five cancer gene markers to the logistic regression prediction model to calculate the probability of cancer and/or cancer recurrence risk; and
step (i) determines the presence and/or severity of lung and/or colorectal cancer based on the calculated probability.

24. The method of claim 23, wherein step (d) amplifies the cDNA fragments of the following five gene markers: DUSP6, EIF2S3, GRB2, RNF4 and MMD.

25. The method of claim 23, wherein step (d) amplifies the cDNA fragments of the following five gene markers: DUSP6, EIF2S3, MDM2, RNF4, and NF1.

26. The method of claim 1, wherein at least one of the primers targets an exon-exon junction.

27. The method of claim 13, wherein at least one of the primers targets an exon-exon junction.

28. The method of claim 16, wherein at least one of the primers targets an exon-exon junction.

29. The method of claim 19, wherein at least one of the primers targets an exon-exon junction.

* * * * *